United States Patent [19]
Aggarwal et al.

[11] Patent Number: 5,856,161
[45] Date of Patent: Jan. 5, 1999

[54] TUMOR NECROSIS FACTOR RECEPTOR-I-ASSOCIATED PROTEIN KINASE AND METHODS FOR ITS USE

[75] Inventors: Bharat B. Aggarwal; Bryant G. Darnay, both of Houston, Tex.

[73] Assignee: Research Development Foundation, Carson City, Nev.

[21] Appl. No.: 580,988

[22] Filed: Jan. 3, 1996

Related U.S. Application Data

[63] Continuation-in-part of Ser. No. 445,410, May 19, 1995, abandoned, which is a continuation-in-part of Ser. No. 271,424, Jul. 7, 1994, abandoned.

[51] Int. Cl.$^6$ ....................................................... C07K 1/00
[52] U.S. Cl. ........................... 435/195; 530/350; 530/351
[58] Field of Search .............................. 435/195; 530/350

[56] References Cited

PUBLICATIONS

Rubin et al, *Cancer Research* 52, 1992, pp. 878–882.
Darnay et al *JBC* 269, 1994 p. 20299.
Darnay et al *JBC* 269, 1994 p. 19687.
Song et al., *Biochem J.* 309, 1995, p. 825.
Cheng et al *Science* 267, 1995, p. 1494.
Goeddell et al *J. Cell Biochem* 18A, 1994, p. 5, (#A011).
Mosialos et al *Cell* 80, 1995, p. 389.
Rothe et al *Cell* 78, 1994, p. 681.
Tartaglia et al, *Cell* 74, 1993, p. 845.
Song et al, *JBC* 269, 1994, p. 22492.
Sato et al, *FEBS* vol. 358, 1995, p. 113.
Zhang et al *J. Immunol* 153, 1994, p. 3749.

*Primary Examiner*—Garnette D. Draper
*Attorney, Agent, or Firm*—Benjamin Aaron Adler

[57] ABSTRACT

The present invention provides an isolated and purified protein that associates with the cytoplasmic domain of the p60 form of the tumor necrosis factor receptor, having a molecular weight of about 52–55 kDa on SDS-PAGE, is a phosphoprotein, and does not bind to the p80 form of the tumor necrosis factor receptor. Also provided is an isolated and purified protein kinase that binds to the cytoplasmic domain of the p60 form of the tumor necrosis factor receptor, said kinase phosphorylates the p60 form of the tumor necrosis factor receptor. Also provided are various methods of manipulating this tumor necrosis factor receptor-associated protein and kinase in order to reduce various biological effects of tumor necrosis factor.

8 Claims, 33 Drawing Sheets

```
                                                     α2
                            α1 p60 CD      292   ADPILTALasdPIPNPLQKWEDsaHKPQsLDTDDPATLYAVVENVPP

Cyclin A    206   ITNSMRAI    LVDWLVEVGEE    YKLQ  NETLHLAVNYIDRFLSSM
Cyclin B    197   VTGNMRAI    LIDWLVQVQMK    FRLL  QETMYMTVSIIDRFMQNN
Cyclin D1    52   VLPSMRKI    VATWMLEVCEE    QKCE  EEVFPLAMNYLDRFLSLE
Cyclin E    125   LQPKMRAI    LLDWLMEVCEV    YKLH  RETFYLAQDFFDRYMATQ
Cyclin C     56   EYWKLQIF    FTNVIQALGEH    LKLR  QQVIATATVYFKRFYARY
Cyclin H     52   EEMTLCKY    YEKRLLEFCSV          FKPamprSVVGTACMYFKRFYLNN

α3                                   α4 p60 CD      340   LRWKefVRRLGLSDHEID  RLELQNGRC  L R E A  Q Y S M L  A Twrrr T

Cyclin A    247   SVLRGK   LQLVGTAAMLLASKFEEIYPPE VAE F VYITD DT Y T
Cyclin B    238   CVPKKM   LQLVGVTAMFIASKYEEMYPPE IGD F AFVTD NT Y T
Cyclin D1    93   PVKKSR   LQLLGATCMFVASKMKETIPLT AAE K LCIYT DGSI R
Cyclin E    167   eNVVKTL  LQLIGISSLFIAAKLEEIYPPK LHQ F AYVTD GA C S
Cyclin C     97   SLKSID   PVLMAPTCVFLASKVEEFGVVSntrliaaatsvlktrfsyafpkefpyrm
Cyclin H     96   SVMEYH   PRIIMLTCAFLACKVDEFNVSS P Q F V GNLRE splggekal
```

FIGURE 16A

```
         ----- α5 -----
p60 CD   383  PRREATLELLG RVLRDMD        (SEQ ID NO. 20)

Cyclin A  288  KKQVLRMEHLVLKVLTFDL       (SEQ ID NO. 21)
Cyclin B  279  KHQIRQMEMKILRALNFGL       (SEQ ID NO. 22)
Cyclin D1 135  PEELLQMELLLVNKLKWNL       (SEQ ID NO. 23)
Cyclin E  209  GDEILTMELMIMKALKWRL       (SEQ ID NO. 24)
Cyclin C  153  NHILECEFYLLELMDCCL        (SEQ ID NO. 25)
Cyclin H  142  EQILEYELLLIQQLNFHL        (SEQ ID NO. 26)
```

FIGURE 16B

A probe: αcdc2

1  2  3  4 probe: αcdk2

5  6  7  8

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 33 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 1:

CTAAGAGGAT CCAAAAAGAA GCCCTTGTGC CTG    3 3

( 2 ) INFORMATION FOR SEQ ID NO:2:

( i ) SEQUENCE CHARACTERISTICS:
        ( A ) LENGTH: 33 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 2:

TCTTAGAAGC TTTTAACTGG GCTTCATCCC AGC    33

( 2 ) INFORMATION FOR SEQ ID NO:3:

( i ) SEQUENCE CHARACTERISTICS:
        ( A ) LENGTH: 27 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 3:

CTAAGAGAAT TCAGCTTCAG TCCCACT    27

( 2 ) INFORMATION FOR SEQ ID NO:4:

( i ) SEQUENCE CHARACTERISTICS:
        ( A ) LENGTH: 27 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 4:

CTAAGAGAAT TCCCCAACTT TGCGGCT    27

( 2 ) INFORMATION FOR SEQ ID NO:5:

( i ) SEQUENCE CHARACTERISTICS:
        ( A ) LENGTH: 27 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no (v i) ORIGINAL SOURCE:

(x i) SEQUENCE DESCRIPTION: SEQ ID NO: 5:

CTAAGAGAAT TCACTGATGA CCCCGCG                                           27

(2) INFORMATION FOR SEQ ID NO:6:

(i) SEQUENCE CHARACTERISTICS:
        (A) LENGTH: 34 bp
        (B) TYPE: nucleic acid
        (C) STRANDEDNESS: single
        (D) TOPOLOGY: linear (i i) MOLECULE TYPE:
        (A) DESCRIPTION: other nucleic acid (i i i) HYPOTHETICAL: no (i v) ANTI-SENSE: no (v i) ORIGINAL SOURCE:

(x i) SEQUENCE DESCRIPTION: SEQ ID NO: 6:

TCTTAGTTAA GCTTAATCAG TCACCGGGGG TATA                                   34

(2) INFORMATION FOR SEQ ID NO:7:

(i) SEQUENCE CHARACTERISTICS:
        (A) LENGTH: 34 bp
        (B) TYPE: nucleic acid
        (C) STRANDEDNESS: single
        (D) TOPOLOGY: linear (i i) MOLECULE TYPE:
        (A) DESCRIPTION: other nucleic acid (i i i) HYPOTHETICAL: no (i v) ANTI-SENSE: no (v i) ORIGINAL SOURCE:

(x i) SEQUENCE DESCRIPTION: SEQ ID NO: 7:

TCTTAGTTAA GCTTAATCAG TCTAGGCTCT GTGG                                   34

(2) INFORMATION FOR SEQ ID NO:8:

(i) SEQUENCE CHARACTERISTICS:
        (A) LENGTH: 31 bp
        (B) TYPE: nucleic acid
        (C) STRANDEDNESS: single
        (D) TOPOLOGY: linear (i i) MOLECULE TYPE:
        (A) DESCRIPTION: other nucleic acid (i i i) HYPOTHETICAL: no (i v) ANTI-SENSE: no (v i) ORIGINAL SOURCE:

(x i) SEQUENCE DESCRIPTION: SEQ ID NO: 8:

TCTTAGTTAA GCTTAATCAT CTGAGAAGAC T                                      31

(2) INFORMATION FOR SEQ ID NO:9:

(i) SEQUENCE CHARACTERISTICS:
        (A) LENGTH: 36 bp
        (B) TYPE: nucleic acid
        (C) STRANDEDNESS: single (D) TOPOLOGY: linear (ii) MOLECULE TYPE:
(A) DESCRIPTION: other nucleic acid (iii) HYPOTHETICAL: no (iv) ANTI-SENSE: no (vi) ORIGINAL SOURCE:

(xi) SEQUENCE DESCRIPTION: SEQ ID NO: 9:

CTAAGAGGAT CCACTGATGA CCCCGCGGCG CTGTAC 36

(2) INFORMATION FOR SEQ ID NO:10:

(i) SEQUENCE CHARACTERISTICS:
(A) LENGTH: 44 bp
(B) TYPE: nucleic acid
(C) STRANDEDNESS: single
(D) TOPOLOGY: linear (ii) MOLECULE TYPE:
(A) DESCRIPTION: other nucleic acid (iii) HYPOTHETICAL: no (iv) ANTI-SENSE: no (vi) ORIGINAL SOURCE:

(xi) SEQUENCE DESCRIPTION: SEQ ID NO: 10:

CTAAGAGGAT TCACTGATGA CCCCGCGGAC GCTGTTCGCC CTGG 44

(2) INFORMATION FOR SEQ ID NO:11:

(i) SEQUENCE CHARACTERISTICS:
(A) LENGTH: 33 bp
(B) TYPE: nucleic acid
(C) STRANDEDNESS: single
(D) TOPOLOGY: linear (ii) MOLECULE TYPE:
(A) DESCRIPTION: other nucleic acid (iii) HYPOTHETICAL: no (iv) ANTI-SENSE: no (vi) ORIGINAL SOURCE:

(xi) SEQUENCE DESCRIPTION: SEQ ID NO: 11:

TCTTAGAAGC TTTTAGCGGA GCACGCGTCC CAG 33

(2) INFORMATION FOR SEQ ID NO:12:

(i) SEQUENCE CHARACTERISTICS:
(A) LENGTH: 45 bp
(B) TYPE: nucleic acid
(C) STRANDEDNESS: double
(D) TOPOLOGY: linear (ii) MOLECULE TYPE:
(A) DESCRIPTION: other nucleic acid (iii) HYPOTHETICAL: no (iv) ANTI-SENSE: no (vi) ORIGINAL SOURCE:

(xi) SEQUENCE DESCRIPTION: SEQ ID NO: 12:

TTGTTACAAG GGACTTTCCG CTGGGGACTT TCCAGGGAGG CGTGG 45

( 2 ) INFORMATION FOR SEQ ID NO:13:

( i ) SEQUENCE CHARACTERISTICS:
        ( A ) LENGTH: 45 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 13:

TTGTTACAAC TCACTTTCCG CTGCTCACTT TCCAGGGAGG CGTGG    45

( 2 ) INFORMATION FOR SEQ ID NO:14:

( i ) SEQUENCE CHARACTERISTICS:
        ( A ) LENGTH: 32 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 14:

CTAAGAGAAT TCGCTACCAA CGGTGGAAGT CC    32

( 2 ) INFORMATION FOR SEQ ID NO:15:

( i ) SEQUENCE CHARACTERISTICS:
        ( A ) LENGTH: 27 bp
        ( B ) TYPE: nucleic acid
        ( C ) STRANDEDNESS: single
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( v i ) ORIGINAL SOURCE:

( x i ) SEQUENCE DESCRIPTION: SEQ ID NO: 15:

GACGTACTCG AGTCATCTGA GAAGACT    27

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 16:

Gly Thr Tyr Gly Val Val
                      5

(2) INFORMATION FOR SEQ ID NO:17:

(i) SEQUENCE CHARACTERISTICS:
      (A) LENGTH: 7 amino acids
      (B) TYPE: amino acid
      (C) STRANDEDNESS:
      (D) TOPOLOGY: linear (ii) MOLECULE TYPE:
      (A) DESCRIPTION: peptide (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 17:

Ala Thr Leu Tyr Ala Val Val
                      5

(2) INFORMATION FOR SEQ ID NO:18:

(i) SEQUENCE CHARACTERISTICS:
      (A) LENGTH: 5 amino acids
      (B) TYPE: amino acid
      (C) STRANDEDNESS:
      (D) TOPOLOGY: linear (ii) MOLECULE TYPE:
      (A) DESCRIPTION: peptide (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 18:

Leu Xaa Cys Xaa Glu
                  5

(2) INFORMATION FOR SEQ ID NO:19:

(i) SEQUENCE CHARACTERISTICS:
      (A) LENGTH: 13 amino acids
      (B) TYPE: amino acid
      (C) STRANDEDNESS:
      (D) TOPOLOGY: linear (ii) MOLECULE TYPE:
      (A) DESCRIPTION: peptide (iii) HYPOTHETICAL: no (iv) ANTI-SENSE: no (v) FRAGMENT TYPE: internal (v i) ORIGINAL SOURCE:

(x i) SEQUENCE DESCRIPTION: SEQ ID NO: 19:

Asp Met Asp Leu Leu Gly Cys Leu Glu Asp Ile Glu Glu
                    5                   10

(2) INFORMATION FOR SEQ ID NO:20:

(i) SEQUENCE CHARACTERISTICS:
        (A) LENGTH: 108 amino acids
        (B) TYPE: amino acid
        (C) STRANDEDNESS:
        (D) TOPOLOGY: linear (i i) MOLECULE TYPE:
        (A) DESCRIPTION: protein (i i i) HYPOTHETICAL: no (i v) ANTI-SENSE: no (v) FRAGMENT TYPE: internal (v i) ORIGINAL SOURCE:

(x i) SEQUENCE DESCRIPTION: SEQ ID NO: 20:

Ala Asp Pro Ile Leu Thr Ala Leu Ala Ser Asp Pro Ile Pro Asn
                    5                   10                  15
Pro Leu Gln Lys Trp Glu Asp Ser Ala His Lys Pro Gln Ser Leu
                    20                  25                  30
Asp Thr Asp Asp Pro Ala Thr Leu Tyr Ala Val Val Glu Asn Val
                    35                  40                  45
Pro Pro Leu Arg Trp Lys Glu Phe Val Arg Arg Leu Gly Leu Ser
                    50                  55                  60
Asp His Glu Ile Asp Arg Leu Glu Leu Gln Asn Gly Arg Cys Leu
                    65                  70                  75
Arg Glu Ala Gln Tyr Ser Met Leu Ala Thr Trp Arg Arg Arg Thr
                    80                  85                  90
Pro Arg Arg Glu Ala Thr Leu Glu Leu Leu Gly Arg Val Leu Arg
                    95                  100                 105
Asp Met Asp (2) INFORMATION FOR SEQ ID NO:21:

(i) SEQUENCE CHARACTERISTICS:
        (A) LENGTH: 101 amino acids
        (B) TYPE: amino acid
        (C) STRANDEDNESS:
        (D) TOPOLOGY: linear (i i) MOLECULE TYPE:
        (A) DESCRIPTION: protein (i i i) HYPOTHETICAL: no (i v) ANTI-SENSE: no (v) FRAGMENT TYPE: internal (v i) ORIGINAL SOURCE:

(x i) SEQUENCE DESCRIPTION: SEQ ID NO: 21:

Ile Thr Asn Ser Met Arg Ala Ile Leu Val Asp Trp Leu Val Glu
                    5                   10                  15
Val Gly Glu Glu Tyr Lys Leu Gln Asn Glu Thr Leu His Leu Ala
                    20                  25                  30

| Val | Asn | Tyr | Ile | Asp | Arg | Phe | Leu | Ser | Ser | Met | Ser | Val | Leu | Arg |
|---|---|---|---|---|---|---|---|---|---|---|---|---|---|---|
| | | | | 35 | | | | | 40 | | | | | 45 |

| Gly | Lys | Leu | Gln | Leu | Val | Gly | Thr | Ala | Ala | Met | Leu | Leu | Ala | Ser |
|---|---|---|---|---|---|---|---|---|---|---|---|---|---|---|
| | | | | 50 | | | | | 55 | | | | | 60 |

| Lys | Phe | Glu | Glu | Ile | Tyr | Pro | Pro | Glu | Val | Ala | Glu | Phe | Val | Tyr |
|---|---|---|---|---|---|---|---|---|---|---|---|---|---|---|
| | | | | 65 | | | | | 70 | | | | | 75 |

| Ile | Thr | Asp | Asp | Thr | Tyr | Thr | Lys | Lys | Gln | Val | Leu | Arg | Met | Glu |
|---|---|---|---|---|---|---|---|---|---|---|---|---|---|---|
| | | | | 80 | | | | | 85 | | | | | 90 |

| His | Leu | Val | Leu | Lys | Val | Leu | Thr | Phe | Asp | Leu |
|---|---|---|---|---|---|---|---|---|---|---|
| | | | | 95 | | | | | 100 | |

(2) INFORMATION FOR SEQ ID NO:22:

(i) SEQUENCE CHARACTERISTICS:
        (A) LENGTH: 101 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 22:

| Val | Thr | Gly | Asn | Met | Arg | Ala | Ile | Leu | Ile | Asp | Trp | Leu | Val | Gln |
|---|---|---|---|---|---|---|---|---|---|---|---|---|---|---|
| | | | | 5 | | | | | 10 | | | | | 15 |

| Val | Gln | Met | Lys | Phe | Arg | Leu | Leu | Gln | Glu | Thr | Met | Tyr | Met | Thr |
|---|---|---|---|---|---|---|---|---|---|---|---|---|---|---|
| | | | | 20 | | | | | 25 | | | | | 30 |

| Val | Ser | Ile | Ile | Asp | Arg | Phe | Met | Gln | Asn | Asn | Cys | Val | Pro | Lys |
|---|---|---|---|---|---|---|---|---|---|---|---|---|---|---|
| | | | | 35 | | | | | 40 | | | | | 45 |

| Lys | Met | Leu | Gln | Leu | Val | Gly | Val | Thr | Ala | Met | Phe | Ile | Ala | Ser |
|---|---|---|---|---|---|---|---|---|---|---|---|---|---|---|
| | | | | 50 | | | | | 55 | | | | | 60 |

| Lys | Tyr | Glu | Glu | Met | Tyr | Pro | Pro | Glu | Ile | Gly | Asp | Phe | Ala | Phe |
|---|---|---|---|---|---|---|---|---|---|---|---|---|---|---|
| | | | | 65 | | | | | 70 | | | | | 75 |

| Val | Thr | Asp | Asn | Thr | Tyr | Thr | Lys | His | Gln | Ile | Arg | Gln | Met | Asp |
|---|---|---|---|---|---|---|---|---|---|---|---|---|---|---|
| | | | | 80 | | | | | 85 | | | | | 90 |

| Met | Lys | Ile | Leu | Arg | Ala | Leu | Asn | Phe | Gly | Leu |
|---|---|---|---|---|---|---|---|---|---|---|
| | | | | 95 | | | | | 100 | |

(2) INFORMATION FOR SEQ ID NO:23:

(i) SEQUENCE CHARACTERISTICS:
        (A) LENGTH: 102 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 23:

| Val | Leu | Pro | Ser | Met | Arg | Lys | Ile | Val | Ala | Thr | Trp | Met | Leu | Glu |
|-----|-----|-----|-----|-----|-----|-----|-----|-----|-----|-----|-----|-----|-----|-----|
|     |     |     |     | 5   |     |     |     |     | 10  |     |     |     |     | 15  |
| Val | Cys | Glu | Glu | Gln | Lys | Cys | Glu | Glu | Glu | Val | Phe | Pro | Leu | Ala |
|     |     |     |     | 20  |     |     |     |     | 25  |     |     |     |     | 30  |
| Met | Asn | Tyr | Leu | Asp | Arg | Phe | Leu | Ser | Leu | Glu | Pro | Val | Lys | Lys |
|     |     |     |     | 35  |     |     |     |     | 40  |     |     |     |     | 45  |
| Ser | Arg | Leu | Gln | Leu | Leu | Gly | Ala | Thr | Cys | Met | Phe | Val | Ala | Ser |
|     |     |     |     | 50  |     |     |     |     | 55  |     |     |     |     | 60  |
| Lys | Met | Lys | Glu | Thr | Ile | Pro | Leu | Thr | Ala | Ala | Glu | Lys | Leu | Cys |
|     |     |     |     | 65  |     |     |     |     | 70  |     |     |     |     | 75  |
| Ile | Tyr | Thr | Asp | Gly | Ser | Ile | Arg | Pro | Glu | Glu | Leu | Leu | Gln | Met |
|     |     |     |     | 80  |     |     |     |     | 85  |     |     |     |     | 90  |
| Glu | Leu | Leu | Leu | Val | Asn | Lys | Leu | Lys | Trp | Asn | Leu |     |     |     |
|     |     |     |     | 95  |     |     |     |     | 100 |     |     |     |     |     |

( 2 ) INFORMATION FOR SEQ ID NO:24:

( i ) SEQUENCE CHARACTERISTICS:
        ( A ) LENGTH: 102 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: no ( i v ) ANTI-SENSE: no ( v ) FRAGMENT TYPE: internal ( v i ) ORIGINAL SOURCE:

( x i ) SEQUENCE DESCRIPTION: SEQ ID NO: 24:

| Leu | Gln | Pro | Lys | Met | Arg | Ala | Ile | Leu | Leu | Asp | Trp | Leu | Met | Glu |
|-----|-----|-----|-----|-----|-----|-----|-----|-----|-----|-----|-----|-----|-----|-----|
|     |     |     |     | 5   |     |     |     |     | 10  |     |     |     |     | 15  |
| Val | Cys | Glu | Val | Tyr | Lys | Leu | His | Arg | Glu | Thr | Phe | Tyr | Leu | Ala |
|     |     |     |     | 20  |     |     |     |     | 25  |     |     |     |     | 30  |
| Gln | Asp | Phe | Phe | Asp | Arg | Tyr | Met | Ala | Thr | Gln | Glu | Asn | Val | Val |
|     |     |     |     | 35  |     |     |     |     | 40  |     |     |     |     | 45  |
| Lys | Thr | Leu | Leu | Gln | Leu | Ile | Gly | Ile | Ser | Ser | Leu | Phe | Ile | Ala |
|     |     |     |     | 50  |     |     |     |     | 55  |     |     |     |     | 60  |
| Ala | Lys | Leu | Glu | Glu | Ile | Tyr | Pro | Pro | Lys | Leu | His | Gln | Phe | Ala |
|     |     |     |     | 65  |     |     |     |     | 70  |     |     |     |     | 75  |
| Tyr | Val | Thr | Asp | Gly | Ala | Cys | Ser | Gly | Asp | Glu | Ile | Leu | Thr | Met |
|     |     |     |     | 80  |     |     |     |     | 85  |     |     |     |     | 90  |
| Glu | Leu | Met | Ile | Met | Lys | Ala | Leu | Lys | Trp | Arg | Leu |     |     |     |
|     |     |     |     | 95  |     |     |     |     | 100 |     |     |     |     |     |

( 2 ) INFORMATION FOR SEQ ID NO:25:

( i ) SEQUENCE CHARACTERISTICS:
        ( A ) LENGTH: 115 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: no ( i v ) ANTI-SENSE: no ( v ) FRAGMENT TYPE: internal ( v i ) ORIGINAL SOURCE:

( x i ) SEQUENCE DESCRIPTION: SEQ ID NO: 25:

| Glu | Tyr | Trp | Lys | Leu | Gln | Ile | Phe | Phe | Thr | Asn | Val | Ile | Gln | Ala |
|---|---|---|---|---|---|---|---|---|---|---|---|---|---|---|
| | | | | 5 | | | | | 10 | | | | | 15 |
| Leu | Gly | Glu | His | Leu | Lys | Leu | Arg | Gln | Gln | Val | Ile | Ala | Thr | Ala |
| | | | | 20 | | | | | 25 | | | | | 30 |
| Thr | Val | Tyr | Phe | Lys | Arg | Phe | Tyr | Ala | Arg | Tyr | Ser | Leu | Lys | Ser |
| | | | | 35 | | | | | 40 | | | | | 45 |
| Ile | Asp | Pro | Val | Leu | Met | Ala | Pro | Thr | Cys | Val | Phe | Leu | Ala | Ser |
| | | | | 50 | | | | | 55 | | | | | 60 |
| Lys | Val | Glu | Glu | Phe | Gly | Val | Val | Ser | Asn | Thr | Arg | Leu | Ile | Ala |
| | | | | 65 | | | | | 70 | | | | | 75 |
| Ala | Ala | Thr | Ser | Val | Leu | Lys | Thr | Arg | Phe | Ser | Tyr | Ala | Phe | Pro |
| | | | | 80 | | | | | 85 | | | | | 90 |
| Lys | Glu | Phe | Pro | Tyr | Arg | Met | Asn | His | Ile | Leu | Glu | Cys | Glu | Phe |
| | | | | 95 | | | | | 100 | | | | | 105 |
| Tyr | Leu | Leu | Glu | Leu | Met | Asp | Cys | Cys | Leu | | | | | |
| | | | | 110 | | | | | 115 | | | | | |

( 2 ) INFORMATION FOR SEQ ID NO:26:

( i ) SEQUENCE CHARACTERISTICS:
( A ) LENGTH: 107 amino acids
( B ) TYPE: amino acid
( C ) STRANDEDNESS:
( D ) TOPOLOGY: linear ( i i ) MOLECULE TYPE:
( A ) DESCRIPTION: protein ( i i i ) HYPOTHETICAL: no ( i v ) ANTI-SENSE: no ( v ) FRAGMENT TYPE: internal ( v i ) ORIGINAL SOURCE:

( x i ) SEQUENCE DESCRIPTION: SEQ ID NO: 26:

| Glu | Glu | Met | Thr | Leu | Cys | Lys | Tyr | Tyr | Glu | Lys | Arg | Leu | Leu | Glu |
|---|---|---|---|---|---|---|---|---|---|---|---|---|---|---|
| | | | | 5 | | | | | 10 | | | | | 15 |
| Phe | Cys | Ser | Val | Phe | Lys | Pro | Ala | Met | Pro | Arg | Ser | Val | Val | Gly |
| | | | | 20 | | | | | 25 | | | | | 30 |
| Thr | Ala | Cys | Met | Tyr | Phe | Lys | Arg | Phe | Tyr | Leu | Asn | Asn | Ser | Val |
| | | | | 35 | | | | | 40 | | | | | 45 |
| Met | Glu | Tyr | His | Pro | Arg | Ile | Ile | Met | Leu | Thr | Cys | Ala | Phe | Leu |
| | | | | 50 | | | | | 55 | | | | | 60 |
| Ala | Cys | Lys | Val | Asp | Glu | Phe | Asn | Val | Ser | Ser | Pro | Gln | Phe | Val |
| | | | | 65 | | | | | 70 | | | | | 75 |
| Gly | Asn | Leu | Arg | Glu | Ser | Pro | Leu | Gly | Gly | Glu | Lys | Ala | Leu | Glu |
| | | | | 80 | | | | | 85 | | | | | 90 |
| Gln | Ile | Leu | Glu | Tyr | Glu | Leu | Leu | Leu | Ile | Gln | Gln | Leu | Asn | Phe |
| | | | | 95 | | | | | 100 | | | | | 105 |
| His | Leu | | | | | | | | | | | | | |

( 2 ) INFORMATION FOR SEQ ID NO:27:

( i ) SEQUENCE CHARACTERISTICS:
( A ) LENGTH: 25 amino acids ( B ) TYPE: amino acid
( C ) STRANDEDNESS:
( D ) TOPOLOGY: linear ( i i ) MOLECULE TYPE:
( A ) DESCRIPTION: protein ( i i i ) HYPOTHETICAL: no ( i v ) ANTI-SENSE: no ( v ) FRAGMENT TYPE: internal ( v i ) ORIGINAL SOURCE:

( x i ) SEQUENCE DESCRIPTION: SEQ ID NO: 27:

Thr Asp Asp Pro Ala Thr Leu Tyr Ala Val Val Glu Asn Val Pro
              5                    10                   15

Pro Leu Arg Trp Lys Glu Phe Val Arg Arg
              20                   25

TUMOR NECROSIS FACTOR RECEPTOR-I-ASSOCIATED PROTEIN KINASE AND METHODS FOR ITS USE

CROSS REFERENCE TO RELATED APPLICATIONS

This application is a continuation in part of U.S. Ser. No. 08/445,410, filed May 19, 1995, now abandoned, which is a continuation in part of U.S. Ser. No. 08/271,424, filed Jul. 7, 1994, now abandoned.

BACKGROUND OF THE INVENTION

1. Field of the Invention

The present invention relates generally to the fields of cytokine biology and protein chemistry. More specifically, the present invention relates to a novel protein kinase associated with the p60 form of the tumor necrosis factor receptor.

2. Description of the Related Art

Tumor necrosis factor (TNF), a homotrimer of 17 kDa subunits, is a cytokine produced mainly by activated macrophages and several other cell types. TNF is pleiotropic, induces cytotoxicity, cachexia, and septic shock, shows anti-viral, anti-inflammatory, and immunoregulatory activities, and stimulates the growth of certain cells. Two different receptors, termed p60 (also known as p55 or TNFR-I) and p80 (also known as p75 or TNFR-II), bind TNF with high affinity. The extracellular domain of both p60 and p80 share 28% sequence identity with each other and other members of the TNF/nerve growth factor (NGF) receptor family. Little homology exists between the cytoplasmic domains of the p60 and p80 forms of the tumor necrosis factor receptor.

Intracellular events linking the activation of TNF receptors to specific cellular responses are unclear. TNF activates the transcriptional complex nuclear factor kappa B (NFkB) within minutes, transmitting a signal from the receptor to the nucleus. Additionally, a TNF signaling pathway involving the breakdown of sphingomyelin to ceramide and stimulation of a ceramide-activated kinase have been described. TNF augments the phosphorylation state of several proteins such as the small heat shock protein (hsp 27), eukaryotic initiation factor 4E, inhibitory subunit of NF-κB (IκB-α), and epidermal growth factor receptor. Similarly, a number of unidentified proteins incorporate phosphate in response to TNF. Various protein kinase activities have been demonstrated to be rapidly and transiently activated upon TNF treatment.

The functional role of the cytoplasmic domain of p60 for signaling the cytotoxic response to TNF has been reported. Brakebusch et al. expressed a series of truncated human p60 receptors in murine L929 cells and observed that deletion of 50% of the cytoplasmic domain resulted in the loss of the TNF cytotoxic effect but not shedding of the receptor. Similarly, Tartaglia et al. demonstrated that expression of human p60 lacking most of the cytoplasmic domain rendered L929 cells defective in TNF responses. Additionally, Tartaglia et al. showed that a region within the cytoplasmic domain of p60 termed the "death domain" (residues 324–426) was necessary for generation of the TNF cytotoxic signal in mouse L929 cells. Thus, the cytoplasmic domain may contain structural information necessary for interaction with intracellular components required for TNF signaling.

Receptors that lack kinase activity transmit their signals through recruitment of specific kinases by their cytoplasmic domains. However, there has been no evidence of any proteins in association with the cytoplasmic domain of p60 or of phosphorylation of this receptor. Manipulation of such protein would provide an avenue for regulation of TNF's biological activities.

In spite of the conserved features of the extracellular domains of the p60 and p80 forms of the tumor necrosis factor (TNF) receptor, it has been difficult to identify common motifs in their intracellular regions. Like other members of the TNF/NGF receptor family, the p60 and p80 forms of the TNF receptor do not contain consensus sequences characteristic of tyrosine or serine/threonine kinases, or any other signal transduction motifs. However, ligand binding to the TNF receptor activates a wide variety of putative second-messenger events, including a rapid increase in protein phosphorylation. It is unclear which of these processes form the link between ligand binding at the cell-surface and the profound effects that TNF has upon cell function.

Efforts to identify receptor domains critical for cellular signaling have relied on mutational analysis. The deletion analysis reported by Brakebusch et al. indicated that truncation of at least half of the cytoplasmic domain of p60 receptor abolished the ability of TNF to signal for cytotoxicity. Additionally, a mutant receptor lacking most of its cytoplasmic domain interfered with the endogenous wild-type receptor, suggesting that receptor clustering is necessary for signal transmission. Similarly, Tartaglia et al. demonstrated that the expression of a truncated human p60 receptor in mouse cells suppressed the signaling of the endogenous mouse TNF receptors in response to the ligand. A more detailed mutational study has shown that a region residing near the C-terminal end of the cytoplasmic domain (termed the "death domain") is necessary for transmitting the cytotoxic effect of TNF. Interestingly, this death domain shares weak homology with a region found in the cytoplasmic domain of the Fas antigen that is necessary for apoptotic signal transduction.

The intracellular domain of the p60 receptor has been shown to interact with several proteins, including TRADD, TRAP-1, TRAP-2, and 55.11. Both TRAP-1 and TRAP-2 exhibit homology to heat shock protein 90, and they associate with a segment of the cytoplasmic domain upstream of the death domain (Song et al., 1995). Three groups using the yeast two hybrid screen and the intracellular domain of the p60 TNF receptor as bait independently isolated the death domain of the p60 receptor (Boldin et al., 1995a; Hsu et al., 1995; Song et al., 1994), thus suggesting a strong tendency of the cytoplasmic domain to associate with itself. In addition to these proteins, a clone designated 55.11 with some homology to a subunit of the proteosome was identified that also interacts with the N-terminal half of the cytoplasmic domain (Boldin et al., 1995b). A novel cDNA termed TRADD, which exhibits 35% homology with the death domain of p60 receptor, has been shown to induce cell death and NF-kB activation (Cleveland and Ihle, 1995; Hsu et al., 1995).

One of the earliest cellular responses to TNF is the activation of the transcriptional factor NF-kB (Baeuerle and Henkel, .1994; Siebenlist et al., 1994; Thanos and Maniatis, 1995). The activation of NF-kB requires rapid phosphorylation and degradation of IkBα (Alkalay et al., 1995; Beg et al., 1993; Brown et al., 1993; Cordle et al., 1993; DiDonato et al., 1995; Finco, et al., 1994; Henkel et al., 1993; Lin et al., 1995; Miyamoto et al., 1994; Rice and Ernst, 1993; Sun et al., 1993; Sun et al., 1994; Traenckner et al., 1994). What enzymes are responsible for phosphorylation and degradation of IkBα, however, are unknown. Recent reports have shown that the signal-induced sites of phosphorylation on IkBα are localized on serine residues 32 and 36 (Brown et al., 1995; Traenckner et al., 1995) and that phosphorylation at these sites is a prerequisite for IkBα ubiquitination, which in turn leads to its degradation by the 26S proteasome (Chen et al., 1995). The kinase responsible for phosphorylation of these two serine residues of IkBα remains elusive. It is possible, however, that p60TRAK is the serine kinase responsible for IkBα phosphorylation either directly or indirectly.

While protein kinases are evident in signaling post-receptor events of TNF, the role of protein phosphatases is less well understood. However, protein tyrosine phosphatase inhibitors blocked TNF-induced NF-kB activation. Thus, a kinase necessary for TNF-mediated activation of NF-kB is down-regulated by tyrosine phosphorylation and this kinase may be p60TRAK.

The prior art is deficient in the lack of effective means of regulating the biological activities, including the cytotoxic effects of tumor necrosis factor. The present invention fulfills this longstanding need and desire in the art.

SUMMARY OF THE INVENTION

The present invention uses a glutathione-S-transferase (GST) fusion protein containing the cytoplasmic domain of p60 (GST-p60CDΔ1) linked to glutathione agarose to 1) identify proteins from cell extracts that are associated with the cytoplasmic domain of the p60 form of the tumor necrosis factor receptor; 2) characterize associated kinase activity; and 3) illustrate that the cytoplasmic domain of the p60 form of the tumor necrosis factor receptor is phosphorylated. The present invention provide the first evidence of a specific kinase that associates with the cytoplasmic domain of the p60 form of the tumor necrosis factor receptor and causes its phosphorylation. For the purposes of the present invention, this kinase is termed p60-Tumor Necrosis Factor Receptor Associated Kinase (p60TRAK).

In one embodiment of the present invention, there is provided an isolated and purified protein that associates with the cytoplasmic domain of the p60 form of the tumor necrosis factor receptor, having a molecular weight of about 52–55 kDa as determined by SDS-PAGE, is a phosphoprotein, and does not bind to the p80 form of the tumor necrosis factor receptor. For the purposes of the present invention, this protein is termed p60-Tumor Necrosis Factor Receptor Associated Protein (p60TRAP).

In another embodiment of the present invention, there is provided an isolated and purified protein kinase that binds to the cytoplasmic domain of the p60 form of the tumor necrosis factor receptor, said kinase phosphorylates the p60 form of the tumor necrosis factor receptor.

In yet another embodiment of the present invention, there is provided a pharmaceutical composition comprising a competitive inhibitor of the kinase of the present invention and a pharmaceutically acceptable carrier.

In still yet another embodiment of the present invention, there is provided a method of treating a pathophysiological state characterized by an undesirable physiological level of tumor necrosis factor comprising the step of administering a pharmacologically effective dose of the pharmaceutical composition of the present invention to a human.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2A shows U-937 cells ($4.0 \times 10^6$/ml) were labeled with a mixture of $^{35}$S-methionine and cysteine (50 µCi/ml) in 30 ml of methionine/cysteine-free RPMI-1640 supplemented with 10% dialyzed FBS and grown for 4 hours at 37° C. Cells were collected, washed 3× with RPMI-1640, adjusted to $1.5 \times 10^6$/ml, and incubated at 37° C. for 1 hour. Cells were incubated without (−) or with (+) 5 nM TNF for 5 minutes, washed 2× with cold PBS and lysed, and in vitro binding to GST and GST-p60CDΔ1 (Δ1) performed as described below. Adsorbed proteins were subjected to 7.5% SDS-PAGE, and the dried gel analyzed by a Phosphorimager. Molecular masses in kDa are as indicated; the arrow indicates the position of the 52-kDa protein. FIG. 2B shows that U-937 cells ($4.0 \times 10^6$/ml) were labeled with carrier free [$^{32}$P]orthophosphate (500 µCi/ml) in 30 ml of phosphate-free RPMI-1640 for 2 hours. Cells were washed with fresh medium, treated without (−) or with (+) 5 nM TNF for 5 minutes and processed as described above.

FIG. 4A shows that in vitro kinase assays were performed after binding reactions with the indicated final concentration of divalent cation for 10 minutes at 37° C. and subjected to SDS-PAGE. FIGS. 4B and 4C show that in vitro kinase assays were performed with 10 mM $MnCl_2$ and the corresponding substrates for 10 minutes at 37° C. and subjected to 7% (FIG. 4B) or 12% (FIG. 4C) SDS-PAGE. Arrows (FIG. 4B) or asterisk (FIG. 4C) indicate positions of proteins after staining with Coomassie Blue. Shown are phosphorimages of the dried gels.

In FIG. 5A and FIG. 5B, Serum-starved MCF-7 cells (0.5×10⁶) (FIG. 5A) or foreskin fibroblasts (0.5×10⁶) (FIG. 5B) were incubated with 5 nM TNF for the indicated period of time, and scraped with 3×3 ml Versene buffer. Approximately 100 μg of cell lysate was used for in vitro binding to GST-p60CDΔ1, and kinase assays with 10 mM MgCl$_2$ were performed as described below. In FIG. 5C, serum-starved U-937 cells (0.5×10⁶) were incubated in the presence of 5 nM TNF for the indicated period of time and washed 2× with cold PBS, and in vitro binding to GST-p60CDΔ1 and kinase assays with 10 mM MnCl$_2$ were performed as described below. Proteins were subjected to SDS-PAGE and a phosphorimage of the dried gel is shown.

In FIG. 6A, the entire cytoplasmic domain (residues 205 to 426) of the p60 TNF receptor is shown as p60CD. The letters S/T/P and D/E designate the serine-, threonine- and proline-rich and acidic-residue rich regions as described below. Each deletion mutant was expressed as a fusion protein linked to GST as described below. In FIG. 6B, approximately equal amounts of the purified GST fusion proteins were analyzed by 9% SDS-PAGE and stained with Coomassie Blue. Molecular mass standards are expressed in kDa.

FIG. 15A shows a schematic of the cytoplasmic domain of the p60 TNF receptor (residues 205–426) with the deletion constructs used herein. All deletions were expressed as GST fusion proteins. The site-specific mutants of p60Δ8 were generated as described below. All deletion mutants bind p60TRAK activity. The shaded region indicates the death domain. FIG. 1B shows a SDS-polyacrylamide gel stained with Coomassie Blue of the GST fusion is shown with the indicated molecular mass standards. All fusion proteins were expressed and purified as described below.

FIG. 16 shows the sequence homology between cyclins and the p60 cytoplasmic domain. An optimized sequence alignment of the cytoplasmic domain of the p60 TNF receptor (residues 292–400) with the cyclin box conserved among most cyclin family members is shown. The sequence alignment of human cyclins A, B, D$_1$, E, C, and H was essentially as described (Jeffrey et al., 1995). Cyclins B, D$_1$, and E share 50%, 40%, and 40% homology with cyclin A, respectively (Hadwiger et al., 1989). The p60 cytoplasmic domain shares 31% (33 of 108 residues) and 50% (54 of 108 residues) homology with cyclin A and all cyclins, respectively. Homologous amino acids (boxed) were identified as follows: L, V, I, M; D, E; N, Q; K, H, R; A, G; Y, W, F; P; C; S, T. Lower-case letters indicate gaps in the sequence alignment. The secondary structure elements (a-helices 1–5) of cyclin A from the cyclin A-cdk2 crystal structure are as indicated (Jeffrey et al., 1995). Numbers above amino acids indicate important residues necessary for tight packing of the alpha helices.

FIG. 17A shows that the GST-p60Δ8 binds to endogenous cdk2. U937 cells lysates (15×10⁶/assay) were prepared and affinity precipitated with the indicated fusion protein as described below. Whole cell extracts were prepared from 2×10⁶ U937 cells by boiling the cells in 100 μl of SDS-sample buffer. Proteins were resolved by 8.5% SDS-polyacrylamide gel electrophoresis, transferred to PVDF membrane, and probed with the indicated antibodies. The mock reaction contains GST-p60Δ8 without U937 cell lysates. FIG. 17B shows that $^{35}$S-labeled cdk2 binds to GST-p60Δ8. A volume (10 μl) of $^{35}$S-labeled cdc2 (top) or cdk2 (bottom) was mixed with glutathione agarose, or GST fusion proteins bound to glutathione agarose, or p13$^{suc1}$-agarose as indicated and processed as described below. The samples were subjected to 8.5% SDS-polyacrylamide gel electrophoresis and analyzed by a PhosphorImager. Ten percent of total $^{35}$S-labeled protein (10% input) added to each binding reaction was loaded as a standard. FIG. 17C shows that TNF stimulates the association of cdk2 with the p60 TNF receptor. The conditions utilized for this experiment were similar to those previously described (Dyson et al., 1989). Briefly, U937 cells were either treated without or with 0.1 nM TNF for 5 minutes. Cell lysates were prepared, and a volume (20 μl) of $^{35}$S-labeled cdk2 was added to the cell lysates. The cell lysates were immunoprecipitated with protein A/G sepharose beads (beads), preimmune serum (PIS), affinity purified anti-p60CD antibodies, or anti-cdk2 antibodies. Precipitates bound to protein A/G sepharose beads were collected by centrifugation and washed four times in lysis buffer and one time in kinase buffer. The samples were subjected to 8.5% SDS-polyacrylamide gel electrophoresis and analyzed by a PhosphorImager and ImageQuant software.

FIG. 18A shows that Cdc2 and cdk2, but not cdk4, binds to p13$^{suc1}$. U937 cells (4×10$^6$) were lysed and precipitated with p13$^{suc1}$ agarose. Beads were collected by centrifugation, washed with lysis buffer, and boiled in the presence of SDS-sample buffer. Whole cell extracts (wce) were prepared as described in FIG. 17A. A volume (2 μl) of the boiled whole cell extracts (wce) (lanes 1, 3, and 5) and an equal volume of p13$^{suc1}$-agarose precipitates (lanes 2, 4, and 6) were subjected to 8.5% SDS-polyacrylamide gel electrophoresis and transferred to a PVDF membrane by electrophoresis. The membrane was cut into three identical pieces and western blotting was performed using antibodies to cdc2, cdk2, and cdk4. Immunoreactive bands were detected using horseradish peroxidase-conjugated secondary antibodies and the Enhanced Chemiluminescence system (ECL). Longer exposure of the cdk4 blot to film did not show any cdk4 bound to p13$^{suc1}$. FIG. 18B shows that p13$^{suc1}$-agarose depletes p60TRAK activity associated with GST-p60Δ15. Equal amounts of U937 cell lysates were incubated with 25 μg of either GST bound to glutathione agarose (−) or p13$^{suc1}$-agarose (+) for 1 hour at 4° C. with shaking. The beads were collected by centrifugation, and the supernatant was once more centrifuged. An equal volume of the supernatant was affinity precipitated with GST-p60Δ15. The precipitates were washed extensively, and in vitro kinase assays with histone H1 (5 μg) were performed as described below. Proteins were separated by 8% SDS-polyacrylamide gel electrophoresis and analyzed by a PhosphorImager and ImageQuant software. The asterisk indicates a degradation product of GST-p60Δ5. Phosphorylation of GST-p60Δ15 by p60TRAK causes hyperphosphorylation of the fusion protein. FIG. 18C shows that Rb$^{110}$ phosphorylation by p60TRAK is decreased by depletion with p13$^{suc1}$-agarose. Equal amounts of U937 cell lysates were incubated with either GST bound to glutathione agarose (−) or p13$^{suc1}$-agarose (+) for 1 hour at 4° C. with shaking. The beads were collected by centrifugation, and the supernatant was once more centrifuged. An equal volume of the supernatant was affinity precipitated with either GST-p60Δ8 or GST-p60Δ15. The precipitates were washed extensively, and in vitro kinase assays with Rb$^{110}$ (0.2 μg) were performed as described below. Proteins were separated by 8% SDS-polyacrylamide gel electrophoresis and analyzed by a PhosphorImager and ImageQuant software.

FIG. 19A shows that pervanadate inhibits the activity of p60TRAK. U937 cells were incubated with the indicated concentration of pervanadate for 30 minutes at 37° C. Cells lysates were prepared as described below and used for affinity precipitations with ~5 μg of GST, GST-p60Δ8, or GST-p60Δ12 bound to glutathione agarose. The precipitations were washed extensively, and in vitro kinase assays were performed as described below. The samples were analyzed by 9% SDS-polyacrylamide gel electrophoresis, and the dried gel exposed to X-ray film for 8 hours at −70° C. The arrows indicate the migration of the GST fusion proteins, and the molecular mass standards are indicated in kDa. FIG. 19B shows that pp37 contains only phosphotyrosine. U937 cells were incubated with 100 μM pervanadate for 30 minutes at 37° C. Cell lysates were affinity precipitated with GST-p60Δ8, and an in vitro kinase assay performed as described below. The sample was subjected to SDS-polyacrylamide gel electrophoresis and transferred to a PVDF membrane. The radioactive band corresponding to pp37 was excised from the membrane and a phosphoamino acid analysis was performed as described below. FIG. 19C shows that the amino acid sequence of the p60 cytoplasmic domain differs between p60Δ8 and p60Δ2. The underlined sequence is a consensus phosphorylation site (GT$^{14}$Y$^{15}$GVV) for the human WEE1 tyrosine kinase found in cyclin-dependent kinases (Nigg, 1995). FIG. 19D shows that in pervanadate-treated cells, Y$^{331}$ undergoes phosphorylation by a tyrosine kinase that associates with GST-p60Δ8. U937 cells were incubated in the presence or absence of 100 μM pervanadate for 30 minutes at 37° C. Cell lysates were prepared and affinity precipitations were performed with the indicated wild type or mutant GST fusion protein as described below. In vitro kinase assays were conducted, and the samples analyzed by 8.5% SDS-polyacrylamide gel electrophoresis, and the dried gel was exposed to X-ray film for 3 hr at −70° C. The relative mobility of GST-p60Δ8, its site-directed mutants, and pp37 is indicated by the arrows. FIG. 19E shows that p49$^{WEE1}$ phosphorylates Y$^{331}$ of the p60 cytoplasmic domain in vitro. In vitro kinase assays with a volume (2 μl, lanes 1, 3, 5, 7; or 10 μl, lanes 2, 4, 6, 8) of purified p49$^{WEE1}$ and with the substrates GST (lanes 1 and 2), GST-p60Δ8 (lanes 3 and 4), GST-p60Δ8$^{T329A}$ (lanes 5 and 6), or GST-p60Δ8$^{Y331F}$ (lanes 7 and 8) was performed as described below. The proteins were resolved by 8.5% SDS-polyacrylamide gel electrophoresis, and the dried gel was analyzed by a PhosphorImager. FIG. 19F shows that GST-cdc25 dephosphorylates GST-p60Δ8 that was phosphorylated by p49$^{WEE1}$. GST-p60Δ8 was phosphorylated by p49$^{WEE1}$ in duplicate as described in FIG. 19E. The kinase assays were stopped with a kinase stop buffer and washed two times with phosphatase buffer. Purified GST-cdc25 was added to one of the reaction mixtures (lane 2), and the reaction was allowed to proceed for 20 minutes at 37° C. The proteins were resolved by 8.5% SDS-polyacrylamide gel electrophoresis, and the dried gel was analyzed by a PhosphorImager.

FIG. 20 shows the p49$^{WEE1}$ Inhibits p60TRAK Activity. FIG. 20A shows that exogenous p49$^{WEE1}$ inhibits histone kinase activity of p60TRAK. U937 cells were incubated with media, pervanadate, or okadaic acid in triplicate as indicated for 30 minutes at 37° C. Cell lysates were prepared and affinity precipitated with GST-p60Δ8. The precipitated p60TRAK was washed three times with lysis buffer and three times with kinase buffer. A kinase assay was performed in the presence (lanes 2, 3, 5, 6, 8, and 9) or absence (lanes 1, 4, and 7) of unlabeled Mg-ATP and in the presence (lanes 2, 5, and 8) of purified p49$^{WEE1}$ for 20 minutes at room temperature. Following the cold kinase assay, the reaction mixtures were washed two times in lysis buffer and two times in kinase buffer prior to in vitro kinase assays with 5 μg histone type VIs and [$^{32}$P]ATP as described below. Samples were analyzed by a 12% SDS-polyacrylamide gel electrophoresis and a PhosphorImager. Quantitation of radioactivity incorporated into histone was estimated by ImageQuant software. FIG. 20B shows that histone H1 kinase activity immunoprecipitated with anti-cdk2 antibodies is inhibited in pervanadate-treated cells. U937 cells were incubated in the presence or absence of 100 μM pervanadate for 30 minutes at 37° C. Cell lysates were prepared and immunoprecipitated with an affinity-purified polyclonal antibody against cdk2 as described below. Histone kinase assays were performed, and the samples analyzed by 8.5% SDS-polyacrylamide gel electrophoresis and a PhosphorImager. Quantitation of radioactivity incorporated into histone was estimated by ImageQuant software.

FIG. 21 shows the okadaic acid increases the activity of p60TRAK. FIG. 21A shows that okadaic acid treatment of U937 cells increases p60TRAK activity. U937 cells were incubated with the indicated concentration of okadaic acid for 30 minutes at 37° C. The cells were processed as described in FIG. 17A. FIG. 21B shows that p60TRAK activity is positively regulated by serine/threonine phosphorylation. U937 cells were incubated in the absence or presence of 0.6 μM okadaic acid for 30 minutes at 37° C. Cell lysates were prepared and used for affinity precipitation of p60TRAK by GST-p60Δ8 in six identical tubes. The precipitated p60TRAK was washed with lysis buffer and then phosphatase buffer. In separate tubes, cell extracts from 5×10$^6$ U937 cells were lysed in the presence or absence of protein phosphatase inhibitors (10 mM NaF, 2 mM orthovanadate, 0.6 μM okadaic acid) (PPi). An amount (10 μl) of these extracts were added to the precipitated p60TRAK as indicated and incubated at room temperature for 20 minutes. The precipitated p60TRAK was washed with lysis buffer and kinase buffer. In vitro kinase assays were performed and the samples analyzed by 8.5% SDS-polyacrylamide gel electrophoresis and a PhosphorImager.

FIG. 22 shows the pervanadate inhibits TNF-dependent activation of NF-kB. Nuclear extracts were prepared from U937 cells pretreated with the indicated concentration of pervanadate for 30 minutes and stimulated in the absence (−) or presence (+) of 0.1 nM TNF for 5 minutes. An amount (2 μg) of the nuclear extracts was incubated with a radiolabled double-stranded oligonucleotide containing a wild-type (lanes 1–12, 14) or mutant (lane 13) NB DNA binding by electrophoretic mobility shift assay. For cold competition assays, DNA binding reactions were performed in the presence of a 100-fold excess of unlabeled wild-type (lane 12) or mutant (lane 14) NF-kB binding site. Nuclear extracts were omitted from lane 1.

FIG. 23 shows a model for the regulation of p60TRAK by tyrosine and serine/threonine phosphorylation. The active kinase complex is shown in the middle. Pervanadate inhibits tyrosine dephosphorylation of p60TRAK, generating an inactive p60TRAK complex (right) that is a substrate for the human WEE1 kinase. Dephosphorylation of p60TRAK on serine/threonine residues shifts p60TRAK to an inactive state (left). Okadaic acid prevents the serine/threonine dephosphorylation of p60TRAK, allowing for the active p60TRAK complex (middle).

DETAILED DESCRIPTION OF THE INVENTION

Figure 1:
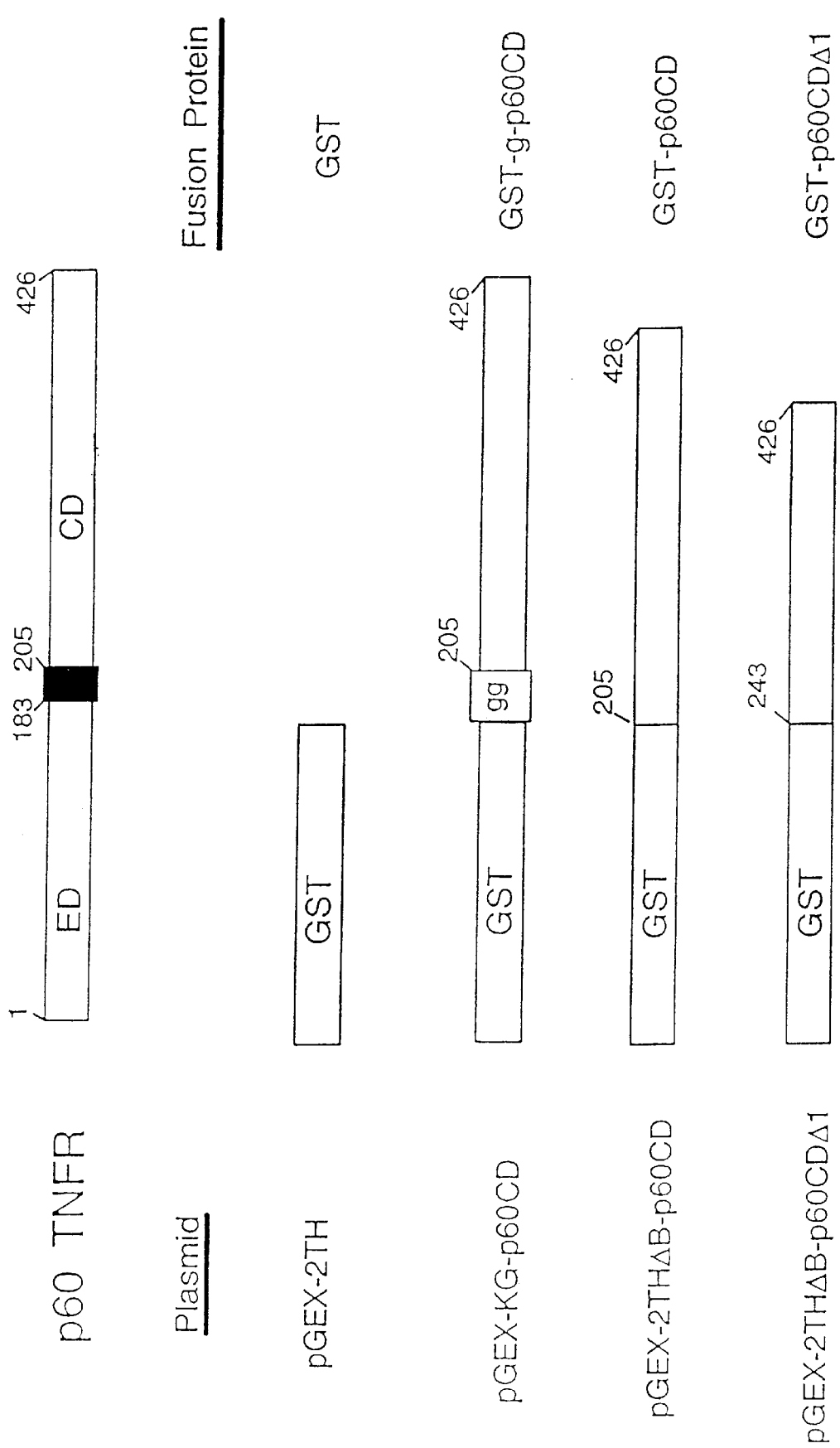
FIG. 1 shows a schematic diagram of GST fusion proteins containing the cytoplasmic domain of the p60 form of the tumor necrosis factor receptor. The full-length p60 TNF receptor is shown with the extracellular domain (ED), the transmembrane region (shaded), and the cytoplasmic domain (CD). Residue numbering is based on the mature form of the receptor. Plasmids (left) and the fusion proteins (right) expressed from them are indicated. GST-p60CDΔ1 was used entirely. gg designates the glycine linker in the fusion protein GST-g-p60CD.

The following abbreviations are used in the instant specification: TNF: tumor necrosis factor; NGF: nerve growth factor; NF-κB: nuclear factor kappa B; IκB-α: inhibitory subunit of NF-κB; FBS: fetal bovine serum; PCR: polymerase chain reaction; MBP: myelin basic protein; GST: glutathione-S-transferase; CD: cytoplasmic domain; PMSF: phenylmethylsulfonyl fluoride; SDS: sodium dodecyl sulfate; PAGE: polyacrylamide gel electrophoresis; PVDF: polyvinylidene difluoride; TLC: thin layer chromatography; p60TRAK: tumor necrosis factor receptor-associated kinase; and p60TRAP: tumor necrosis factor receptor-associated protein.

The present invention is directed to an isolated and purified protein that associates with the cytoplasmic domain of the p60 form of the tumor necrosis factor receptor, having a molecular weight of about 52–55 kDa as determined by SDS-PAGE, is a phosphoprotein, and does not bind to the p80 form of the tumor necrosis factor receptor. This novel tumor necrosis factor receptor associated protein (p60TRAP) is a phosphoprotein that is phosphorylated at serine and threonine residues. The TRAP exhibits optimal phosphorylation in the presence of $Mn^{2+}$ or $Mg^{2+}$.

The present invention is also directed to an isolated and purified protein kinase that binds to the cytoplasmic domain of the p60 form of the tumor necrosis factor receptor, said kinase phosphorylates the p60 form of the tumor necrosis factor receptor.

This tumor necrosis factor receptor associated kinase (p60TRAK) phosphorylates the p60 form of the tumor necrosis factor receptor at serine and threonine residues. The p60TRAK exhibits optimal phosphorylation in the presence of $Mn^{2+}$. The p60TRAK of the present invention is rapidly inducible by tumor necrosis factor. In addition to phosphorylating the p60 form of the tumor necrosis factor receptor at serine and threonine residues, the p60TRAK also phosphorylates casein, histone H1 and MBP.

As shown herein below, the p60TRAK of the present invention binds to the acidic rich-carboxy terminal of the cytoplasmic domain of the p60 form of the tumor necrosis factor receptor. More specifically, the p60TRAK binds to a region within amino acids 324–426 of the p60 form of the tumor necrosis factor receptor. Most preferably, the protein kinasebinds to a region within amino acids 397–426 of the p60 form of the tumor necrosis factor receptor.

It is specifically contemplated that pharmaceutical compositions may be prepared using inhibitors of the novel p60TRAP or p60TRAK of the present invention. A person having ordinary skill in this art would readily be able to determine, without undue experimentation, the appropriate dosages and routes of administration of the pharmaceutical composition of the present invention. Accordingly, the present invention also provides a pharmaceutical composition comprising a competitive inhibitor of the kinase of claim 4 and a pharmaceutically acceptable carrier.

The present invention is also directed to a method of decreasing the biological effects of tumor necrosis factor comprising the step of inhibiting the phosphorylation of the p60TRAP. In this method, the p60TRAP is inhibited by administering a pharmacologically effective dose of the pharmaceutical composition of the present invention.

The present invention also includes a method of decreasing the biological effects of tumor necrosis factor comprising the step of inhibiting the p60TRAK of the present invention. In addition, the present invention encompasses a method of reducing the cytotoxic effects of tumor necrosis factor comprising the step of inhibiting the p60TRAK of the present invention.

In another embodiment, the present invention provides a method of treating a pathophysiological state characterized by an undesirable physiological level of tumor necrosis factor comprising the step of administering a pharmacologically effective dose of the pharmaceutical composition of the present invention to a human.

Generally, the pathophysiological state treated by the methods of the present invention is any state or condition in which inhibition of the biological effects of tumor necrosis factor is desirable. Accordingly, the pathophysiological states treated may be ones in which the physiological concentrations of TNF and consequently, the biological effects, are undesirably high. Alternatively, the methods of the present invention may be used to treat pathophysiological state where the level of TNF is "normal" but a reduction or inhibition of the physiological effects of TNF is therapeutically desirable. A possible example of the latter condition would be where physiological levels of TNF are normal but elevated levels of TNF receptors exist in particular tissue(s).

Preferably, the pathophysiological state is selected from the group consisting of neoplastic disease, human immunodeficiency disease, sepsis, cachexia, graft vs host disease, autoimmune disease, cerebral malaria and capillary leak syndrome. Representative examples of neoplastic disease include leukemia, ovarian carcinoma, renal cell carcinoma, breast adenocarcinoma and glioblastoma. Representative examples of autoimmune disease include systemic lupus erythematosus, rheumatoid arthritis and multiple sclerosis.

In another embodiment, the present invention is directed to a method of treating a neuro-oncologic state, comprising administering to a human a pharmacologically effective dose of the pharmaceutical composition of the present invention. Preferably, the neuro-oncologic state is glioblastoma, an astrocytoma or a meningioma. Also provided by the present invention is a method of treating renal cancer comprising administering to a human a pharmacologically effective dose of the pharmaceutical composition of the present invention.

The level of ordinary skill of the average scientist in the area of molecular cell biology has increased substantially in recent years. A person having ordinary skill in this art would readily be able to sequence the phosphoprotein and protein kinase of the present invention, given the teachings herein, especially the teachings of the purification of p60TRAP and p60TRAK.

With knowledge of the teachings of the present invention, a person having ordinary skill in this art would readily be able to prepare specific competitive inhibitors of the protein kinase of the present invention. That is, a person having ordinary skill in this area of research would be readily able to localize the phosphorylation site on the substrate phosphorylated by the kinase and subsequently use this knowledge to develop competitive inhibitors of the kinase.

The following examples are given for the purpose of illustrating various embodiments of the invention and are not meant to limit the present invention in any fashion.

EXAMPLE 1
Materials

Human TNF ($5\times10^7$ units/mg) was obtained from Genentech (South San Francisco, Calif.). Purchased reagents included the following: glutathione, glutathione-agarose, phosphotyrosine, phosphoserine, phosphothreonine, phenylmethyl sulfonyl fluoride (PMSF), leupeptin, ninhydrin, myelin basic protein (MBP), casein, histone H1, histone H2B, ponceau S, and aprotinin (Sigma); restriction enzymes and Taq DNA polymerase (Promega); prestained and low molecular weight markers, Coomassie Brilliant Blue R-250, and sodium dodecyl sulfate (SDS) (Bio-Rad); PVDF membranes (Millipore); Trans-[$^{35}$S] label (1000 Ci/mmol), [$\gamma$-$^{32}$P]ATP (7000 Ci/mmol), and carrier-free[$^{32}$P$_i$] (500 mCi/ml) (ICN); RPMI-1640 (BioWhittaker); fetal bovine serum, methionine and cysteine, and phosphate-free RPMI-1640 (GIBCO-BRL); tryptone and yeast extract (DIFCO); Geneclean (PGC Scientifics); isopropyl-$\beta$-thiogalactoside (IPTG) (USB); and ethyl reversed phase KC2 thin-layer chromatography (TLC) plates (Whatman). All other reagents were reagent grade or higher.

EXAMPLE 2
Cells and plasmids

The histiocytic lymphoma U-937 (CRL 1593) and breast adenocarcinoma MCF-7 (HTB 22) cell lines were obtained from the ATCC. Human foreskin fibroblasts were obtained from Dr. Olivia M. Pereira-Smith (Baylor College of Medicine, Houston, Tex.). Cells were grown in RPMI-1640 supplemented with 10% fetal bovine serum and 100 $\mu$g/ml streptomycin at 37° C. in 5% $CO_2$ incubator. *Escherichia coli* strain BL21 and plasmids pGEX-2T and pGEX-KG were from Dr. V. W. Rodwell (Purdue University, W. Lafayette, Ind.). *E. coli* strain NM522 and plasmid pGEX-2TH were from Dr. H. Saya (M. D. Anderson Cancer Center, Houston, Tex.). The plasmid containing the entire coding sequence of p60 (pCMVXVBpL4-p60) was from Dr. T. Kohno (Synergen, Boulder, Colo.).

EXAMPLE 3
Construction of Glutathione-S-Transferase (GST) Expression Vectors DNA manipulations were carried out as described by Sambrook et al., (1989) *Molecular cloning: A Laboratory Manual,* 2nd ed., Cold Spring Harbor Laboratory Press, Cold Spring Harbor, N.Y. Polymerase chain reaction (PCR) and specific 5' and 3' primers with unique restriction sites were used to amplify the cytoplasmic domain of p60 from pCMVXVBpL4-p60 for insertion into the GST fusion vectors. The PCR primers were:

5'-CTAAGAGAATTCGCTACCAACGGTGGAAGTCC-3' (SEQ.ID.NO.14) and
5'-GACGTACTCGAGTCATCTGAGAAGACT-3' (SEQ.ID.NO.15)

and were used to amplify a 671-bp fragment that encodes residues Y207 to R426 of p60. The PCR fragment was digested with EcoRI and XhoI and ligated into EcoRI/XhoI-digested pGEX-KG to give rise to pGEX-KG-p60CD. The pGEX-KG-p60CD was digested with EcoRI and partially digested with HindIII, and both the 700-bp (EcoRI/HindIII fragment) and the 570-bp (HindIII/HindIII due to an internal HindIII site in the p60 gene) fragments were isolated. The 700-bp EcoRI/HindIII fragment was inserted into EcoRI/HindIII-digested pGEX-2TH and termed pGEX-2TH-p60CD. In order to place the p60CD coding sequence in frame with GST, pGEX-2TH-p60CD was further digested with BamHI, filled in with Klenow, and religated to give rise to pGEX-2THAB-p60CD. Additionally, the 570-bp HindIII/HindIII fragment was inserted into HindIII-digested pGEX-2THAB to give pGEX-2THAB-p60CD$\Delta$1.

Construction of the plasmid encoding GST-p80CD was as follows: all subsequent DNA manipulations were carried out as described by Sambrook et al. Molecular Cloning: A Laboratory Manual, 2nd ed., Cold Spring Harbor Laboratory Press, Cold Spring Harbor, N.Y. PCR and the primers 5'CTAAGAGGATCCAAAAAGAAGCCCTTGTGCCTG-3' and 5'TCTTAGAAGCTTTTAACTGGGCTTCATCCCAGC-3' with unique restriction sites were used to amplify a 546-bp fragment from pCMVXVBpL4p80 for insertion into pGEX-2TH. This construct, pGEX-2TH-p80CD, expresses a fusion protein (GST-p80CD) with the p80 cytoplasmic domain (K266-S439) linked to GST. Expression of GST-p80CD in BL21 cells and purification were carried out as follows: BL21 cells harboring the expression plasmid were induced with 0.5 mM IPTG at 37° C. for one hour. Cells were collected by centrifugation and lysed in Buffer A (20 mM Tris, pH 8.0, 200 mM NaCl, 10% glycerol, 0.5% NP-40, 1 mM PMSF, 2 μg/ml aprotinin, 2 μg/ml leupeptin, 0.1% 2-mercaptoethanol) containing 5 mg lysozyme and briefly sonicated. The lysate was cleared by centrifugation at 30,000 rpm and the supernatant passed once through a 1.2 ml column of 50% (v/v) glutathione-agarose. The column was subsequently washed with 20 ml Buffer A, 10 ml of 1M NaCl in Buffer A and 20 ml Buffer A. The protein was stored at 4° C. on glutathione-agarose beads as a 50% slurry in Buffer A (20 mM Tris, pH 8.0, 200 mM NaCl, 10% glycerol, 0.5% NP-40, 1 mM PMSF, 2 μg/ml aprotinin, 2 μg/ml leupeptin, and 0.1% 2-mercaptoethanol. The amount of fusion protein was estimated by Coomassie Blue staining of SDS-PAGE.

Figure 6:
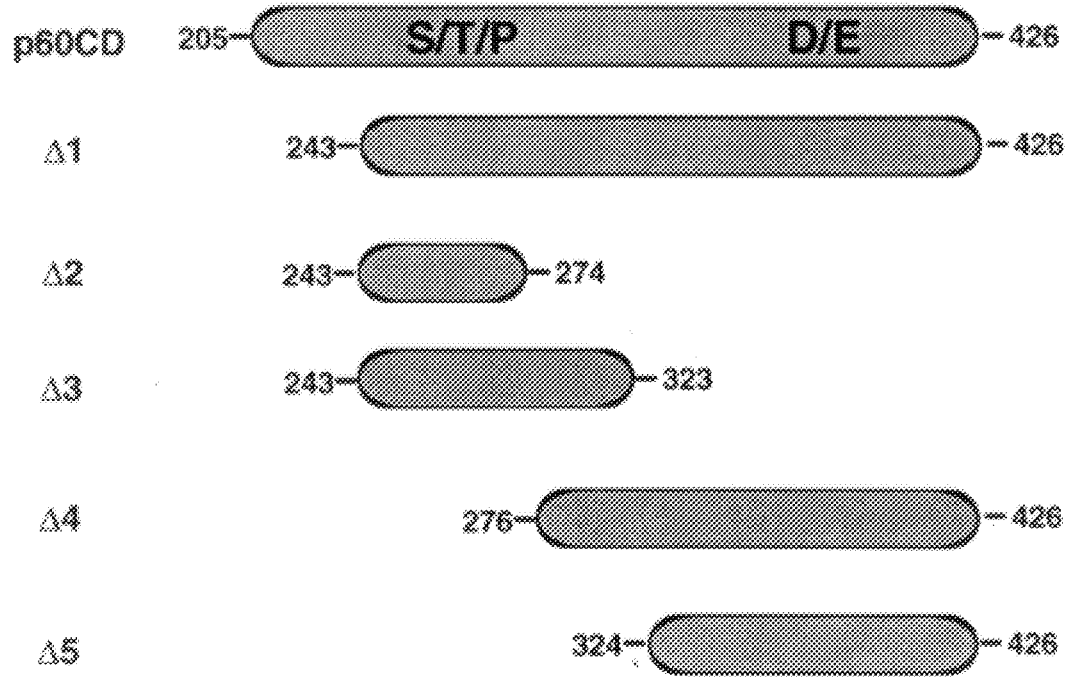
FIG. 6 shows a schematic diagram of the deletion mutants of the cytoplasmic domain of the p60 TNF receptor.
Figure 6:
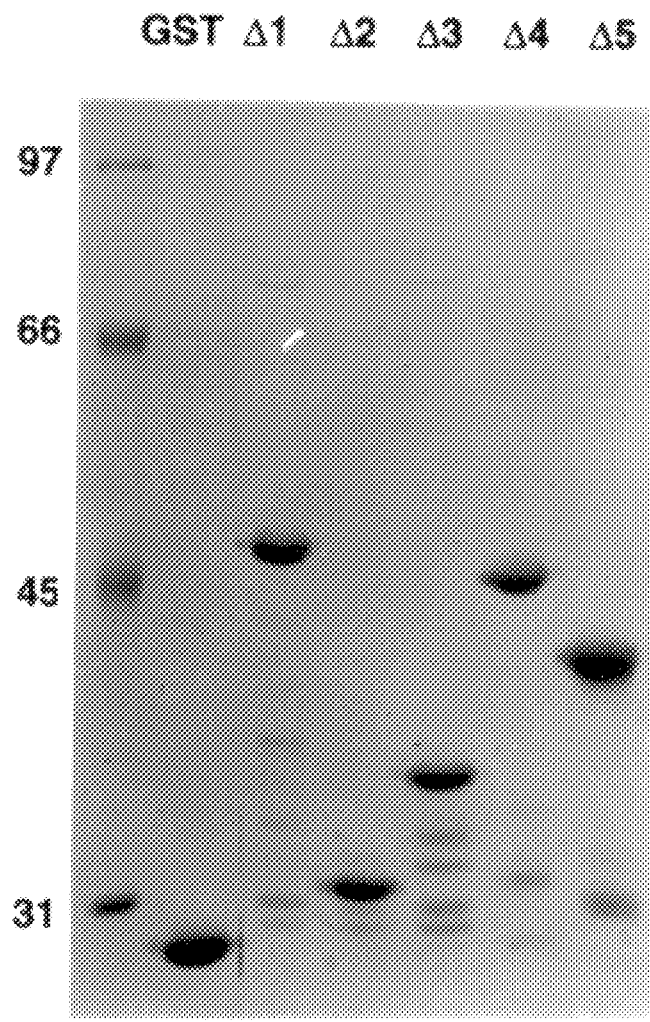

FIG. 6 illustrates the fusion proteins that were made for this study. The construction of the plasmid encoding GST-p60 deletion mutants was as follows: The 5'-primers: CTAAGAGAATTCAGCTTCAGTCCCACT (SEQ.ID.NO.3) (Δ2, Δ3); CTAAGAGAATTC-CCCAACTTTGCGGCT (SEQ.ID.NO.4) (Δ4); and CTAA-GAGAATTCACTGATGACCCCGCG (SEQ.ID.NO.5) (Δ5); and the 3'-primers: TCTTAGTTAAGCTTAATCAGT-CACCGGGGGTATA (SEQ.ID.NO.6) (Δ2); TCTTAGT-TAAGCTTAATCAGTCTAGGCTCTGTGG (SEQ.ID.NO.7) (Δ3); and TCTTAGTTAAGCTTAAT-CATCTGAGAAGACT (SEQ.ID.NO.7) (Δ4, Δ5) were used to amplify fragments by PCR with unique restriction sites from pCMVXVBpL4-p60 of 0.10 kb (Δ2), 0.25 kb (Δ3), 0.46 kb (Δ4), and 0.31 kb (Δ5). The PCR products were digested with EcoRI/HindIII and inserted into digested pGEX-2TH to yield the expression vectors. Expression and purification of the GST fusion proteins from BL21 cells were carried out as described below. The amount of fusion protein was estimated by SDS-PAGE and also by staining with Coomassie Blue.

EXAMPLE 4

Expression and Purification of GST Fusion Proteins

The expression and purification of GST-p60CDΔ1 was carried out as previously described by Guan and Dixon, Anal. Biochem. 192:262–267 (1991) with the following exceptions to minimize degradation. Briefly, BL21 cells harboring the expression plasmid were induced with 0.5 mM IPTG at 15° C. for one hour. Cells were collected by centrifugation and lysed in Buffer A (20 mM Tris, pH 8.0, 200 mM NaCl, 10% glycerol, 0.5% NP-40, 1 mM PMSF, 2 μg/ml aprotinin, 2 μg/ml leupeptin, 0.1% 2-mercaptoethanol) containing 5 mg lysozyme and briefly sonicated. The lysate was cleared by centrifugation at 30,000 rpm, and the supernatant passed once through a 1.2 ml column of 50% (v/v) glutathione-agarose. The 1 0 column was subsequently washed with 20 ml Buffer A, 10 ml of 1M NaCl in Buffer A, and 20 ml Buffer A, and stored at 4° C. as a 50% slurry in Buffer A. The amount of fusion protein was estimated by SDS-PAGE and staining the gel with Coomassie Blue.

EXAMPLE 5

In Vitro Binding of GST Fusion Protein to Cell Extracts

Cells were plated at $0.5 \times 10^6$/ml in serum-free medium for 18–24 hours. Cells were either left untreated or treated with 5 nM TNF for the indicated periods of time and lysed in 1 ml of lysis buffer (20 mM Tris, pH 7.7, 0.5% NP-40, 200 mM NaCl, 50 mM NaF, 0.2 mM sodium orthovanadate, 1 mM PMSF, 2 μg/ml aprotinin, 2 μg/ml leupeptin, 0.1% 2-mercaptoethanol) on ice for 10 minutes followed by a 10 minute centrifugation. The supernatant was precleared with 25 μg GST and 40 μl 50% (v/v) glutathione-agarose for 2–12 hours at 4° C. The precleared supernatant was mixed with approximately 5–10 μg GST-p60CDΔ1 attached to GSH-agarose for 2 hours at 4° C. The beads were collected by centrifugation and washed extensively with lysis buffer (4×500 μl) and with kinase buffer (3×500 μl) (20 mM HEPES, pH 7.4, 10 mM NaF, 0.2 mM sodium orthovanadate, 0.1% 2-mercaptoethanol). The pellets were then used for in vitro kinase assays. Where indicated, protein was measured by the method of Bradford.

EXAMPLE 6

In Vitro Kinase Assays

Standard kinase assays were carried out for 10 minutes at 37° C. in 50 μl containing 20 mM HEPES, pH 7.4, 10 mM MgCl$_2$, 10 mM MnCl$_2$, 0.2 mM ATP, 0.2 mM NaF, 0.1 mM sodium orthovanadate, and 10 μCi [γ-$^{32}$P]ATP or as described above. Reactions were stopped with 15 μl SDS-sample buffer, boiled for 5 minutes, and then subjected to SDS-PAGE. Protein bands were visualized by staining with Coomassie Blue and the dried gel was analyzed by a Phosphorimager. Labeled protein bands were quantified using ImageQuant Software (Molecular Dynamics, Sunnyvale, Calif.).

EXAMPLE 7

Phosphoamino Acid Analysis

Samples subjected to in vitro kinase assays were separated by SDS-PAGE, transferred to PVDF membranes by electrophoresis, and stained with ponceau S. Protein bands were excised, boiled with 6N HCl for 1 hour, dried by speed vacuum, and analyzed by TLC in buffer containing 80% methanol, 1.5% acetic acid, and 0.5% formic acid. Subsequently, the dried TLC plate was analyzed by a Phosphorimager. Migration of standards was visualized by spraying the dried TLC plate with ninhydrin.

EXAMPLE 8

Expression of the Cytoplasmic Domain of p60 as a Fusion Protein

Three different constructs, pGEX-KG-p60CD, pGEX-2THΔB-p60CD, and pGEX-2THΔB-p60CDΔ1, were used to express the cytoplasmic domain of the p60 form of the tumor necrosis factor receptor as a GST fusion protein (FIG. 1). Constructs pGEX-KG-p60CD and pGEX-2THΔB-p60CD yielded fusion proteins that were rapidly degraded in vivo. Construct pGEX-2THΔB-p60CDΔ1 with a deletion of the nucelotides encoding 39 residues proximal to the transmembrane region of the p60 form of the tumor necrosis factor receptor, minimized the degradation of the fusion protein.

EXAMPLE 9

A Specific Protein from U-937 Cells Associates with p60CDΔ1

Figure 2:
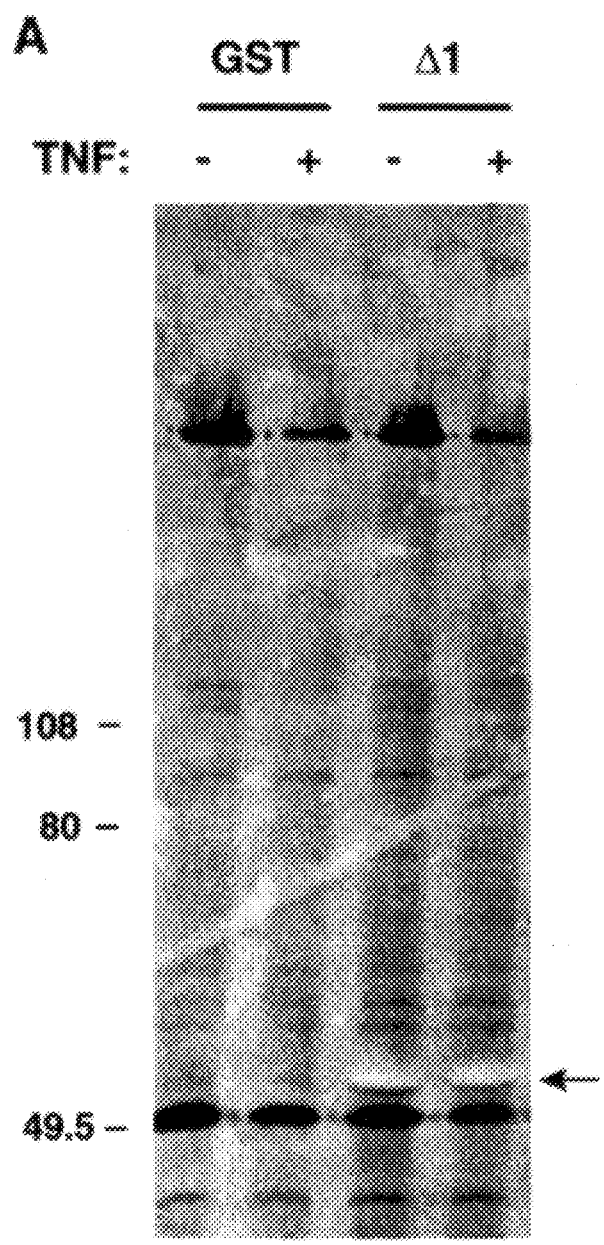
FIG. 2 shows the association of proteins to GST-p60CDΔ1 from $^{35}$S-labeled (FIG. 2A) and $^{32}$P-labeled (FIG. 2B) U-937 cells.
Figure 2:
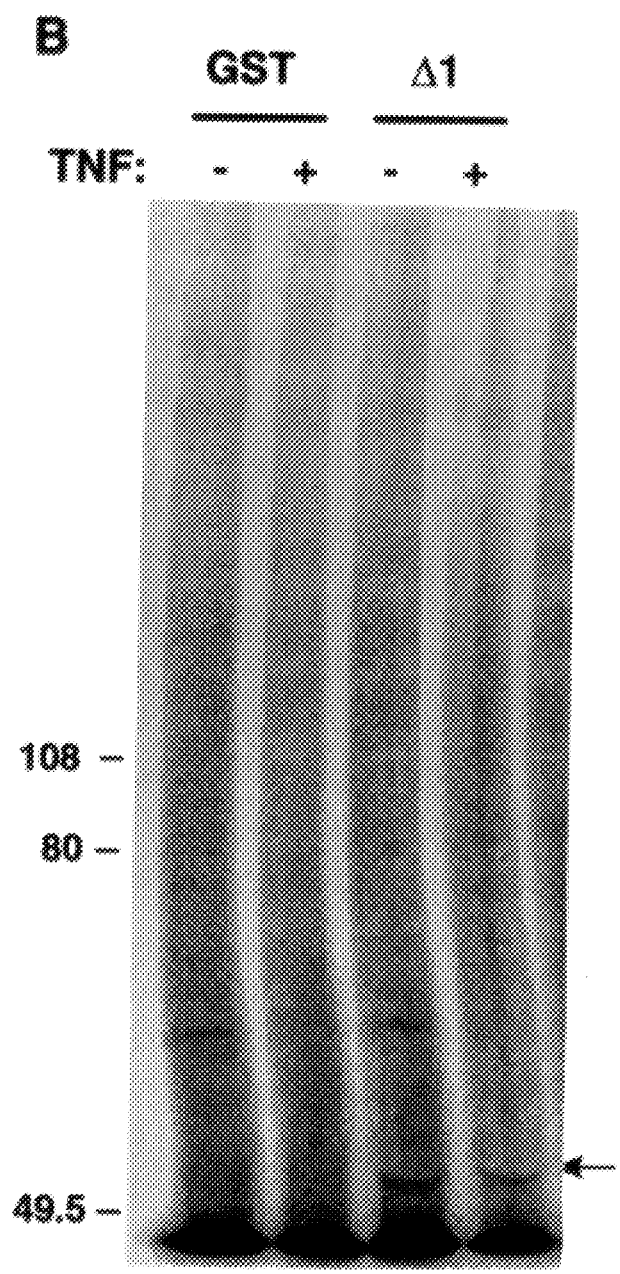

A protein in $^{35}$S-labeled cells was found to associate specifically with GST-p60CDΔ1 and not with GST (FIG. 2A). This protein was detected whether or not the cells were treated with TNF, and in more than six separate studies. The molecular mass of the tumor necrosis factor receptor-associated protein was estimated to be 52 ±3 kDa and is termed herein p60TRAP.

To show that phosphoproteins bound to GST-p60CDΔ1, U937 cells with $^{32}P_i$ were labeled which identified a phosphoprotein of approximately 52 kDa (pp52) that could bind to GST-p60CDΔ1 from cells whether or not they were treated with TNF (FIG. 2B). Phosphoamino acid analysis of pp52 indicated that phosphorylation occurred on both threonine and serine residues. Thus, the p52 identified by $^{35}$S-labeling is a phosphoprotein.

EXAMPLE 10

A Kinase from U-937 Cell Lysate Binds and Phosphorylates p60CDΔ1

The cytoplasmic domain of p60 does not contain a domain homologous to any known kinase nor does it exhibit any intrinsic kinase activity. In vitro kinase assays indicated that p60CDΔ1 served as a substrate for several highly purified protein kinases, i.e., that phosphorylation sites exist within the cytoplasmic domain of the p60 form of the tumor necrosis factor receptor.

Figure 3:
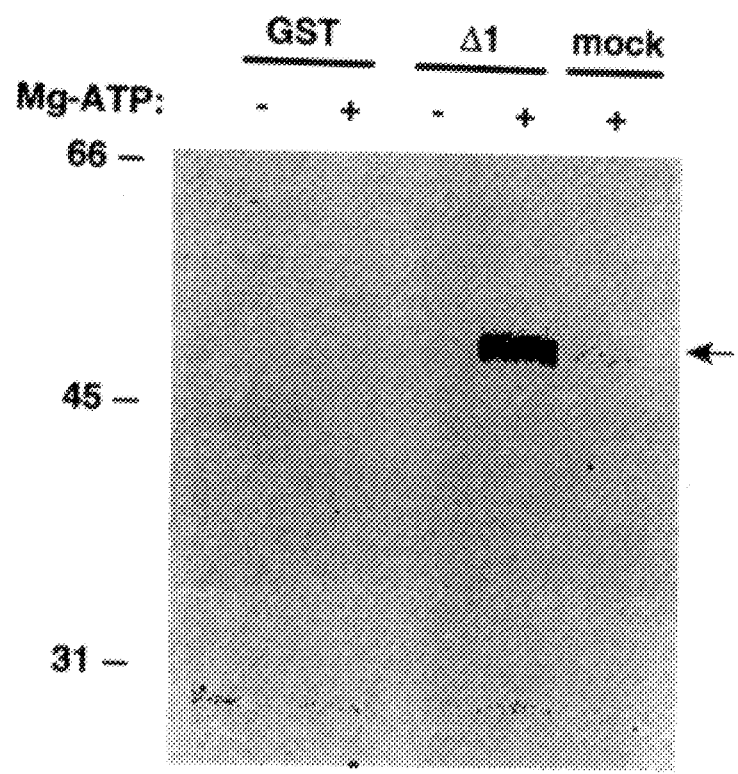
FIG. 3 shows that kinase activity from U-937 cell lysate associates with GST-p60CDΔ1 and phosphorylates it. Cells ($0.5 \times 10^6$) were lysed and in vitro binding to 5 µg of either GST or GST-p60CDΔ1 was carried out as described below. In vitro kinase reactions were incubated in the absence (−) or presence (+) of Mg-ATP for 10 minutes at 37° C. In mock reaction, no cell extract was added. Proteins were subjected to 10% SDS-PAGE and visualized by staining with Coomassie Blue. The dried gel was analyzed by a Phosphorimager.

After in vitro binding assays with U-937 cell lysate, the adsorbed proteins were subjected to an in vitro kinase assay. Minimal kinase activity was precipitated with GST bound to glutathione agarose (FIG. 3). In contrast, GST-p60CDΔ1 was highly phosphorylated, but only in the presence of a divalent cation and ATP (FIG. 3). Control studies revealed that the kinase activity bound to p60CDΔ1 and originated from U-937 cell lysate. No phosphorylation of the fusion protein was seen in the absence of U-937 cell lysate, which indicates that the cytoplasmic domain itself had no kinase activity (FIG. 3, mock). Whatever kinase activity associated with GST was insufficient to phosphorylate GST-p60CDΔ1. Phosphorylated GST-p60CDΔ1 could be cleaved with thrombin (at a cleavage site between GST and p60CDΔ1) to show that only p60CDΔ1 was phosphorylated and not GST.

EXAMPLE 11

Characterization of p60CDΔ1-Associated Kinase Activity

Figure 4:
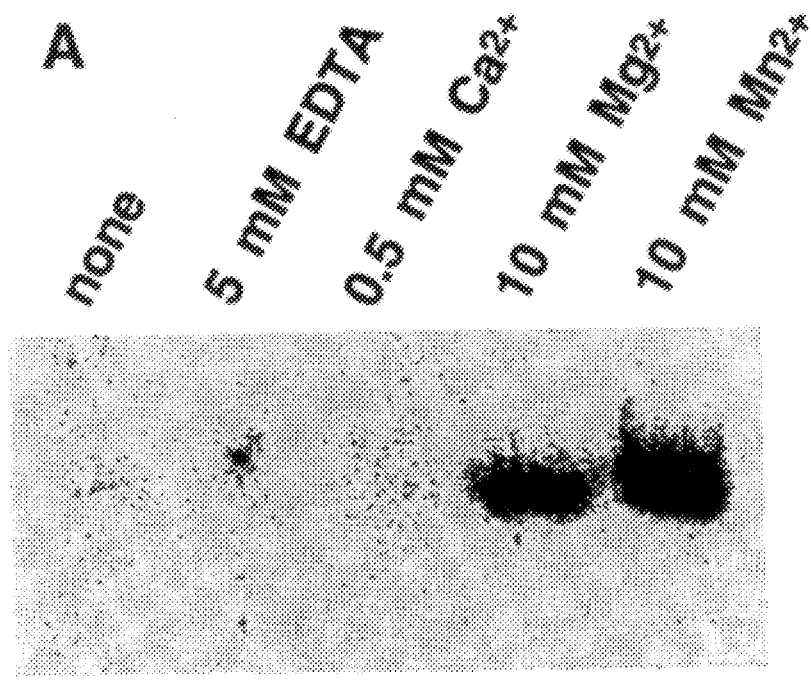
FIG. 4 shows the characterization of GST-p60CDΔ1 associated kinase activity by divalent cation requirement and substrate specificity. U-937 cell extracts ($0.5 \times 10^6$) were used in each assay, and in vitro binding to GST-p60CDΔ1 was performed as described below.
Figure 4:
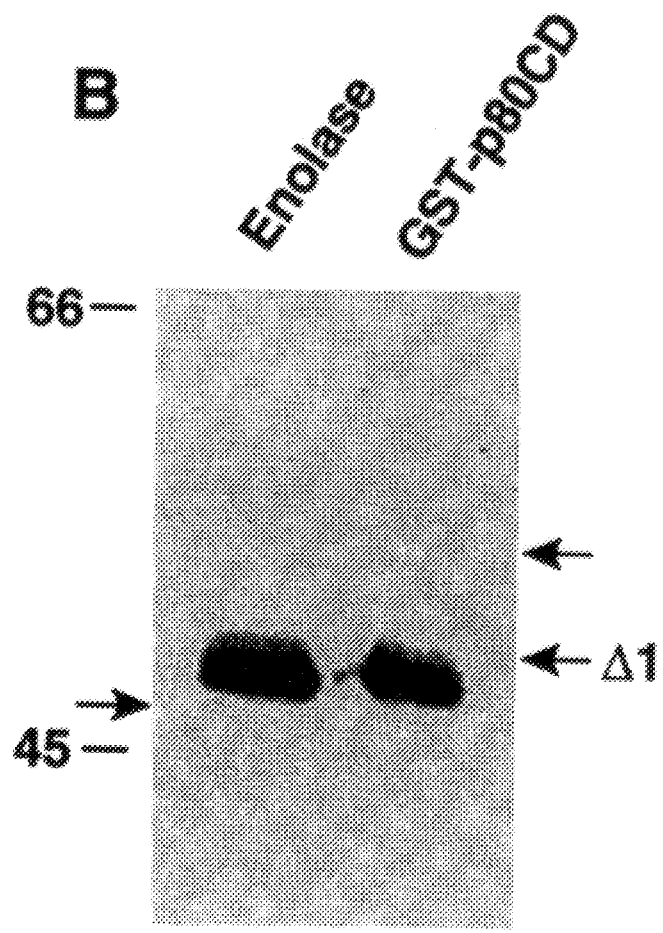
Figure 4:
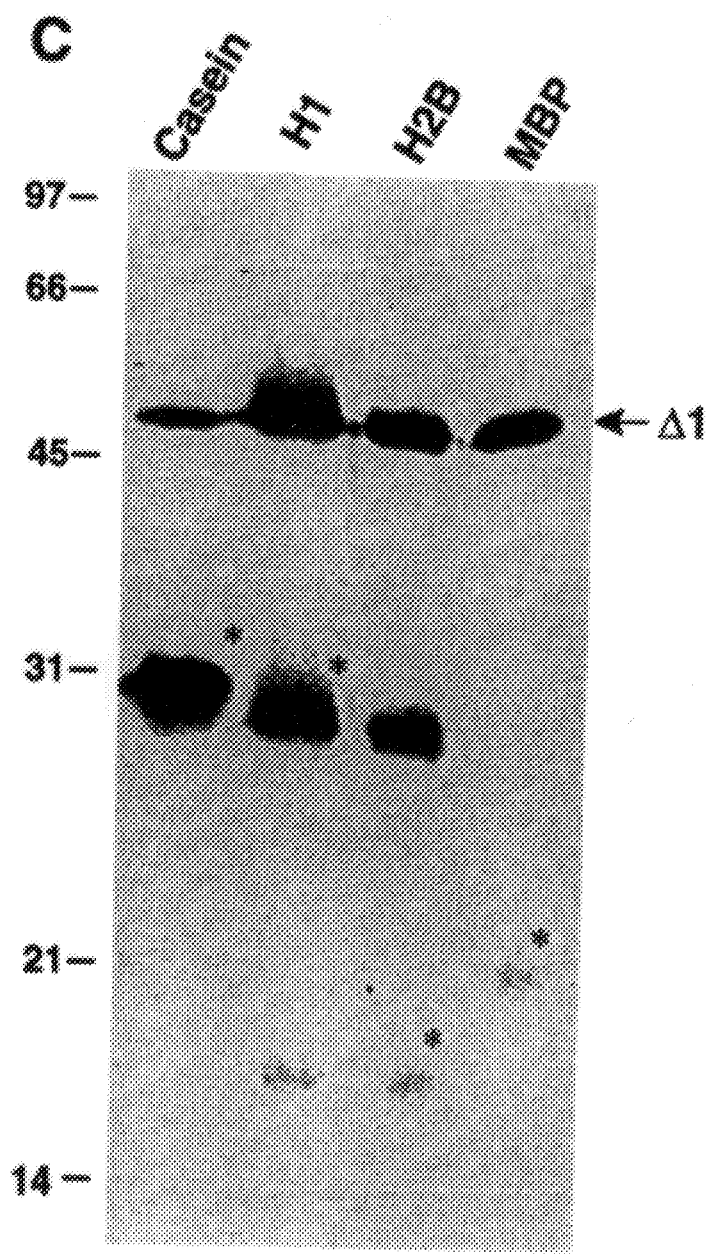
Figure 8:
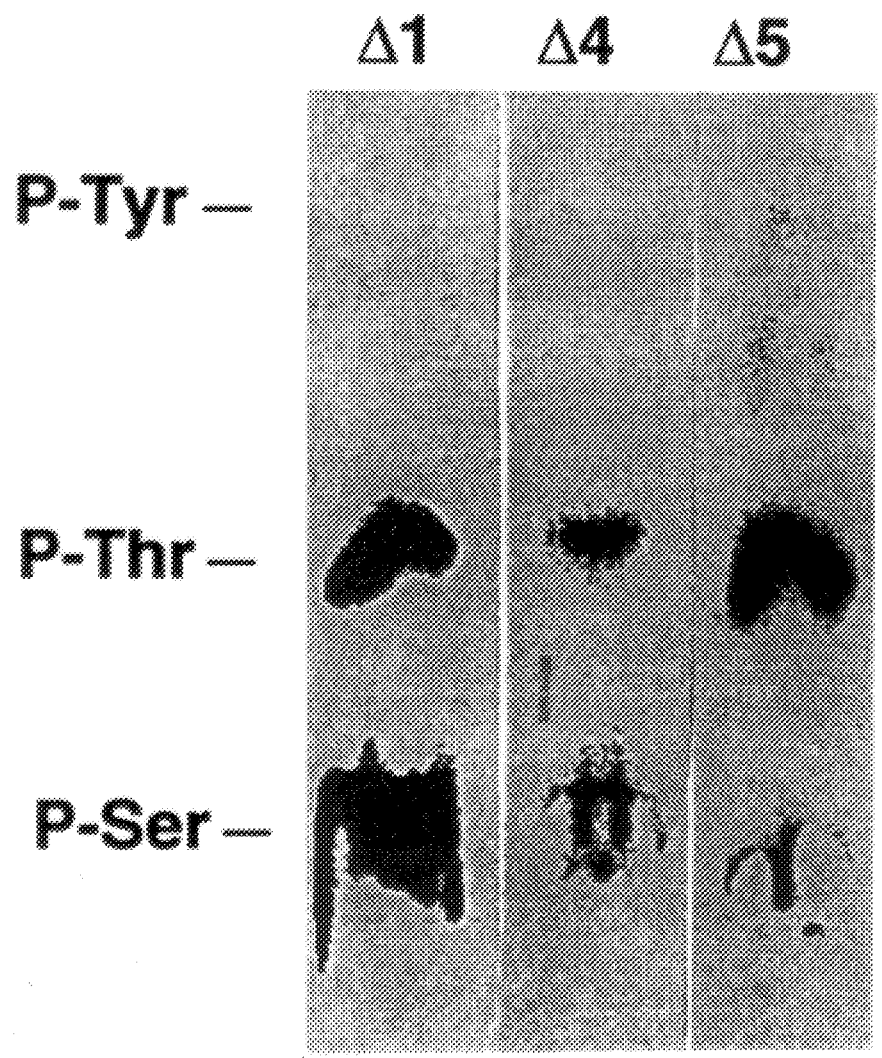
FIG. 8 shows the phosphoamino acid analysis of Δ1, Δ4, and Δ5. Samples subjected to in vitro kinase assays were separated by SDS-PAGE and transferred to PVDF membranes by electrophoresis. Protein bands were excised, boiled with 6N HCl for 1 hour, dried by speed vacuum, and analyzed by TLC in buffer containing 80% methanol, 1.5% acetic acid, and 0.5% formic acid. Subsequently, the dried TLC plate was analyzed by a Phosphorimager. Migration of standards was visualized by spraying the dried TLC plate with ninhydrin.
Figure 9:
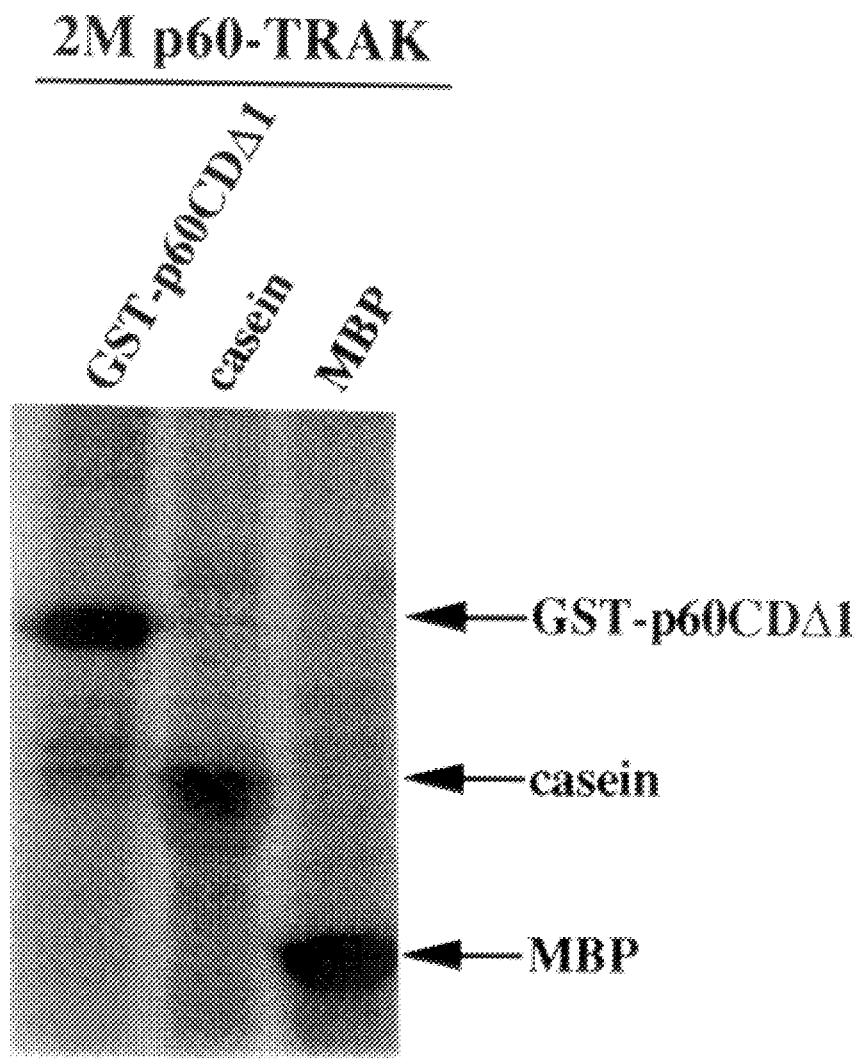
FIG. 9 shows the in vitro kinase assays of 2M NaCl elution of p60-TRAK with GST-p60CDΔ1, casein, and MBP as substrates. Standard kinase assays were performed with a 5 μl portion of the 2M elution with the indicated substrate. Proteins were subjected to 12% SDS-PAGE, the protein bands visualized by staining with Coomassie Blue, and the dried gel was analyzed by a PhosphorImager.

To characterize the receptor-associated kinase activity, its divalent cation requirement and its amino acid and substrate specificity was examined. p60CDΔ1 was phosphorylated in a concentration- and time-dependent manner (FIG. 10) and was about 2-fold higher with $Mn^{2+}$ than with $Mg^{2+}$ (FIG. 4A). The associated kinase activity was inactive when either of these cations was replaced with $Ca^{2+}$ (FIG. 4A). The receptor was phosphorylated primarily on threonine and serine residues in a ratio of 2:1 (FIG. 8), a result also observed with thrombin-cleaved GST-p60CDα1. When examined for substrate specificity, the p60CDΔ1 associated kinase phosphorylated casein, MBP and histone H1, but not histone H2B, enolase, or GST-p80CD (FIG. 4B, FIG. 4C and FIG. 9). Enolase and polyglutamate-tyrosine were not phosphorylated, implying that the associated kinase activity was not tyrosine directed. The phosphoprotein migrating at approximately 29 kDa in the H2B lane is most likely a contaminant from histone H1.

EXAMPLE 12

TNF Stimulates the p60 Cytoplasmic Domain Associated Kinase

Figure 5:
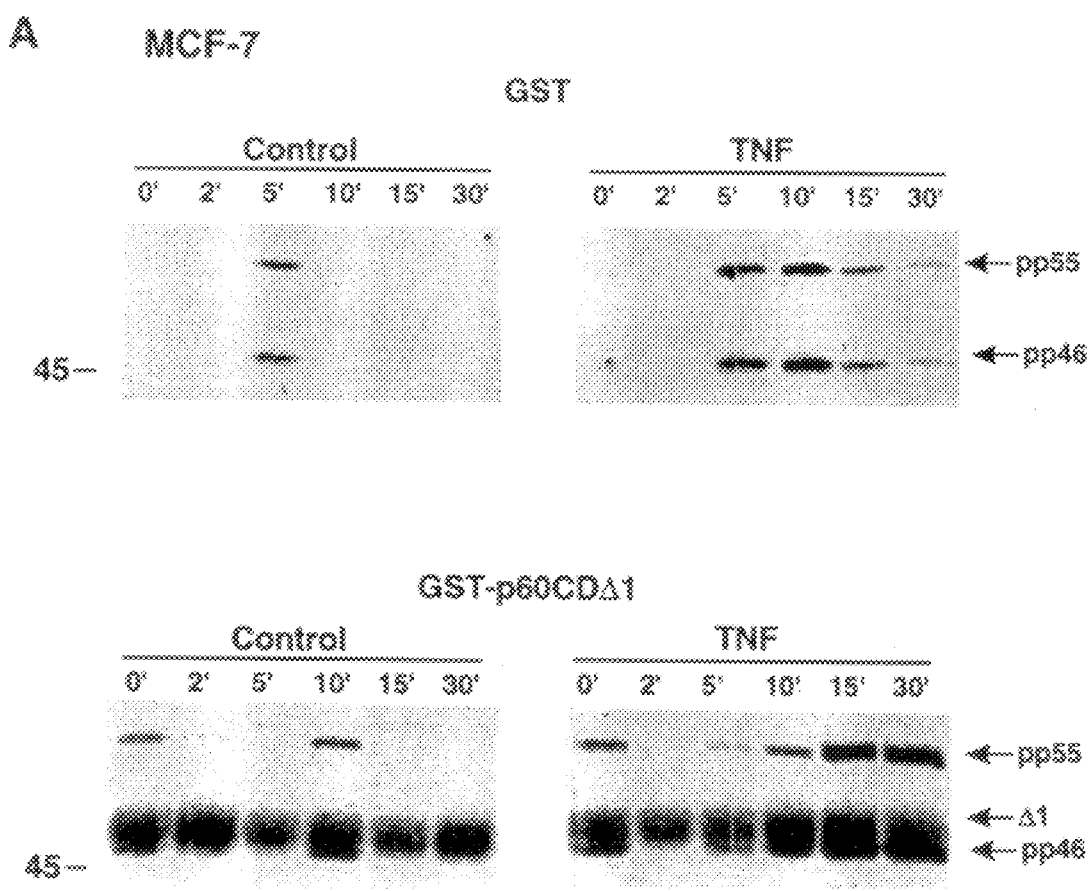
FIG. 5 shows that GST-p60CΔ1 associated kinase activity from MCF-7 (FIG. 5A), foreskin fibroblasts (FIG. 5B), and U-937 (FIG. 5C) increases in response to TNF by measuring GST-p60CDΔ1 phosphorylation.
Figure 5:
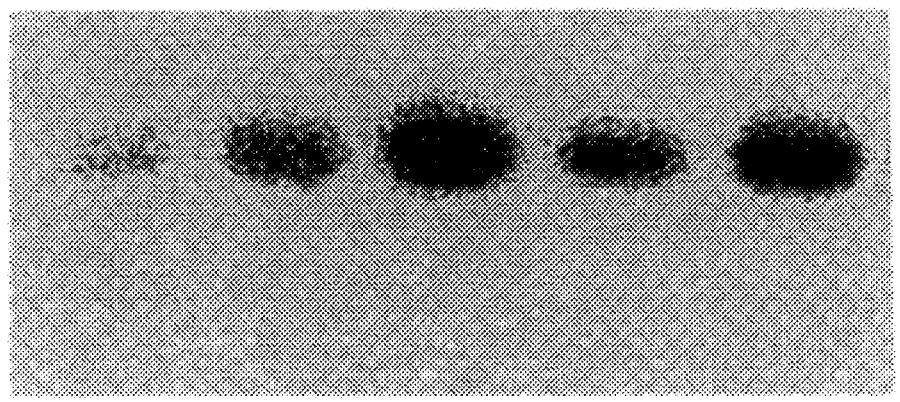
Figure 5:
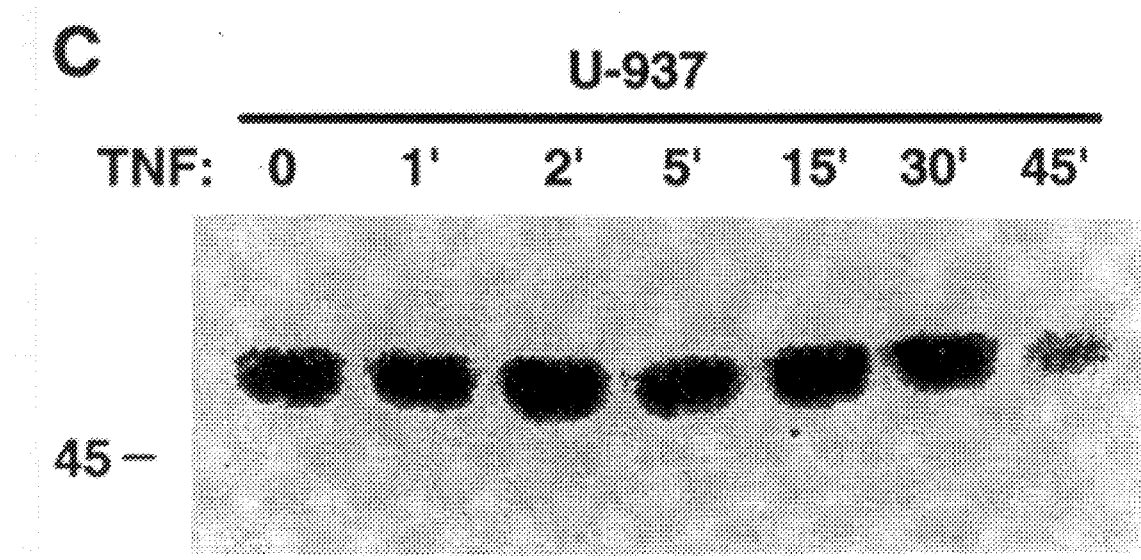

TNF induced the activity of the receptor-associated kinase (p60TRAK). U-937 and MCF-7 cells which undergo antiproliferation and human foreskin fibroblasts which proliferate in response to TNF were used. FIG. 5A shows that TNF treatment for 5–15 minutes of serum-starved MCF-7 cells increased receptor-associated kinase (p60TRAK) activity by 50%; the level declined to normal thereafter. Interestingly, phosphorylation of two other proteins of 46 and 55 kDa (pp46 and pp55, respectively) was increased by 250% in MCF-7 cells within the same time period. The phosphorylation of pp46 and pp55 was $Mg^{2+}$- rather that $Mn^{2+}$-dependent. These similar two bands were also observed when GST was used. However, the phosphorylation of these proteins decreased when the period of TNF treatment was increased.

FIG. 5B shows that treatment of serum-starved human foreskin fibroblasts with TNF for 5 minutes increased phosphorylation of p60CDΔ1 240%. This TNF-dependent phosphorylation of p60CDΔ1 was $Mg^{2+}$-dependent rather than $Mn^{2+}$-dependent. By contrast, under conditions of serum starvation for 18–24 hours, treatment of U-937 cells for various time points with TNF had no effect on receptor-associated kinase activity (FIG. 5C) and longer time periods (more than 30 minutes) showed a decline in the constitutive phosphorylation of the receptor.

EXAMPLE 13

Deletion Mutants of the Cytoplasmic Domain of the p60 Receptor

The present invention shows that a serine/threonine protein kinase associates with the cytoplasmic domain of the p60 form of the TNF receptor. In order to determine the region necessary for binding the kinase and the potential sites within the cytoplasmic domain that undergo phosphorylation, several deletion mutants of the cytoplasmic domain (FIG. 6) were constructed. The intracellular region of p60 form of the TNF receptor contains 222 aminoacyl residues with a large proportion of serine, threonine, proline, and acidic residues. Essentially, the cytoplasmic domain can be divided into two parts: 1) an N-terminal half that is rich in serine, threonine, and proline, and 2) a C-terminal half that contains a cluster of acidic residues. Therefore, GST fusion proteins containing deletions of the cytoplasmic region were generated to illustrate the functional role of these unique regions.

The examples above show that Δ1 (243–426) is sufficient for binding kinase activity from U-937 cell lysate and also serves as a substrate for the associated kinase. Deletion mutant Δ2 (243–274) contains the serine-, threonine- and proline-rich region, whereas Δ4 (276–426) lacks it. Deletion mutants Δ3 (243–323) and Δ5 (324–426) are the N-terminal and C-terminal halves of the cytoplasmic domain, respectively. The C-terminal acidic rich region is common to deletion proteins Δ1, Δ4, and Δ5. In addition, the deletion protein Δ5 is essentially the death domain as previously described. The GST fusion constructs were used to express the fusion proteins in E. coli; they were purified by affinity chromatography to glutathione-agarose (FIG. 6B). In order to minimize degradation of the fusion proteins in vivo, both Δ1 and Δ4 were expressed at 15° C. while all others were expressed at 37° C.

EXAMPLE 14
Binding and Phosphorylation by the Receptor-Associated Kinase Occurs Only with Δ1, Δ4, and Δ5

Figure 7:
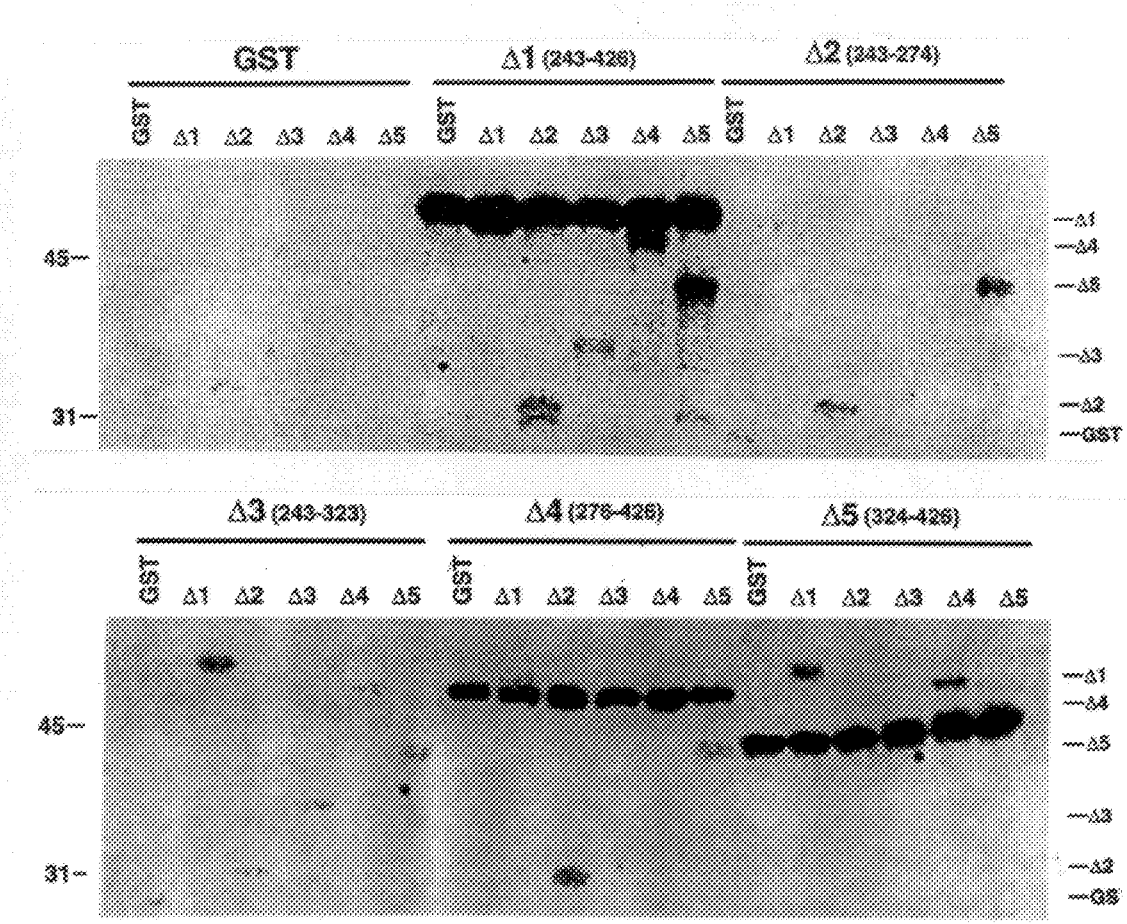
FIG. 7 shows the kinase activity from U-937 cells binds to and phosphorylates Δ1, Δ4, and Δ5. Lysate from 6×10⁶ cells were used for each binding reaction, after which samples were split into six tubes containing each of the indicated substrates for kinase assays as described below. The samples were subjected to 9% SDS-PAGE and a phosphorimage of the dried gel is shown. The positions of the deletion proteins were visualized by Coomassie Blue staining and their migration is shown on the right.

To illustrate the region necessary for binding and also for phosphorylation by the associated kinase, GST and the deletion mutants were used as both binding proteins and substrates for kinase reactions. Essentially, precleared cell lysates were bound to the desired fusion protein, washed extensively, and separated into tubes that contained substrates (GST or one of the deletion proteins) for i n vitro kinase reactions. The deletion proteins Δ1, Δ4, and Δ5 were the only proteins capable of binding kinase activity and serving as substrates for the associated kinase (FIG. 7). GST neither bound any kinase activity nor served as a substrate in kinase reactions (FIG. 7). The amount of associated-kinase activity appeared to be highest with Δ1 followed by Δ5 and Δ4, in order.

EXAMPLE 15
Serine and Threonine Phosphorylation Observed with Δ1, Δ4, and Δ5

In order to determine the type of phosphorylation, the deletion proteins were subjected to phosphoamino acid analysis. All three deletion proteins incorporated phosphate on serine and threonine residues (FIG. 8). The ratio of threonine to serine phosphorylation agreed with the threonine to serine content in each deletion protein. Since Δ2 and Δ3 were not phosphorylated, it is likely that phosphorylation occurs in the C-terminal half of the cytoplasmic domain. However, proper folding in these mutants may be disrupted or may require residues within the C-terminal region for kinase recognition in order to be phosphorylated. Although deletion mutant Δ5 contains a smaller proportion of serine and threonine than Δ2 and Δ3, most of the phosphorylation appeared to occur in deletion mutant Δ5.

EXAMPLE 16
The C-terminal Acidic Region is Sufficient for Physical Interaction with the Protein Kinase Serine and/or acidic rich regions have been identified in other cytokine receptors such as mouse erythropoietin receptor, mouse and human granulocyte colony-stimulating factor receptors, human IL-2 receptor β chain, human IL-4 receptor, human IL-7 receptor, gp130, and the common human accessory chain $β_c$. These types of motifs appear to be necessary for these receptors to recognize intracellular components of their signaling pathways. The C-terminal half of the cytoplasmic domain of p60 is a common element found in deletion mutants Δ1, Δ4, and Δ5. Interestingly, deletion mutant Δ5 contains all the necessary structural elements required for interaction with the receptor-associated kinase. Within this domain, there resides a cluster of acidic residues, perhaps necessary for protein-protein interactions. In contrast, the serine-, threonine- and proline-rich domain of both the Δ2 and Δ3 mutants did not bind kinase activity. Thus, it seems likely that the cluster of acidic residues in the death domain and not the serine-rich region is necessary for interaction with the protein kinase.

Interestingly, deletion mutant Δ5 is essentially the death domain known to be necessary and sufficient for signaling cell death. The mutational analysis of the cytoplasmic domain of the p60 form of the tumor necrosis factor receptor suggests that the N-terminal half of the cytoplasmic domain is necessary for ligand-dependent clustering of the receptor, whereas the C-terminal half may associate with intracellular signaling molecules. Thus, the present invention supports the premise that the death domain of the intracellular region is necessary for interaction with intracellular molecules, specifically a serine/threonine protein kinase.

EXAMPLE 17
Purification of p60-TRAK

Approximately $14.5 \times 10^9$ U937 cells were grown to a density of $1.4 \times 10^6$/ml in 10.5 L of RPMI-1640 medium in the presence of 10% FBS. Cells were collected by centrifugation, washed three times with 50 ml cold PBS, and lysed in approximately 120 ml lysis buffer for 30 minutes on ice. The lysate was cleared by centrifugation at 8000 rpm for 10 minutes at 4° C. in an SS34 rotor. The supernatant was mixed with 1 mg of GST attached to glutathione-agarose beads overnight at 4° C. with rocking. Next, the mixture was centrifuged at 3000 rpm for 10 minutes and the supernatant was mixed with 500 $\mu$l of a 50% slurry of GST-p80CD attached to glutathione-agarose beads for 4 hours at 4° C. The mixture was centrifuged and the supernatant was mixed with a 50% slurry of GST-p60CDΔ1 attached to glutathione-agarose beads for 4 hours at 4° C. The beads were centrifuged and the supernatant was discarded. Equal volumes of the beads were transferred to 10 eppendorf tubes. The beads were washed by the following method and each wash was saved: six washes (600 $\mu$l each) of lysis buffer, five washes (600 $\mu$l each, 5 minutes rocking in between each wash) of 1M NaCl in lysis buffer, and five washes (600 $\mu$l each, 10 minutes rocking in between each wash) of 2M NaCl, 10 mM EDTA in lysis buffer. Subsequently, each of five tubes were washed onto a column with two washes (500 $\mu$l each) and washed on the column with 1 ml of 2M NaCl, 10 mM EDTA in lysis buffer followed by 1.5 ml lysis buffer. The 1M and 2M salt washes were concentrated and the buffer exchanged to a buffer consisting of 20 mM HEPES, 50 mM NaCl, 10% glycerol, 0.1% 2-mercaptoethanol, 10 mM NaF, and 0.2 mM sodium orthovanadate. Kinase assays were performed with casein, MBP, and GST-p60CDΔ1 as substrates (FIG. 9).

The present invention identifies a specific serine/threonine protein kinase that binds to the cytoplasmic domain of the p60 form of the tumor necrosis factor receptor and causes its phosphorylation. Although there are several reports of TNF-dependent activation of protein kinases, the signaling events at the receptor level are not known. Neither the p60 nor the p80 form of the TNF receptor has any significant homology to known protein kinases, and they do not possess any intrinsic protein kinase activity. Thus, the p60 receptor-associated molecules with protein kinase activity were identified by utilizing a GST fusion protein containing the cytoplasmic domain of p60 linked to glutathione-agarose as an affinity matrix.

The p80 form of the TNF receptor has been demonstrated to be constitutively phosphorylated on serine residues (97%) with minimal incorporation of phosphate into threonine residues (3%). There have been no report on the phosphorylation of the p60 form of the TNF receptor. The present invention shows that p60CDΔ1 serves as a substrate in in vitro kinase assays and that phosphorylation sites exist within the cytoplasmic domain. Proteins from U-937 cells adsorbed to GST-p60CDΔ1 exhibited serine/threonine kinase activity that also phosphorylated GST-p60CDΔ1. The associated kinase activity was selective in phosphorylating exogenous substrates, of which casein, myelin basic protein and histone H1 were the most highly phosphorylated. The receptor-associated kinase activity was specific for the cytoplasmic domain of the p60 receptor since it showed little or no activity towards the cytoplasmic domain of the p80 receptor. Furthermore, a kinase activity associated with the p80 cytoplasmic domain did phosphorylate the p60 cytoplasmic domain, revealing that the two receptors have distinct structural as well as functional characteristics. A similar kinase activity associated was also demonstrated with p60CDΔ1 in TNF-treated MCF-7 and foreskin fibroblasts.

The identification of a 52-kDa phosphoprotein from U-937 cells that binds to the p60 cytoplasmic domain suggests that structural information for protein interactions is located within this region. The cytoplasmic domain undergoes phosphorylation and also recruits a protein kinase, and therefore, signaling events by the p60 form of the tumor necrosis factor receptor are initiated through the cytoplasmic domain.

Cytokine receptors that lack intrinsic kinase activity transmit their signals by recruiting intracellular protein kinases through interactions with their cytoplasmic domains. Cytoplasmic deletions of the p60 receptor have demonstrated that specific regions are necessary for generating the TNF-induced cytotoxic signal. The cytoplasmic domain of the p60 form of the TNF receptor consists of 221 amino acids having no significant homology to any other receptor.

Approximately 96 amino acids of p60CD (residues 330–426) share 24% identity with 68 amino acids of the Fas antigen (residues 231–298). Although the homology is weak, the cytotoxic signal generated by both p60 and Fas antigen are quite similar. Tartaglia et al. demonstrated that a p60/Fas chimeric receptor was able to transduce a somewhat modest cytotoxic signal in response to agonistic p60 receptor antibodies, suggesting the signals emanating from these homologous domains are similar. The homologous region shared by p60 and Fas antigen resides within the death domain of p60 (residues 324–426) and is sufficient to transduce the cytotoxic signal. The cytoplasmic domain of p60 is rich in amino acid residues (17 serine, 17 threonine, 7 tyrosine) that can potentially undergo phosphorylation. An abundance of proline residues are found predominantly in the N-terminal half of the cytoplasmic domain located within a serine/threonine-rich region. An emerging family of serine/threonine kinases that recognizes substrates containing the motif X-Ser/Thr-Pro-X, termed proline-directed protein kinases, has been described. The p60 cytoplasmic domain contains nine such motifs, of which two are found within the death domain. In light of the finding that the death domain is sufficient for TNF signaling, a potential site of phosphorylation by a proline-directed proten kinase is found within this domain.

TNF signals for both growth inhibitory and stimulatory activities depending on the cell type. It is unknown if the molecules recruited by the receptor for these two types of responses are identical. The present invention demonstrates that the p60 form of the TNF receptor binds a serine/threonine kinase that is activated by TNF. The demonstration that the death domain is necessary and sufficient for transmitting the growth inhibitory signals by TNF suggests that this is the region responsible for binding intracellular protein kinases. Further, given the teachings of the present invention, one with ordinary skill in this art will readily be able to determine the sites of phosphorylation and the residues necessary for protein interactions with regard to signal transduction by the TNF receptor.

EXAMPLE 18

The p60 TNF Receptor-Associated Kinase (TRAK) Binds Residues 344–397 of the Cytoplasmic Domain Involved in TNF Signaling The p60 form of the tumor necrosis factor receptor lacks motifs characteristic of tyrosine or serine/threonine protein kinases. A p60 TNF receptor-associated kinase (p60-TRAK) from U-937 cells physically interacts with and causes the phosphorylation of the cytoplasmic domain of the TNF receptor. To define the region of the cytoplasmic domain necessary for physical interaction with p60TRAK, a series of deletions were constructed (grouped into three sets D1–D5, D6–D12, and D13–D16) of the p60 cytoplasmic domain, expressed them as glutathione-S-transferase (GST) fusion proteins, and used them in affinity precipitations, followed by in vitro kinase assays. A detailed analysis indicated that a serine-, threonine- and proline-rich region (residues 243–274, D2) and the N-terminal half of the cytoplasmic domain (residues 243–323, D3) neither associated with p60-TRAK nor underwent phosphorylation. Out of 222 residues (205–426) in the cytoplasmic domain, only 54 (344–397, D12) were sufficient for binding p60-TRAK and for phosphorylation of the cytoplasmic domain. A region of approximately 30 residues (397426) at the C-terminal end was found to interfere with optimal binding of the p60-TRAK activity. Thus, the minimal region of the cytoplasmic domain necessary for interacting with p60-TRAK and for phosphorylation resides within the domain previously reported to be needed for signaling the cytotoxic effect of TNF.

EXAMPLE 19

Materials

The histiocytic lymphoma cell line U-937 (CRL 1593) was obtained from the American Type Culture Collection (ATCC). Cells were grown in RPMI-1640 medium supplemented with 10% FBS and 100 $\mu$g/ml streptomycin at 37° C. in a 5% $CO_2$ incubator. *Escherichia coli* strain BL21 and plasmids pGEX-2TH and pCMVXVBpL4-p60 have been described above.

EXAMPLE 20

Construction, Expression, and Purification of GST Fusion Protein

Figure 10:
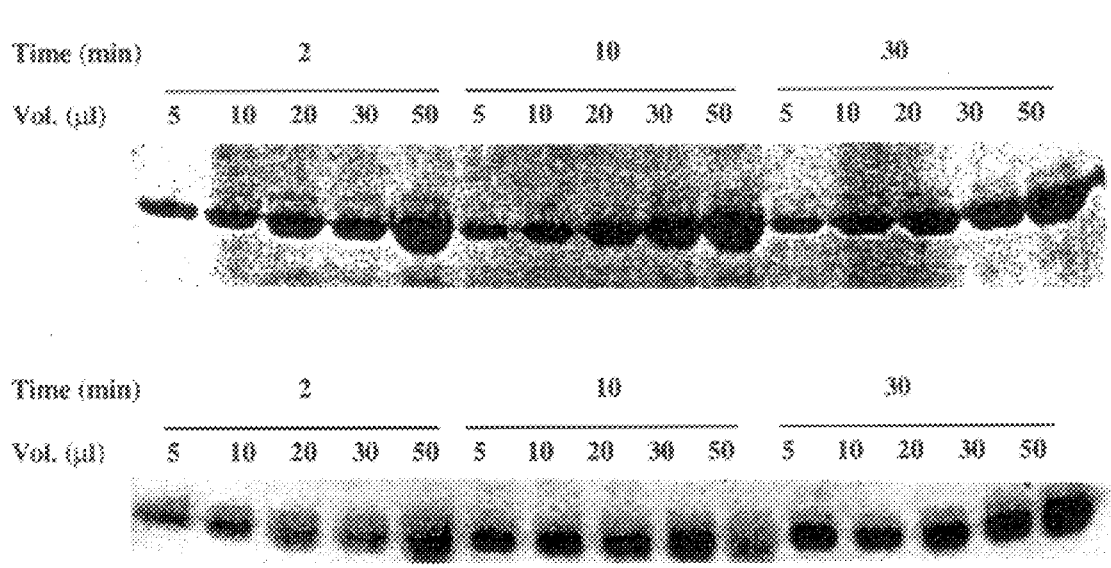
FIG. 10 shows the concentration- and time-dependent phosphorylation of GST-p60CDΔ1 with the receptor associated kinase. Cells (1.0×10⁶) were used for in vitro binding and kinase reactions with increasing amounts of the substrate for the indicated times in the kinase reaction. Proteins were subjected to 7.5% SDS-PAGE, the protein bands visualized by staining with Coomassie Blue (upper panel) and the dried gel was analyzed by a PhosphorImager (lower panel).

The construction of the plasmid encoding GST-p60CDD1 is described above. FIG. 10 illustrates the fusion proteins that were made herein. Specific primers for each deletion construct were used to amplify fragments with unique restriction sites by PCR using pCMVXVBpL4-p60 as the template. The PCR products were digested with either EcoRI/HindIII or BamHI/HindIII and inserted into digested pGEX-2TH to yield the appropriate expression vectors. All expression vectors were sequenced to ensure that amplification was correct. Expression and purification of the GST fusion proteins from BL21 cells harboring the appropriate expression vector were carried out as described above. The fusion proteins were stored at 4° C. on glutathione-agarose beads as a 50% slurry in Buffer A (20 mM Tris, pH 8.0, 200 mM NaCl, 10% glycerol, 0.5% NP-40, 1 mM PMSF, 2 $\mu$g/ml aprotinin, 2 $\mu$g/ml leupeptin, and 0.1% 2-mercaptoethanol). The amount of fusion protein was estimated by Coomassie Blue staining of SDS-PAGE gels.

EXAMPLE 21

In Vitro Binding of GST Fusion Protein to Cell Extracts

U-937 cells were lysed in 600 $\mu$l of lysis buffer (20 mM HEPES, pH 7.4, 0.1% NP-40, 250 mM NaCl, 10 mM NaF, 0.2 mM sodium orthovanadate, 1 mM PMSF, 2 $\mu$g/ml aprotinin, and 2 $\mu$g/ml leupeptin) on ice for 30 minutes followed by 10 minutes of centrifugation in a microfuge. The supernatant was adjusted to 125 mM NaCl by addition of lysis buffer without NaCl, and precleared with 25 $\mu$g of GST in 50 $\mu$l of 50% (v/v) glutathione agarose for 1 hour at 4° C. The precleared supernatant was mixed with approximately 5–10 $\mu$g GST or the appropriate fusion protein attached to glutathione-agarose beads for 1 hour at 40 C. The beads were collected by centrifugation and washed extensively with lysis buffer (4×500 $\mu$l) and with kinase buffer (3×500 $\mu$l: 20 mM HEPES, pH 7.4, 10 mM NaF, 0.2 mM sodium orthovanadate, and 0.1% 2-mercaptoethanol). The pellets were then used for in vitro kinase assays.

EXAMPLE 22

In Vitro Kinase Assays

Standard kinase assays were carried out for 20 minutes at 37° C. in 30 μl containing 20 mM HEPES, pH 7.4, 10 mM MgCl$_2$, 0.2 mM ATP, 0.2 mM NaF, 0.1 mM sodium orthovanadate, and 10 μCi [g-$^{32}$P]ATP. Reactions were stopped with 15 μl SDS-sample buffer, boiled for 5 minutes, and subjected to SDS-PAGE. Protein bands were visualized by staining with Coomassie Blue, and the dried gels were analyzed by a Phosphorimager (Molecular Dynamics, Sunnyvale, Calif.) and quantitated by ImageQuant Software (Molecular Dynamics, Sunnyvale, Calif.). In vitro kinase assays with 5 μg histone (Type VIs, Sigma Chemical Company, St. Louis, Mo.) followed the standard kinase assay.

EXAMPLE 23

Design of Deletion Mutants of the Cytoplasmic Domain of the p60 Receptor

Figure 11:
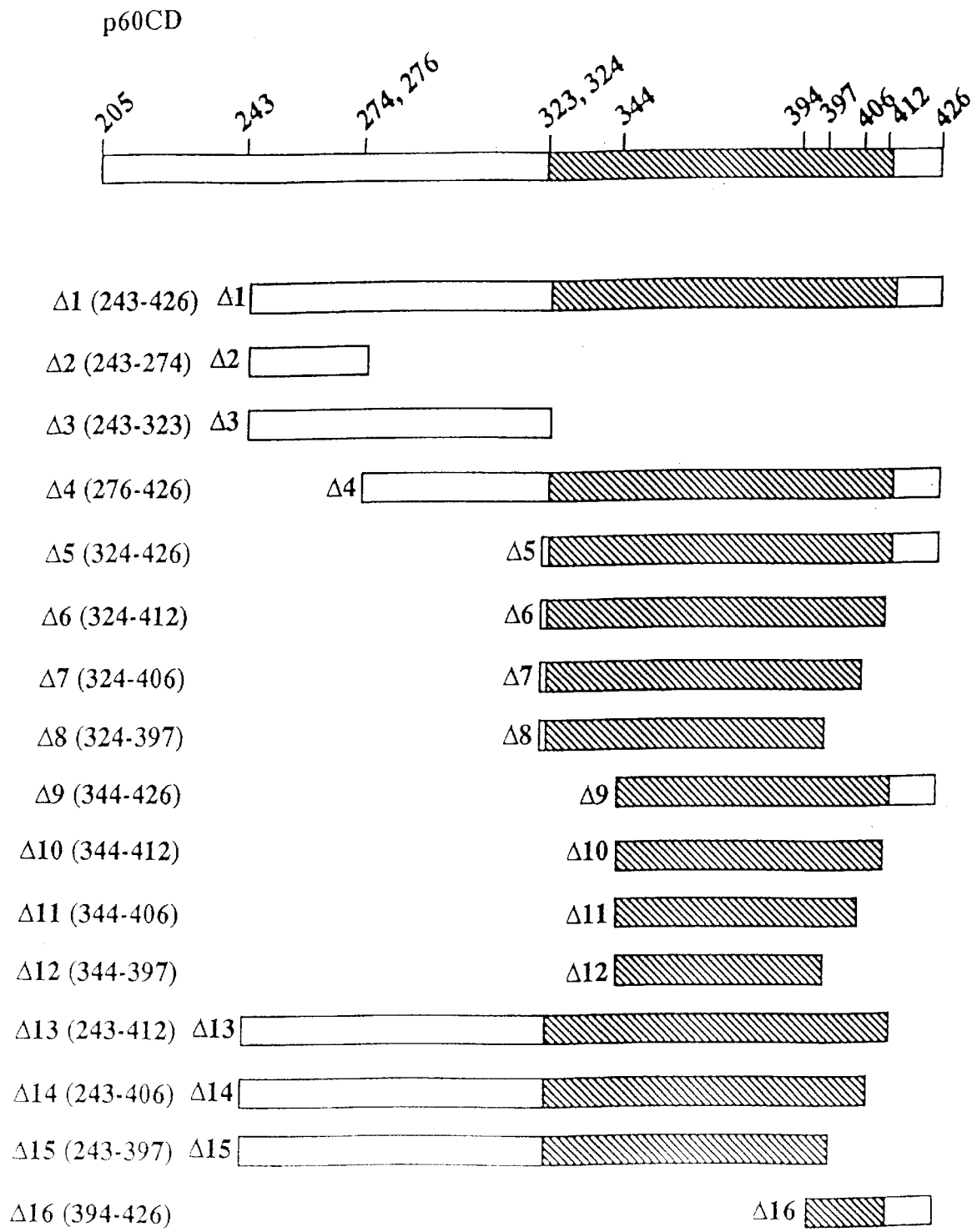
FIG. 11 shows a schematic diagram of the deletion mutants of the cytoplasmic domain of the p60 TNF receptor. The entire cytoplasmic domain (residues 205 to 426) of the p60 TNF receptor is shown as p60CD. Each deletion mutant was expressed as a fusion protein linked to GST as described below. The shaded region indicates the death domain.

As shown above, residues 243–426 bind p60-TRAK activity from U937 cell lysate and also serve as a substrate for the associated kinase activity. The intracellular region of p60 contains 222 aminoacyl residues (205–426) with a large proportion of serine, threonine, proline, and acidic residues. Essentially, the cytoplasmic domain can be divided into two parts: an N-terminal half (residues 205–323), which is rich in serine, threonine, and proline, and a C-terminal half, which contains a region necessary for signaling the cytotoxic response of TNF. To determine the minimal region of the cytoplasmic domain necessary for interacting with p60-TRAK activity and the potential sites of phosphorylation, a series of deletion mutants of the cytoplasmic domain of the p60 TNF receptor were designed (FIG. 11). For analysis, the deletions were grouped into three sets: set 1 (D1–D5), set 2 (D6–D12), and set 3 (D13–D16).

EXAMPLE 24

Figure 12:
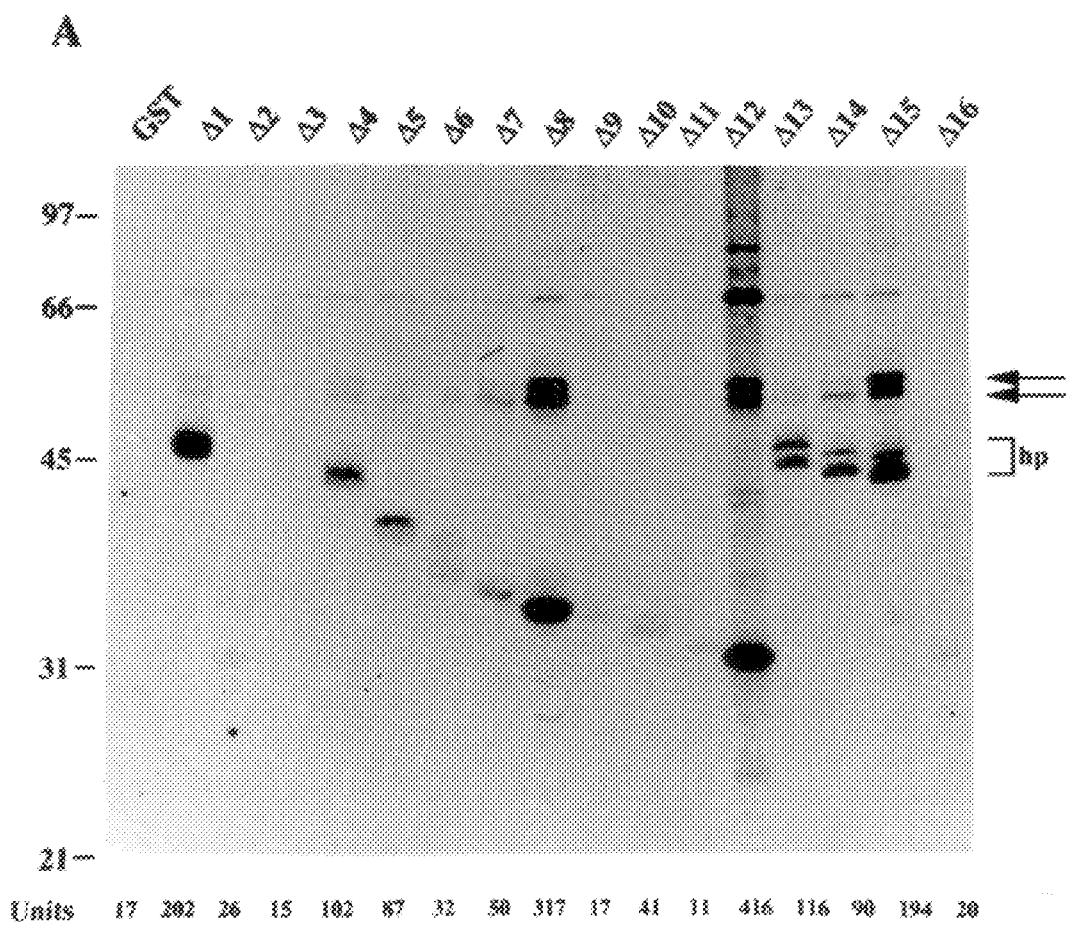
FIG. 12 shows the in vitro kinase assays of U-937 cell lysates bound to each of the GST-fusion proteins. Cell lysates from 2×10⁶ cells were used for each binding reaction, after which kinase assays were performed as described below. The samples were subjected to 9% SDS-PAGE and the Coomassie Blue stained gel was dried (2B) and then subjected to autoradiography (2A). Molecular mass standards are expressed in kDa. The arrows indicate the position of pp55 and pp58, and hp in the lanes of Δ13–Δ15 represents hyperphosphorylated forms. The arbitrary units represent the relative amount of phosphorylation of each GST fusion protein when quantitated by a Phosphorimager and ImageQuant Software. Images were essentially identical in at least 5 other identical experiments.
Figure 12:
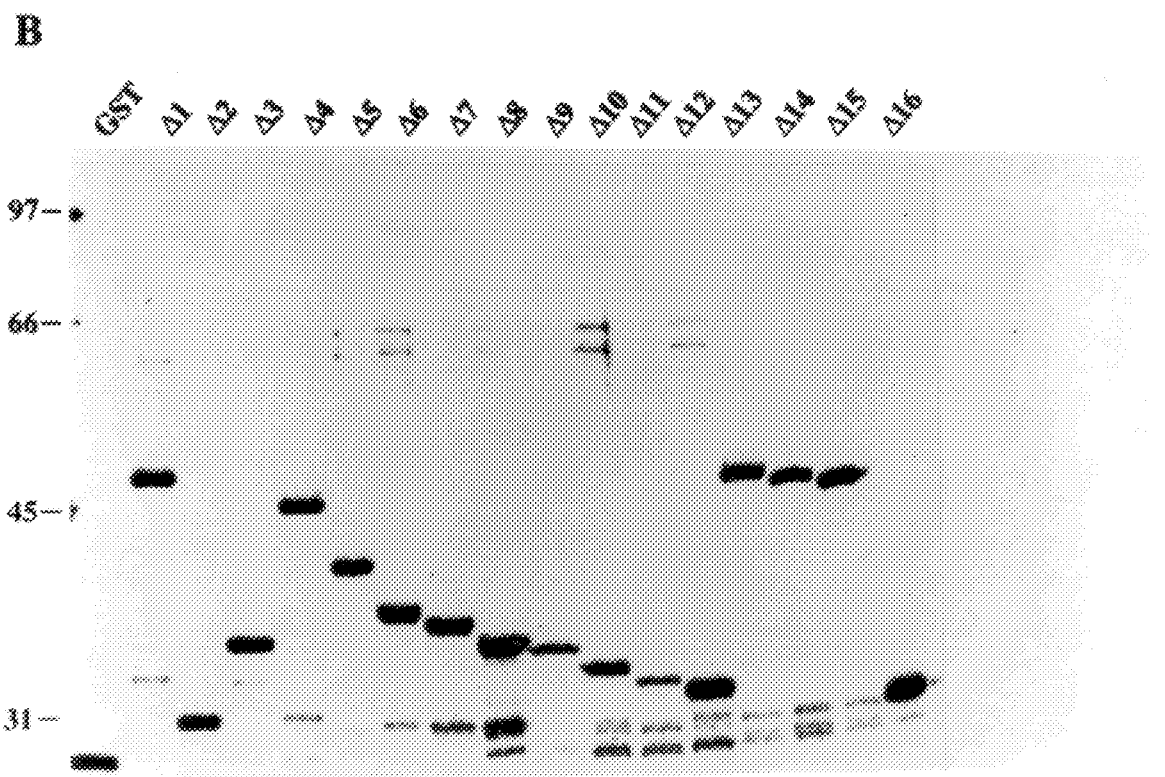
Figure 13:
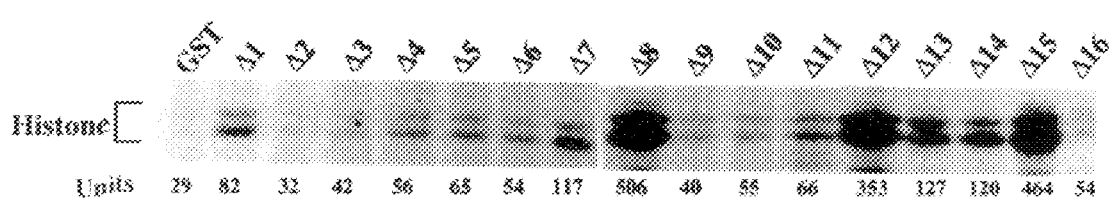
FIG. 13 shows that histone kinase activity associated with the deletion mutants of the p60 TNF receptor. The receptor-associated kinase activity was measured using 5 μg histone as an exogenous substrate as described below. Images were essentially identical in at least 3 other identical experiments.

Binding and Phosphorylation by the Receptor-Associated Kinase Occurs Within the C-terminal Half The first set of deletions constructed (FIG. 11, D1–D5) were to ascertain if the kinase activity would bind to and phosphorylate the domain shown to be important for TNF-dependent cytotoxicity. Essentially, precleared cell lysates were bound to the desired fusion protein, washed extensively, used for in vitro kinase reactions, and analyzed by Coomassie Blue staining of SDS-PAGE gels (FIG. 12B) and autoradiographed (FIG. 12A). In the first set of deletions, fusion proteins D1, D4, and D5 were capable of binding kinase activity and serving as substrates for the associated kinase activity (FIG. 12). GST neither bound any kinase activity nor served as a substrate in this or subsequent kinase reactions (FIG. 12). Kinase activity did not associate with the N-terminal half of the cytoplasmic domain (ie, residues 243–323, D3). The phosphorylation of D4 and D5 was approximately 50% of the phosphorylation of D1. In this set of deletions, the smallest region that bound kinase activity was residues 324–426 (D5).

EXAMPLE 25

Residues 344–397 Contain the Minimal Region Necessary for Binding

To further narrow the region necessary for binding the kinase activity, D5 was deleted more extensively (FIG. 11, D6–D12). Kinase activity was associated with deletion mutants D8 and D12 more strongly than D6, D7, and D9–D11 (FIG. 12). Surprisingly, the phosphorylation of deletion mutants D8 and D12 was also greater than with D1 (FIG. 12). The minimal region found to be phosphorylated and to associate with the kinase activity was contained within 54 amino acids that reside within the death domain, namely residues 344–397, corresponding to D12. Phosphoamino acid analysis performed on D12 indicated phosphorylation of both serine and threonine residues (data not shown). There are two serines (S352 and S373) and three threonines (T377, T382, and T388) in this region that could be possible sites of phosphorylation by the associated kinase. The amount of kinase activity associated with D12 was comparable to that of D8 (FIG. 12); however, a few more proteins were found to be phosphorylated and associated with D12, either directly or indirectly.

EXAMPLE 26

A C-Terminal 30 Residue Region Inhibits Binding of Kinase Activity

That deletion mutants D9–D11 did not bind kinase activity even though they had the same N-terminus as D12 suggests that residues 397–426 serve an inhibitory function. This could arise from the binding of a protein to residues 397–426, thus inhibiting the binding of the associated kinase. Another possibility is that residues 397–426 bind a protein that regulates kinase activity. The possibility that deletions D9–D11 were poor substrates for the associated kinase was ruled out since the kinase associated with D8 could phosphorylate D9–D11 (data not shown).

Since residues 397–426 appeared to inhibit binding of the kinase activity, a set of deletions were constructed that had the same N-terminus as D1 and the same C-terminus as deletion mutants D10–D12 (FIG. 11, D13–D15). In addition, a deletion mutant, D16, was constructed which contained residues 394–426. If residues 397–426 affects optimal binding of the kinase activity to D1, then increased kinase activity associated with deletion mutants D13–D15 should observed. In fact, there was increased phosphorylation using these deletions (FIG. 12). Deletions D13–D15 were hyperphosphorylated as indicated by slower migrating bands. As was expected, D16 did not bind any significant kinase activity. When cell lysate was bound to D16 and mixed with the D8-associated kinase prior to an in vitro kinase reaction, kinase activity was not inhibited, thus failing to demonstrate that a protein bound to D16 regulates the kinase activity associated with D8 (data not shown).

EXAMPLE 27

Deletion Mutants With the Highest Histone Kinase Activity

To determine the amount of kinase activity associated with each of the deletions, histone as an exogenous substrate in the kinase reactions was used. The histone kinase activity was highest with deletion D8, D12, and D15 (FIG. 3). This is consistent with the observation that the C-terminal 30 residues confers an inhibitory function upon binding of the kinase to the minimal region, residues 344–397.

EXAMPLE 28

Additional Proteins are Phosphorylated in Precipitates with the Deletion Mutants Interestingly, after in vitro kinase assays two additional proteins, of approximately 58 kDa (pp58) and 55 kDa (pp55), were found to be phosphorylated in reactions containing deletion mutants D1, D4, D5, D7, D8, and D12–D15 (FIG. 12). Both pp58 and pp55 were highly phosphorylated by the kinase activity bound to D8, D12, and D15, all of which end in the same C-terminal residue (FIG. 11). Since residues found within deletion mutants D8, D12, and D15 are known to be necessary for receptor aggregation, it may be that either pp58 or pp55 is the endogenous p60 TNF receptor. Immunoblotting with antibodies directed against the p60 TNF receptor failed, however, to detect proteins of this size after precipitation of cell lysates with D8, D12, and D15. A few additional proteins were phosphorylated in the kinase reaction with deletion mutant D12; however, whether these proteins bound directly or indirectly to D12 could not be determined (FIG. 12).

Figure 14:
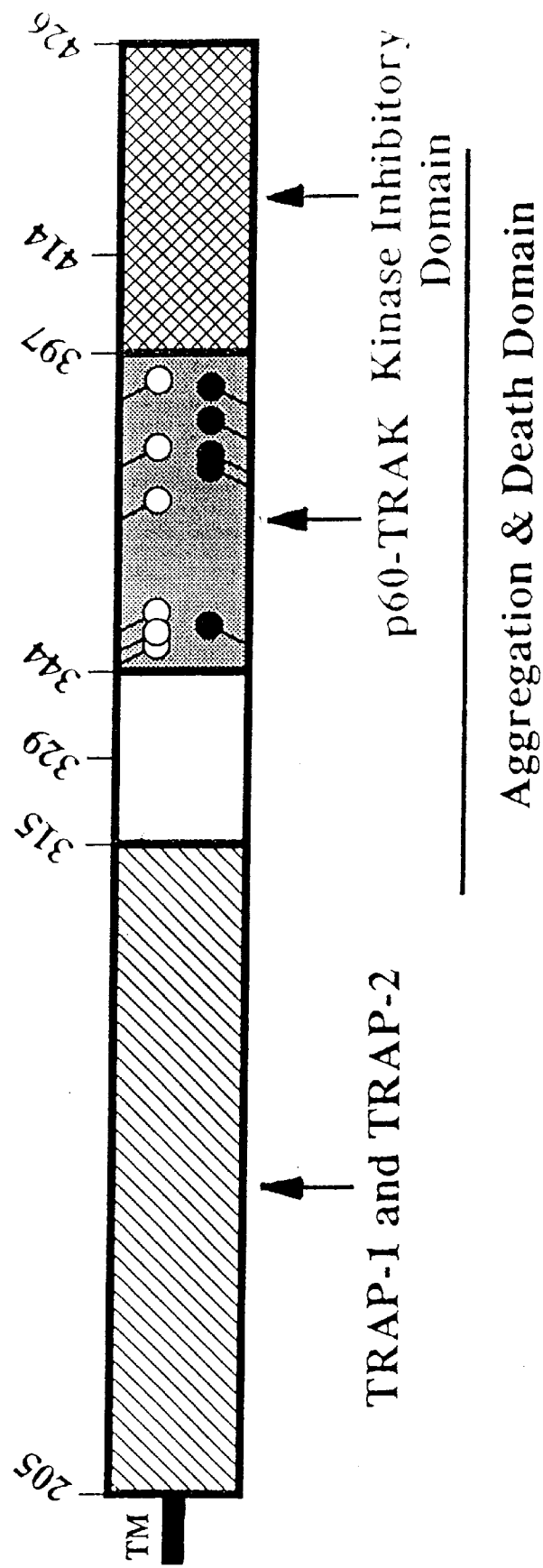
FIG. 14 shows a summary of the p60 TNF-receptor associated molecules. A diagram of the entire cytoplasmic domain is shown with regions mapped for binding TRAP-1 and TRAP-2, p60-TRAK, the kinase inhibitory domain, and the aggregation and death domain. The open circles represent alanine substitutions that render the receptor nonfunctional for cytotoxicity. The closed circles represent potential phosphorylation sites by p60-TRAK.

The present invention demonstrates that residues 344–397 of the cytoplasmic domain of the p60 receptor is sufficient to bind p60-TRAK activity. Again, the importance of the residues found within the death domain in binding p60-TRAK suggests that the kinase activity correlates with signaling by TNF. The regions of the cytoplasmic domain necessary for binding receptor-associated molecules is depicted in FIG. 14. Ligand-induced conformational changes within the intracellular domain may bring about the unmasking of the aggregation domain and provide the surface for binding of the kinase as described here. The C-terminal 30 residues impede the binding of p60-TRAK.

EXAMPLE 29
Cell Culture and Media

The histiocytic lymphoma cell line U-937 (CRL 1593) was obtained from the American Type Culture Collection (Rockville, Md.) and maintained in a 5% $CO_2$ atmosphere at 37° C. in RPMI-1640 medium (BioWhittaker) supplemented with 10% fetal bovine serum (GIB CO) and penicillin-streptomycin (GIB CO).

EXAMPLE 30
Construction of Plasmids

Plasmids encoding GST-p49$^{wee1}$ and GST-cdc25c have been previously described (Parker and Piwnica-Worms, 1992b) and were a gift of H. Piwnica-Worms. The plasmid pCMV-cdc2 containing a 1.8-kb HINDIII fragment of the full length human cDNA for cdc2 was a gift of J. Smith. To generate pGEM3zf-cdc2, the 1.8-kb HINDIII fragment from pCMV-cdc2 was inserted into HindIII digested pGEM3zf. The orientation of pGEM3zf-cdc2 was determined by BamHI digestion. The plasmid pAGA-cdk2 was a gift of J. Harper.

All plasmids encoding GST-p60 cytoplasmic domain deletions have been described above. The plasmids encoding site-directed mutants of GST-p60$\Delta 8^{T329A}$, GST-p60$\Delta 8^{Y331F}$ and GST-p60$\Delta 8^{T329A/Y331F}$ were generated by PCR using pCMVXVBpL4-p60 as the template and the following primers: $\Delta 8^{T329A}$ (5'-BamHI): CTAAGAGGATC-CACTGATGACCCCGCGGCGCTGTAC (SEQ.ID.NO.9); $\Delta 8^{Y331F}$ and $\Delta 8^{T329A/Y331F}$ (5'-BamHI): CTAAGAGGATTCACTGATGACCCCGCGG/ACGCTGTTCGCCGTGG (SEQ.ID.NO.10); and for all $\Delta 8$ mutants (3'-HindIII): TCTTAGAAGCTTTTAGCGGAG-CACGCGTCCCAG (SEQ.ID.NO.11). The PCR products were digested with BamHI-HindIII and inserted into pGEX2TH. The creation of a KspI site (underlined) in the primers made positive selection for the site-directed mutants possible.

EXAMPLE 31
Expression and Purification of GST Fusion Proteins

Expression of all GST fusion proteins from BL21 cells harboring the appropriate expression vector was induced with 0.5 mM IPTG at 15° C. for 1 hour and purified on glutathione-agarose beads as previously described above. The fusion proteins were stored at 4° C. on glutathione-agarose beads as a 50% slurry in Buffer A (20 mM Tris, pH 8.0, 200 mM NaCl, 10% glycerol, 0.5% NP-40, 1 mM PMSF, 2 µg/ml aprotinin, 2 µg/ml leupeptin, and 0.1% 2-mercaptoethanol) unless otherwise stated. The amount of fusion protein was estimated by Coomassie Blue staining of SDS-PAGE gels.

Generation of p49$^{WEE1}$ from GST-p49$^{WEE1}$ was performed using purified thrombin (obtained from J. Ferton). Approximately 150 µg of GST-p49$^{WEE1}$ attached to glutathione-agarose beads was cleaved in 300 µl of thrombin cleavage buffer (50 mM Tris, pH 8.0, 150 mM NaCl, 2.5 mM $CaCl_2$, and 0.1% 2-mercaptoethanol) with 0.3 µg of thrombin for 30 minutes at room temperature. Reaction mixtures were centrifuged, the supernatants were collected, and the pellets were treated with 0.3 µg of thrombin for a second time. The pellets were washed with 150 µl of Buffer A two times and added to the collected supernatant, and glycerol was added to 10%. This fraction (approximately 1 ml) was then incubated with excess glutathione agarose beads to bind any excess GST or uncleaved GST-p49$^{WEE1}$ in the purified fraction. The purified p49$^{wee1}$ was stored at –20° C. The purified p49$^{WEE1}$ cross-reacted with antibodies directed against p49$^{WEE1}$ (Santa Cruz).

EXAMPLE 32
Antibodies

To obtain antibodies directed against the cytoplasmic domain of the p60 TNF receptor, GST-p60$\Delta 3$ was purified as described above and eluted from glutathione-agarose using 20 mM glutathione in 20 mM Tris (pH 8.0), 150 mM NaCl, 0.1% SDS, 0.5% NP-40. The eluted protein (50 µg/ml) was used to immunize rabbits. The antibodies were affinity purified by elution with 100 mM glycine (pH 2.0) from PVDF membranes that were immobilized with GST5 p60$\Delta 1$ after preparative SDS-PAGE. The affinity-purified p60 TNF receptor antibody detected the endogenous p60 TNF from U937 cells by western blotting and by immunoprecipitation of $^{35}$S-labeled cells. Affinity purified rabbit polyclonal antibodies directed against p49$^{WEE1}$, cdk2, cdk4, and cyclin $D_1$ and monoclonal antibodies to cdc2, cyclin A, cyclin $B_1$, and cyclin E were purchased from Santa Cruz.

EXAMPLE 33
Electrophoretic Mobility Shift Assay (EMSA)

U937 cells ($2 \times 10^6$ cells/ml) were treated separately with different concentrations of the given activator at 37° C. Nuclear extracts (NE) were prepared. EMSA were performed by using 4 mg of NE with $^{32}$p end-labeled double-stranded NF-kB oligonucleotide from the human immunodeficiency virus-1 long terminal repeat (5'-TTGTTACAAGGGACTTTCGCTGGGGACTTTCCAG-GGAGGCGTGG-3'(SEQ.ID.NO.12)) in the presence of 2–3 mg of poly (dI-dC) in a binding buffer (25 mM HEPES pH 7.9, 0.5 mM EDTA, 0.5 mM DTT, 1% NP-40, 5% glycerol, and 50 mM NaCl) for 15 minutes at 37° C. The DNA protein complex formed was separated from free oligonucleotide on 4.5% native polyacrylamide gel using an electrophoresis buffer containing 50 mM Tris, 200 mM glycine pH 8.5, and 1 mM EDTA, and the dried gel was analyzed by a PhosphorImager (Molecular Dynamics, Sunnyvale, Calif.). A mutated oligonucleotide (5'-TTGTTACAACTCATTTCCGCTGCTCACTTTCCAG-GGAGGCGTGG-3'(SEQ.ID.NO.13)) sequence was used to examine the specificity of DNA binding of NF-kB. For supershift assay, the indicated antibodies were incubated with the reaction mix for 15 minutes at room temperature prior to analyzing the NF-kB by EMSA.

EXAMPLE 34
Western Blotting and Immunoprecipitations

U937 cell extracts were processed for in vitro binding as outlined below. After SDS-PAGE, samples were electrophoretically transferred to Immobilon membranes (Millipore) using standard techniques. The membranes were blocked with 5% non-fat dry milk in PBS with 0.5% Tween 20 (PBST). After incubation with the appropriate primary antibody and goat anti-rabbit or goat anti-mouse conjugated to horseradish peroxidase for 40 minutes each, the membranes were washed 4×10 minutes with PBST and developed using the ECL Kit (Amersham).

EXAMPLE 35
In Vitro Kinase Assays

Standard kinase assays were carried out for 20 minutes at 37° C. in 30 µl containing 20 mM HEPES, pH 7.4, 10 mM $MgCl_2$, 0.2 mM ATP, 0.2 mM NaF, 0.1 mM sodium orthovanadate, and 10 µCi [g-$^{32}$P]ATP with the addition of 5 µg histone H1 (Boehringer-Mannheim) or 0.2 µg of pRB$^{110}$ (provided by Canji, Inc.). Reactions were terminated with 15 µl SDS-sample buffer, boiled for 5 minutes, and subjected to SDS-PAGE. Protein bands were visualized by staining with Coomassie blue, and the dried gels were analyzed by a Phosphorimager (Molecular Dynamics) and when appropriate quantitated by ImageQuant Software (Molecular Dynamics).

EXAMPLE 36
In Vitro Binding Assays with GST Fusion Proteins

U-937 cells were lysed in 600 µl of lysis buffer (20 mM HEPES, pH 7.4, 0.1% NP-40, 250 mM NaCl, 10 mM NaF, 1 mM PMSF, 2 µg/ml aprotinin, and 2 µg/ml leupeptin) on ice for 30 minutes followed by a 10-minutes centrifugation in a microfuge. The supernatant was adjusted to 125 mM NaCl by addition of lysis buffer without NaCl, and precleared with 10 µg of GST bound to glutathione-agarose beads for 1 hour at 4° C. The precleared supernatant was mixed with approximately 5 µg GST or the appropriate fusion protein attached to glutathione-agarose beads for 1 hour at 4° C. The beads were collected by centrifugation and washed extensively with lysis buffer (4×500 µl) and with kinase buffer (2×500 µl: 20 mM HEPES, pH 7.4, 10 mM NaF, and 0.1% 2-mercaptoethanol). The pellets were either processed for in vitro kinase assays or boiled in SDS-sample buffer.

EXAMPLE 37
Preparation of Pervanadate

A stock solution of 40 mM pervanadate was prepared by mixing 20 µl of 1M sodium orthovanadate with 10 µl of 30% hydrogen peroxide in a final volume of 110 µl for 15 minutes at room temperature. Fifty microliters of 1M Tris, pH 7.4 and 50 µl of 1M HEPES, pH 7.4 were added and the volume adjusted to 500 µl. The pH was adjusted to 7.4 by addition of 2 µl of concentrated HCl. Catalase (2 µg) (Sigma) was added and the reaction proceeded for 10 minutes at room temperature. Then an additional 2 µg of catalase was added for 30 minutes, after which the reaction was placed on ice. Pervanadate was made fresh each time.

EXAMPLE 38
In Vitro Binding Assays with Labeled Cdks $^{35}$S-labeled proteins were generated by the TNT coupled reticulocyte lysate system (Promega) using either SP6 or T7 polymerase and the appropriate plasmid in a volume of 50 µl for 2 hr at 30° C., and diluted with 200 µl binding buffer (see below). For each in vitro binding reaction, 25 µl of glutathione-agarose beads bound to the appropriate GST fusion protein (~4 µg) was blocked for 30 minutes at room temperature in 400 µl of blocking buffer (20 mM HEPES, pH 7.4, 50 mM KCl, 0.1% NP-40, and 0.5% BSA). The beads were collected by brief centrifugation and resuspended in 400 µl of binding buffer (20 mM HEPES, pH 7.4, 200 mM NaCl, 0.1% NP-40, and 0.1% BSA), and 10 µl of the appropriate $^{35}$S-labeled protein was added and incubated at room temperature for 30 minutes. The beads were collected by centrifugation and washed 4 x in 400 µl of wash buffer (20 mM HEPES, pH 7.4, 200 mM NaCl, and 0.1% NP-40). Proteins were then subjected to SDS-polyacrylamide gel electrophoresis and exposed to a PhosphorImager plate.

EXAMPLE 39
Results

Figure 15:
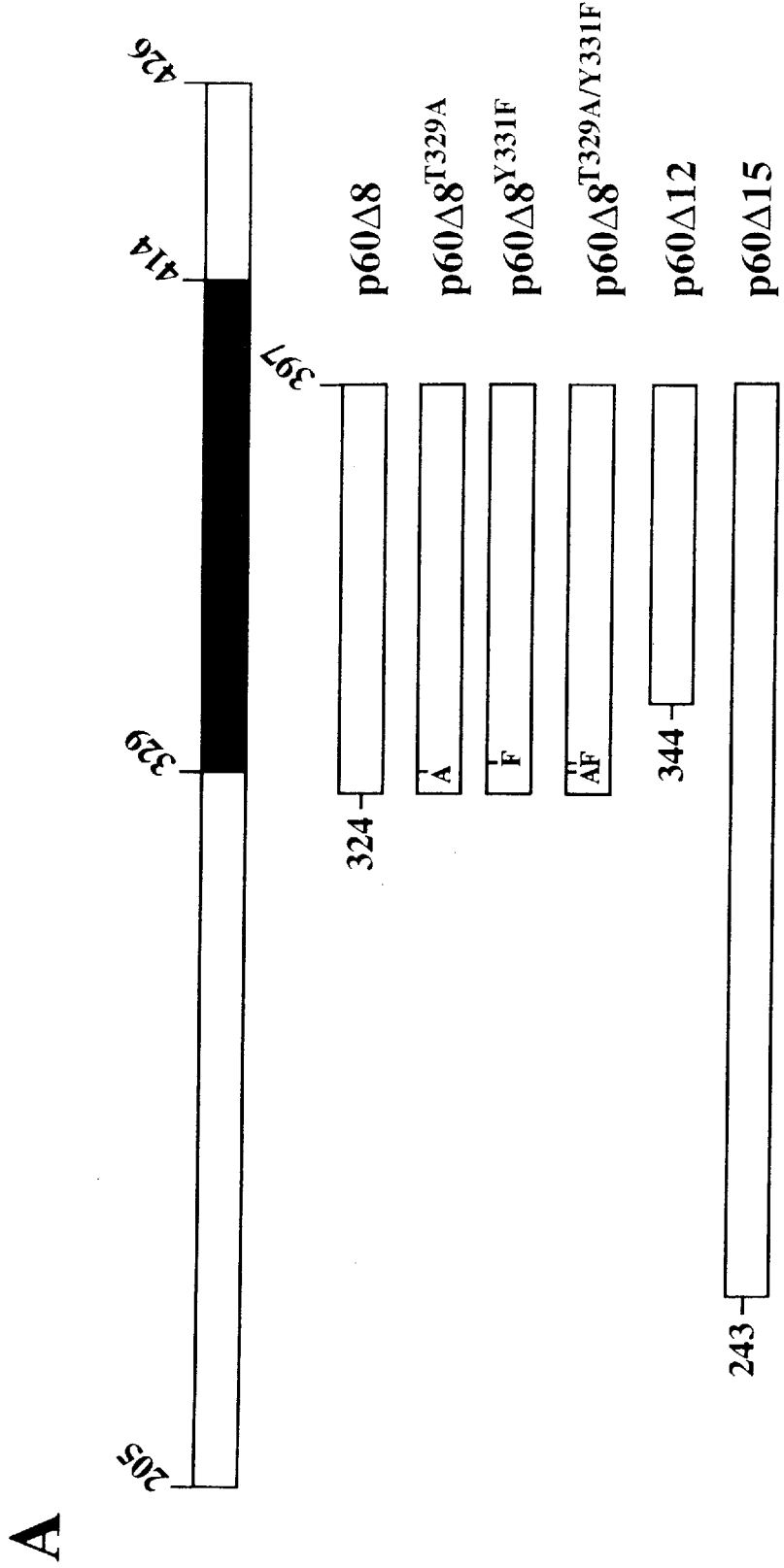
FIG. 15 shows the deletions of the cytoplasmic domain of the p60 TNF receptor.
Figure 15:
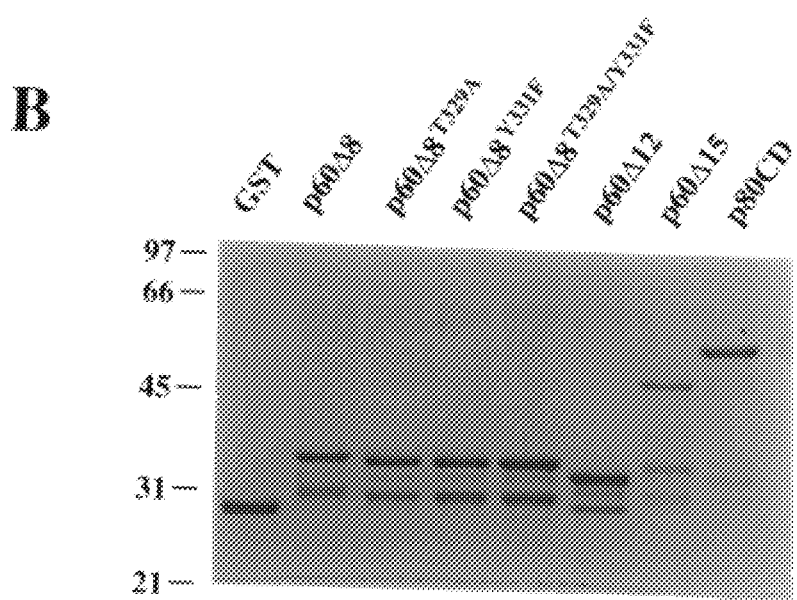

A serine/threonine protein kinase associates with the cytoplasmic domain of the p60 TNF receptor, designated p60TRAK for TNF receptor-associated kinase. In addition, by deletion analysis the binding region of p60TRAK was further defined to residues 344–397 of the death domain. A region termed KID (kinase inhibitory domain) was also identified comprising residues 397–426 that inhibits the association of p60TRAK. For the present invention, GST fusion proteins of the cytoplasmic region of the p60 receptor that comprise deletions Δ8, Δ12, and Δ15 were used, all of which lack the kinase inhibitory domain but contain the death domain (FIG. 15A). These three deletion mutants, however, differ in their N-terminus and thus in their size, which allowed distinguishing them from other substrates used. A Coomassie Blue stained SDS-polyacrylamide gel of the GST fusion proteins used is shown in FIG. 15B.

EXAMPLE 40
Amino Acid Sequence of the p60 Cytoplasmic Domain Exhibits Homology to Cyclins Since the data above indicated that p60TRAK bound to residues 344–397 of the cytoplasmic domain of the p60 TNF receptor, serine/threonine kinases were searched for that could potentially bind to this sequence of amino acids. On close examination, a strong homology was found between the cyclins and the cytoplasmic domain of the p60 TNF receptor (FIG. 16). While cyclins B, $D_1$, and E share 50%, 40%, and 40% homology with cyclin A, respectively (Hadwiger et al., 1989), the cytoplasmic domain of the p60 TNF receptor shares 31% (33 out of 108 residues) and 50% (54 out of 108 residues) homology with cyclin A and all other cyclins, respectively. The recent crystallographic analysis of the structure of cyclin A-cyclin-dependent kinase (cdk)-2 complex indicates that their interface buries a significant amount of surface area (3550 Å$^2$) due to approximately 25 hydrophobic residues and 17 intramolecular hydrogen bonds. This is in contrast to typically only 1500 Å$^2$ area buried in antibody-protein complexes (Davies et al., 1990; Jeffrey et al., 1995). Besides amino acid sequence homology, the results from the crystal structure indicate the formation of a tight complex between cyclin A and cdk2 and support that the intracellular domain of p60 receptor is tightly coupled with p60TRAK. Since cyclins are the activating subunit of cyclin-dependent kinases, it is possible that p60TRAK is one of the CDKs.

Figure 17:
FIG. 17 shows the association of Cdk2 with the p60 TNF receptor in vitro and in vivo.
Figure 17:
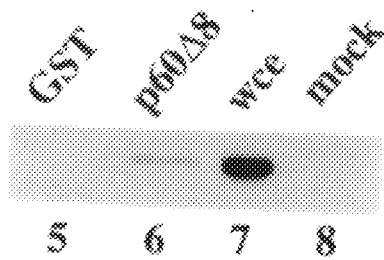
Figure 17:
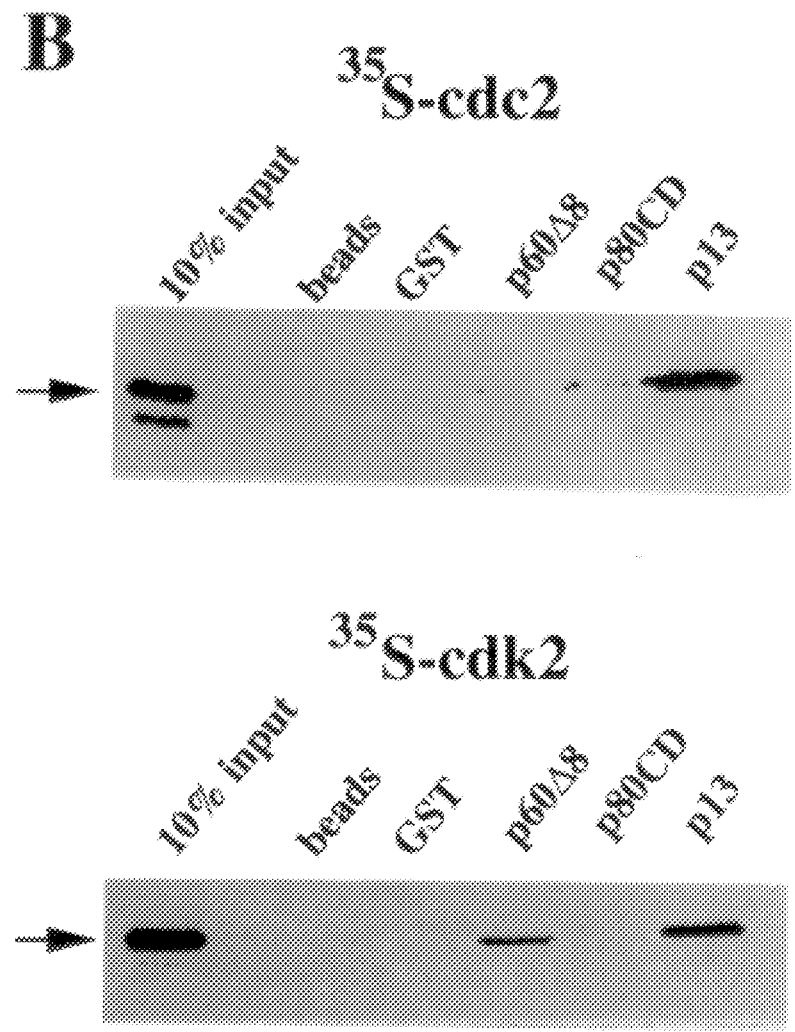
Figure 17:
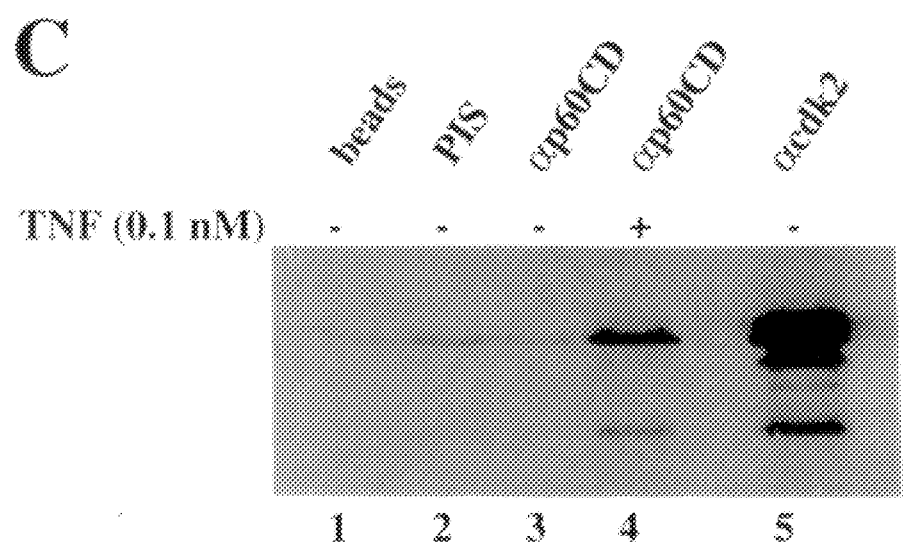

EXAMPLE 42
Endogenous Cdk2 Binds to the Cytoplasmic Domain of the p60 Receptor To demonstrate that an endogenous CDK binds to the intracellular domain of the p60 receptor, GST-p60Δ8 were used for affinity precipitations of U937 cell lysates, followed by SDS-polyacrylamide gel electrophoresis and immunoblotting with affinity-purified antibodies directed against cdc2 and cdk2. An immunoreactive band corresponding to endogenous cdk2 was observed in precipitates from GST-p60Δ8 (FIG. 17A, lane 6). As a control, none of the cyclin-dependent kinases bound to GST (FIG. 17A, lanes 1 and 5). In addition, the cdk2 immunoreactive band was found in the precipitates of GST-p60Δ8 from U937 cells but was absent in a mock reaction without U937 cell lysates (FIG. 17A, lane 8). Thus, a GST fusion protein containing the cytoplasmic domain of the p60 TNF receptor bound to endogenous cdk2.

EXAMPLE 43
In Vitro Translated Cdk2 Associates with the p60 Cytoplasmic Domain

To demonstrate further that the interaction of the p60 cytoplasmic domain with cdk2 is specific, both cdc2 and cdk2 were labeled with [35S]methionine by in vitro transcription and translation and examined for their ability to associate with GST fusion proteins immobilized on glutathione agarose. As expected, both labeled cdc2 and cdk2 could be precipitated with p13$^{suc1}$-agarose (FIG. 17B). Only labeled cdk2 associated with GST-p60Δ8 under the binding conditions employed (FIG. 17B, bottom). Neither labeled cdc2 nor cdk2 associated with the beads, GST, or GST-p80CD (FIG. 17B). However, under less stringent binding and washing conditions, labeled cdc2 bound weakly to GSTp60Δ8 (data not shown). Thus, while both cdc2 and cdk2 represent part of a family of cyclin-dependent protein kinases, the cytoplasmic domain of p60 bound to cdk2 in vitro.

EXAMPLE 44
Binding of Cdk2 to the Endogenous p60 TNF Receptor is Stimulated by TNF The data presented above indicates that endogenous or in vitro translated cdk2 associates with the p60 cytoplasmic domain. Since co-immunoprecipitation was not feasible due to interference by immunoglobulin heavy and light chains, a technique previously described for the in vivo interaction of E1a with the retinoblastoma protein (Dyson et al., 1989) was utilized. To demonstrate that cdk2 associates with the endogenous, activated p60 TNF receptor, an experiment was performed in which in vitro translated $^{35}$S-labeled cdk2 was mixed with the cell lysate prior to immunoprecipitation with an affinity-purified antibody to the p60 TNF receptor. U937 cells were left untreated or treated with 1 nM TNF for 5 minutes and lysed, $^{35}$S-labeled cdk2 was added to the lysates, and then protein A sepharose beads, preimmune serum, anti-p60 receptor antibodies, or anti-cdk2 antibodies were added. As a control anti-cdk2 antibodies precipitated the labeled cdk2 when it was mixed with the cell lysate (FIG. 17C, lane 5). Labeled cdk2 was precipitated by the anti-p60 receptor antibodies only from cells that were treated with TNF (FIG. 17C, lane 4); quantitation indicated a 10-fold increase in binding to the activated p60 TNF receptor. As discussed above, a KID exists near the C-terminus of the cytoplasmic domain of the p60 TNF receptor. Thus, the observation that the endogenous p60 TNF receptor binds to cdk2 only in the presence of TNF is in agreement with the hypothesis that TNF-induces a conformational change within the cytoplasmic domain that unmasks the aggregation domain and provides a binding surface for cdk2.

EXAMPLE 45
p60TRAK Activity is Depleted by p13$^{Suc1}$

Figure 18:
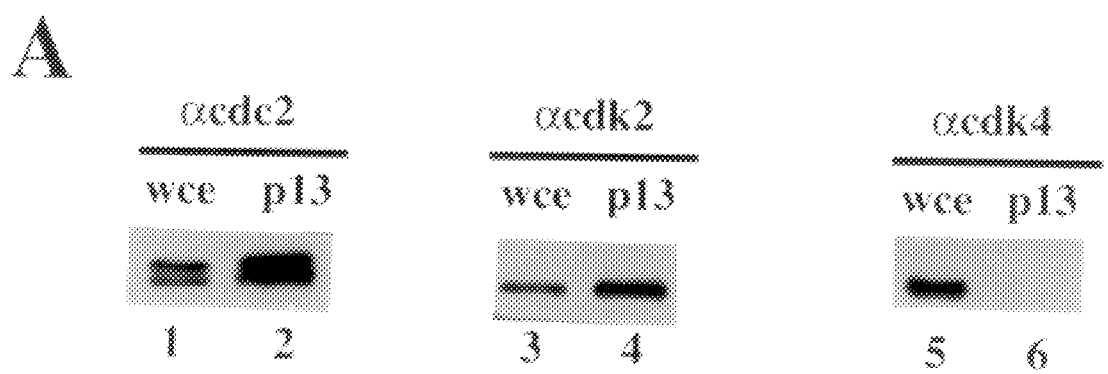
FIG. 18 shows the depletion of p60TRAK activity by p13$^{suc1}$ agarose.
Figure 18:
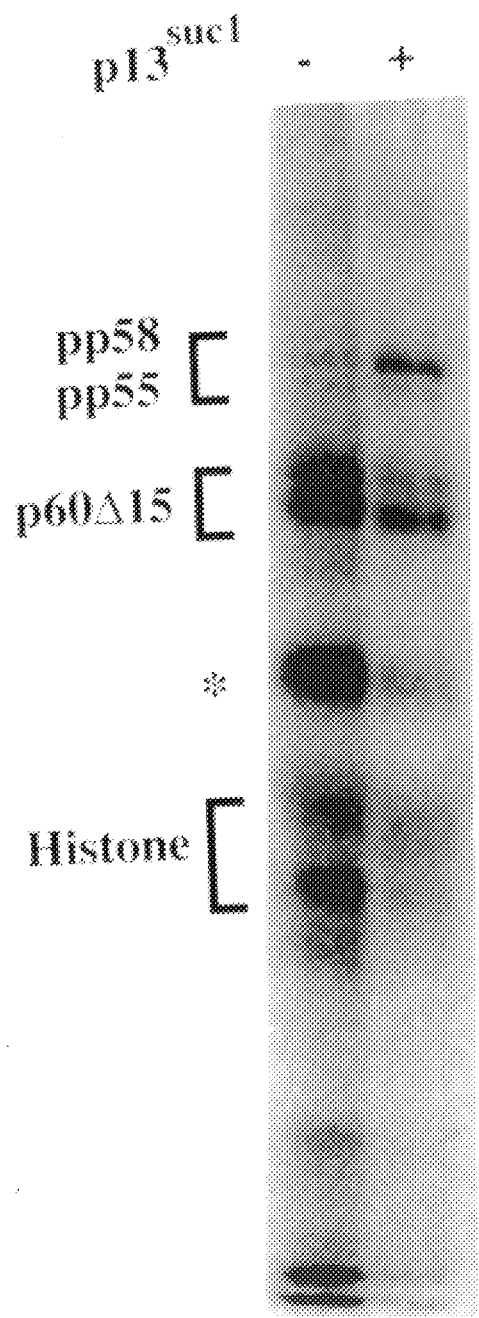
Figure 18:
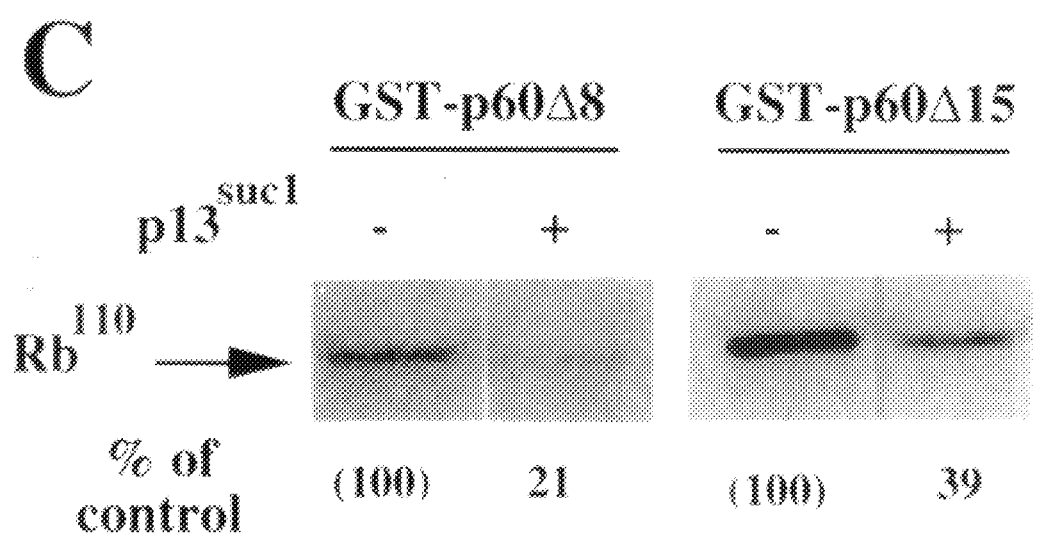

One characteristic of various CDKs is that they physically associate with a small molecular weight protein known as p13$^{suc1}$, the yeast equivalent of human CksHs1 and CksHs2 (Brizuela et al., 1987; Parge et al., 1993; Richardson et al., 1990). Even though western blotting of whole cell extracts indicated that all the three cdks were present in the U937 cell lysates (FIG. 18A, lanes 1, 3, and 5), immunoblotting of p13$^{suc1}$-agarose precipitates from U937 cell extracts with specific antibodies to CDKs showed that only cdc2 and cdk2, but not cdk4, bound to p13$^{suc1}$-agarose (FIG. 18A, lanes 2, 4, and 6).

Since p13$^{suc1}$-agarose bound cdc2 and cdk2, whether p13$^{suc1}$-agarose could deplete the p60TRAK activity associated with the p60 cytoplasmic domain was examined. As GST-p60Δ8 migrates at the same molecular weight as histone H1, GST-p60Δ5 which is indistinguishable from GST-p60Δ8 with respect to p60TRAK binding, was used. U937 cell lysates were either incubated with GST bound to glutathione agarose or p13$^{suc1}$-agarose, and the supernatant was used in affinity precipitations with GST-p60Δ15. The kinase activity that remained bound to GST-p60Δ15 was measured with histone H1. The p13$^{suc1}$-agarose depleted p60TRAK activity toward histone H1 and GST-p60Δ15 by 50% (FIG. 18B). Additionally, phosphorylation of the retinoblastoma protein (Rb$^{110}$) by p60TRAK after depletion with p13$^{suc1}$-agarose was reduced by greater than 60%, indicating p60TRAK activity was indeed decreased in cell lysates depleted with p13$^{suc1}$-agarose (FIG. 18C). That p13$^{suc1}$-agarose precipitated cdc2 and cdk2, but not cdk4, indicated that p60TRAK activity is most likely due to either cdk2 or cdc2. However, these observations as shown above suggest that it is cdk2 and not cdc2 that interacts with the TNF receptor. This is consistent with the observation that the TNF-activated, endogenous p60 TNF receptor bound cdk2.

EXAMPLE 46
Pervanadate Treatment of Cells Modulates p60TRAK Activity

A serine kinase involved in the activation of NF-kB by TNF is down-regulated by inhibitors of protein tyrosine phosphatases.

These inhibitors are known to increase the tyrosine phosphate content in cellular proteins. Since CDKs are negatively regulated by tyrosine phosphorylation, it is plausible that p60TRAK is also down-regulated by these inhibitors.

Figure 19:
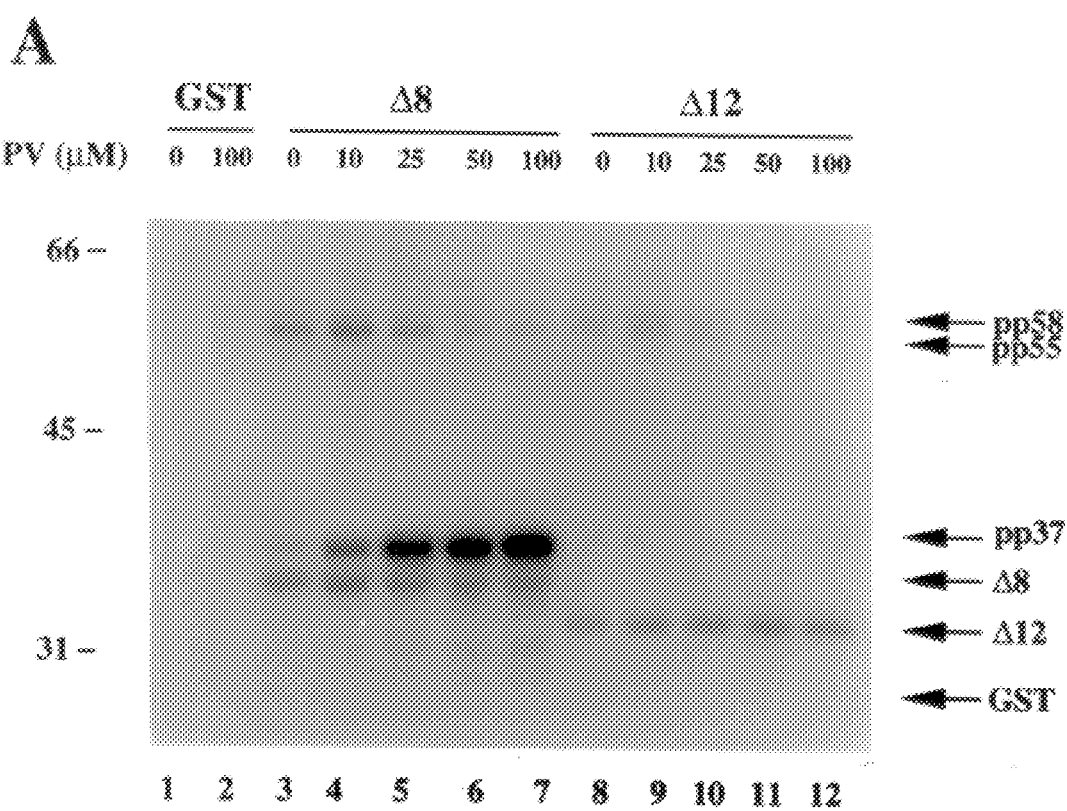
FIG. 19 shows the pervanadate modulates the activity of p60TRAK.
Figure 19:
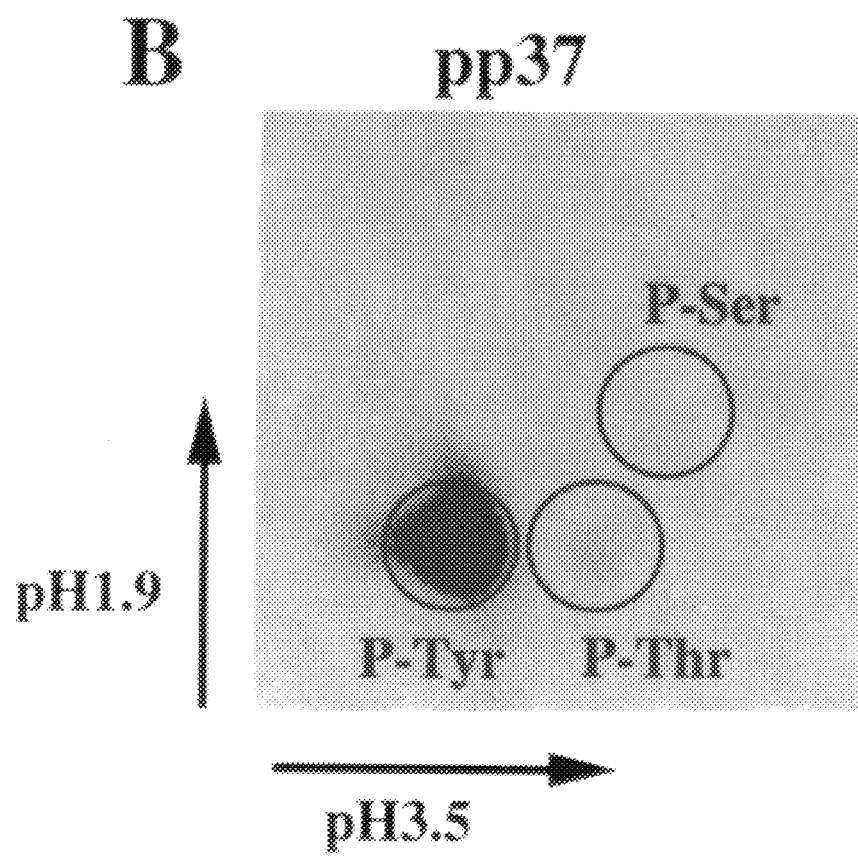

U937 cells were treated with various concentrations of pervanadate for 30 minutes and performed affinity precipitations of cell lysates with either GST, GST-p60Δ8, or GST-p60Δ12 followed by in vitro kinase assays. Pervanadate treatment decreased phosphorylation of the two associated proteins, designated pp58 and pp55, in both precipitates of GST-p60Δ8 and GST-p60Δ12 (FIG. 19A, lanes 3–7 and 8–12). However, increasing concentrations of pervanadate increased phosphorylation of a protein, designated pp37, that appeared only in precipitates containing GST-p60Δ8 (FIG. 19A, lanes 3–7), indicating that pp37 may be a slower migrating form of GST-p60Δ8 (see below). In controls, the phosphorylation of GST-p60Δ8 by p60TRAK from untreated cells remained the same when pervanadate was used directly in the kinase assay (data not shown). The decreased phosphorylation of pp58 and pp55 and the increased phosphorylation of pp37 could be explained by a mechanism in which a second kinase associates with the p60 cytoplasmic domain that negatively regulates p60TRAK, thus decreasing phosphorylation of pp58 and pp55. Since pervanadate inhibited protein tyrosine phosphatase activity and increased total cellular tyrosine phosphate content (Menon et al., 1995; data not shown), it was conceivable that the same second kinase that negatively regulates p60TRAK also caused an increased phosphorylation of pp37. If so, the phosphorylation of pp37 must occur at a tyrosine residue.

EXAMPLE 47
Cytoplasmic Domain of the p60 TNF Receptor Undergoes Phosphorylation on Tyrosine The phosphorylation of pp37 was observed only in precipitates from pervanadate-treated cells with GST-p60Δ8. Since pp37 can be cleaved from GST by thrombin (data not shown), it was concluded that pp37 was a slower migrating form of the cytoplasmic domain of the TNF receptor. The phosphoamino acid analysis of pp37 indicated phosphorylation on tyrosine residue (FIG. 19B). This is the first time that tyrosine phosphorylation of the cytoplasmic domain of the p60 TNF receptor has been reported.

The deletion protein p60Δ8 contains a single tyrosine residue ($Y^{331}$) that is not present in p60Δ12 (FIG. 19C). A literature search indicated that GTYGVV (SEQ.ID.NO.16), a sequence similar to the one comprising $Y^{331}$ (ATLYAVV (SEQ.ID.NO.17)), is a potential site for phosphorylation by the WEE1 kinase (Nigg, 1995). The WEE1 kinase from yeast is a dual-specificity kinase (Featherstone and Russell, 1991; Haese et al., 1995; Parker et al., 1992a), whereas the human WEE1 kinase is specifically a tyrosine kinase (McGowan and Russell, 1995; Parker and Piwnica-Worms, 1992b; Watanabe et al., 1995).

To demonstrate that $Y^{331}$ is a potential site for phosphorylation, $Y^{331}$ of GST-p60Δ8 was replaced with phenylalanine by site-specific mutagenesis. Two additional mutants were also made: in one, $T^{329}$ was replaced with alanine and in the other, a double mutant was made that contained both substitutions. These three mutant fusion proteins and wild-type GST-p60Δ8 were used in affinity precipitations of cell lysates from control and pervanadate treated cells followed by in vitro kinase assays. pp37 did not appear in pervanadate-treated cell extracts that had been affinity precipitated with GST-p60Δ8$^{Y331F}$ or GST-p60Δ8$^{T329A/Y331F}$ (FIG. 19D, lanes 6 and 8) but it did appear in those precipitated with both GST-p60Δ8 (FIG. 19D, lane 2) and GST-p60Δ8$^{T329A}$ (FIG. 19D, lane 4). In addition, as observed earlier with pervanadate treatment (FIG. 19A, lanes 3–7), the extent of phosphorylation of pp58 and pp55 decreased with p60TRAK bound to either GST-p60Δ8 or its mutants (FIG. 19D). The mutations did not affect binding of p60TRAK to the cytoplasmic domain since the extent of phosphorylation of the fusion proteins was similar in untreated cells (FIG. 19D, lanes 1, 3, 5, and 7). Thus, these results suggest that there is a specific tyrosine site on the cytoplasmic domain of the p60 TNF receptor that undergoes phosphorylation.

Since the site of tyrosine phosphorylation in the p60 cytoplasmic domain is a putative site for phosphorylation by WEE1, whether GST-p60Δ8 could be phosphorylated by WEE1 in vitro was examined. Bacterial expressed and purified p49$^{WEE1}$ phosphorylated both GST-p60Δ8 and GST-p60Δ8$^{T329A}$, but not GST or the mutant GST-p60Δ8$^{Y331F}$ (FIG. 19E). In addition, the dual-specificity protein phosphatase cdc25, which has been implicated in the dephosphorylation of both $T^{14}$ and $Y^{15}$ of p34$^{cdc2}$ (Gautier et al., 1991; Lee et al., 1992; Millar et al., 1991; Parker and Piwnica-Worms, 1992b), dephosphorylated GST-p60Δ8 that had been phosphorylated by p49$^{WEE1}$ (FIG. 19F). It has been shown that cdc25 serves as one of the substrates for CDKs (Hoffmann et al., 1993; Hoffmann et al., 1994; Izumi and Maller, 1993). Similarly, GST-cdc25 is also phosphorylated in vitro by p60TRAK (unpublished data), thus again suggesting that p60TRAK is similar to CDKs.

Thus, the present invention indicates that a WEE1-like tyrosine kinase functionally associates with the cytoplasmic domain of the p60 TNF receptor that phosphorylates $Y^{331}$ only when protein tyrosine phosphatase activity is inhibited. The present invention also suggest that this tyrosine kinase could play a negative role in regulating the p60TRAK. However, whether the tyrosine kinase associated directly with the cytoplasmic domain or indirectly via binding of p60TRAK or another adaptor protein was not determined.

EXAMPLE 49
Exogenous p49$^{WEE1}$ Inhibits p60TRAK $Y^{331}$ of the p60 cytoplasmic domain was phosphorylated only if the cells were treated with pervanadate, which itself decreased p60TRAK activity. Since WEE1 is known to negatively regulate CDK activity, whether exogenous human WEE1 could inactivate p60TRAK activity was examined. The histone kinase activity of p60TRAK was inhibited by at least 70% in the presence of p49$^{WEE1}$ kinase in untreated cells (FIG. 20A, lanes 1 and 2). Similar to p49$^{WEE1}$, pervanadate treatment of cells also reduced histone kinase activity by 55% (FIG. 20A, compare lanes 1 and 4). Hence, the addition of exogenous p49$^{WEE1}$ tyrosine kinase modulated the activity of p60TRAK.

Since both pervanadate treatment and exogenous p49$^{WEE1}$ inhibited p60TRAK activity, whether pervanadate treatment could inhibit cdk2 activity was shown. A treatment for 30 minutes with 100 μM pervanadate inhibited greater than 70% of histone H1 kinase activity immunoprecipitated with a cdk2 antibody (FIG. 20B). Additionally, as expected p49$^{WEE1}$ inhibited histone kinase activity of cdk2-cyclin A in vitro (data not shown) and of cdc2-cyclin B (Parker and Piwnica-Worms, 1992b). The human WEE1 tyrosine kinase phosphorylates cyclin A, B1, and E-associated cdk2 and cdc2 on $Y^{15}$ in vivo, but not cyclin D1-associated kinase cdk4 (Watanabe et al., 1995). This is consistent with the fact that tyrosine phosphorylation of cyclin D1-associated kinase cdk4 has not been detected in vivo (Kato et al., 1994; Matsushime et al., 1994). Besides WEE1 kinase, the Src-family related tryosine kinases has also been shown to phosphorylate a peptide that contains $Y^{15}$ of cdc2 in vitro (Cheng et al., 1992). Like WEE1, the tyrosine kinase activity precipitated with GST-p60Δ8 from pervanadate-treated cells did not phosphorylate enolase, a common substrate for the src protein kinases (data not shown; Parker and Piwnica-Worms, 1992b). Taken together, these data demonstrate that the tyrosine kinase activity associated with the p60 cytoplasmic domain is either WEE1 or a WEE1-like kinase that negatively regulates p60TRAK.

EXAMPLE 50
p60TRAK is Positively Regulated by Serine/Threonine Phosphorylation

Since CDKs are not only negatively regulated by tyrosine phosphorylation, but also positively regulated by threonine phosphorylation, whether p60TRAK is regulated by serine/threonine phosphorylation was shown. An identical experiment was performed as that described for pervanadate (FIG. 19A), except various concentrations of okadaic acid, an inhibitor of serine/threonine phosphatase type 2A and type 1 (Goris et al., 1989), were used. In contrast to pervanadate treatment, okadaic acid treatment caused a dose-dependent increase in phosphorylation of GST-p60Δ8 and GSTp60Δ12 (FIG. 21A). The extent of phosphorylation of pp58 and pp55 also increased, but pp37 was not observed (FIG. 21A). In controls, okadaic acid by itself had no direct effect in the kinase assay (data not shown). Although okadaic acid activated p60TRAK activity, when incubated in the presence of p49$^{WEE1}$, it inhibited at least 50% of the histone kinase activity of p60TRAK (FIG. 20A, compare lanes 1, 7, and 8). Thus, like cdk2, the phosphorylation of p60TRAK at serine/threonine and at tyrosine residues together leads to net inactivation of the kinase activity.

The increase in p60TRAK activity by okadaic acid might have been due either to an increase in p60TRAK binding or to positive regulation of p60TRAK itself by phosphorylation at serine/threonine. To distinguish between these two possibilities, affinity precipitations were performed with GST-p60Δ8 from cells treated in the absence or presence of 0.6 μM okadaic acid. The precipitated p60TRAK was washed, and a phosphatase assay was performed with 10 μg of cell lysates prepared either in the presence or absence of phosphatase inhibitors. After the phosphatase assay, the precipitated p60TRAK was washed and in vitro kinase assays were performed in the presence of [g $^{32}$P]ATP. GST-p60Δ8 phosphorylation by p60TRAK from okadaic acid-treated cells was similar to that in untreated cells when extracts prepared in the absence of phosphatase inhibitors were mixed with the precipitated p60TRAK in the phosphatase assay (FIG. 21B, lanes 3 and 4). However, when lysates prepared in the presence of phosphatase inhibitors were mixed with the precipitated p60TRAK in the phosphatase assay, the amount of GST-p60Δ8 phosphorylation from untreated and okadaic acid-treated cells was indistinguishable from the mock phosphatase assay (FIG. 21B, compare lanes 5 and 6 with lanes 1 and 2). These results suggest that okadaic acid inhibits the dephosphorylation of p60TRAK and thus increases the kinase activity of p60TRAK.

Unlike p60TRAK, the p80 TNF receptor-associated kinase (p80TRAK) was not affected by either pervanadate or okadaic acid treatment, indicating that these two TRAKs differ from each other (unpublished data). These observations suggest that p60TRAK activity is negatively regulated by tyrosine phosphorylation but positively regulated by serine/threonine phosphorylation. Not only was this type of regulation observed for p60TRAK from U937 cells, but similar results were obtained with human foreskin fibroblasts and the breast adenocarcinoma cell line MCF-7. The only kinase known to be regulated in this manner are the CDKs (Nigg, 1995; Morgan, 1995), which are negatively regulated by WEE1 tyrosine kinase and positively by the serine/threonine kinase CAK (cdk2 activating kinase). Thus, these results are consistent with all the other evidence that p60TRAK is a CDK.

EXAMPLE 51
Pervanadate Blocks TNF-Induced Activation of NF-kB

As indicated above, pervanadate inhibits TNF-dependent activation of NF-kB, however in these studies human ML-la cells were used. Pervanadate inhibits TNF activation of NF-kB in the human histiocytic lymphoma cell line, U937, used in the current studies. A dose-dependent reduction of TNF-induced NF-kB activity was observed with increasing concentrations of pervanadate (FIG. 22, lanes 7–11). In contrast, pervanadate alone did not activate NF-kB DNA binding activity (FIG. 22, lanes 2–6) nor did it inhibit the DNA-binding activity of NF-kB to its oligonucleotide when added during the DNA-binding assay. Formation of the NF-kB complex was specific as it could be competed with a 100-fold excess of unlabeled wild-type oligonucleotide (FIG. 22, lane 12), but not with an oligonucleotide containing a mutant NF-kB binding site (FIG. 22, lane 14). The NF-kB complex induced by TNF contained the p50 and p65 subunits as judged by supershifts with affinity-purified antibodies to p50 and p65 (data not shown).

Since pervanadate caused not only inhibition of TNF-induced NF-kB activity but also the down-modulation of p60TRAK activity, it is plausible that p60TRAK is necessary for TNF mediated activation of NF-kB. While induction of NF-kB requires the phosphorylation of IkBα on serines 32 and 36 (Brown et al., 1995; Traenckner et al., 1995) that leads to its subsequent degradation by the ubiquitin pathway and release of NF-kB (Chen et al., 1995; see discussion), it is possible that p60TRAK itself phosphorylates IkBα or regulates a kinase that phosphorylates IkBα, however further analysis of p60TRAK's role in activation of NF-kB remains to be determined.

Thus, the present invention characterized the kinase activity associated with the p60 TNF receptor. Many independent lines of evidence indicate that p60TRAK is cdk2. First, the amino acid sequence of p60 receptor exhibits significant homology to cyclins. Second, both endogenous and in vitro translated cdk2 binds to the p60 cytoplasmic domain. Third, TNF stimulates the binding of cdk2 to the endogenous p60 TNF receptor. Fourth, treatment of cells with pervanadate or okadaic acid either inactivated or activated p60TRAK, respectively, indicating opposing roles of tyrosine and serine/threonine phosphorylation of p60TRAK. Like inhibition of p60TRAK, pervanadate inhibited endogenous cdk2 histone kinase activity. Fifth, exogenous bacterial expressed human p49$^{WEE1}$ tryosine kinase inhibited the activity of p60TRAK. Sixth, like cdk2, p13$^{suc1}$-agarose depleted p60TRAK activity from cell lysates. Based on all these evidence it appears that p60TRAK is cdk2. A summary of its regulation is illustrated in FIG. 23.

During the characterization of p60TRAK, it was observed that pervanadate treatment not only caused the association of a WEE1-like tyrosine kinase to inhibit p60TRAK, but also the WEE1-like kinase caused the phosphorylation of Y$^{331}$ of the cytoplasmic domain of the p60 TNF receptor. Furthermore, this site is known to be a consensus site for phosphorylation by the WEE1 tyrosine kinase (Nigg, 1995). It was also demonstrated that Y$^{331}$ is phosphorylated by WEE1 and dephosphorylated by the dual-specificity phosphatase cdc25 in vitro. However, in these studies one could not distinguish whether the WEE-like tyrosine kinase associated directly with the p60 cytoplasmic domain or via p60TRAK. While this is the first indication that the p60 TNF receptor undergoes tyrosine phosphorylation, the consequence of Y$^{331}$ phosphorylation of the p60 TNF receptor and the exact identity of the tyrosine kinase responsible for this activity in vivo remain to be determined. However, the characteristic features of this tyrosine kinase coincide with that of WEE1 (McGowan and Russell, 1995; Parker and Piwnica-Worms, 1992b; Watanabe et al., 1995).

EXAMPLE 52
Does the Cytoplasmic Domain of the p60 TNF Receptor Act as a Cyclins?

Cyclins are required for the activation of cyclin-dependent kinases (Morgan, 1995); however, throughout these studies no known cyclin was found to associate with the cytoplasmic domain of the p60 TNF receptor or with p60TRAK. It is conceivable that the p60 cytoplasmic domain functions as a "cyclin-like" molecule to activate p60TRAK. This is consistent with the highly significant sequence homology noted between the p60 cytoplasmic domain and cyclins (FIG. 16). In addition there are several features of cyclins that are common to the p60 TNF receptor. First, as presented here, the p60 cytoplasmic domain interacts with a cyclin-dependent kinase. Second, the cell surface p60 TNF receptor has been reported to oscillate during the cell cycle (Pocsik et al., 1995). Third, the p60 TNF receptor has been reported to be ubiquitinated (Loetscher et al., 1990). Fourth, like cyclin D (Dowdy et al., 1993; Ewen et al., 1993;

Kato et al., 1993), the p60 TNF receptor contains the characteristic retinoblastoma binding motif, LXCXE (SEQ.ID.NO.18), in the C-terminal region of the cytoplasmic domain (DMDLLGCLEDIEE(SEQ.ID.NO.19));

however, the physiological role of this interaction remains to elucidated. And lastly, overexpression of the p60 death domain leads to cell death (Boldin et al., 1995a), much like overexpression of the cyclin B-cdc2 complex (Shi et al., 1994).

From the structural analysis of the cyclin A-cdk2 complex, the cyclin fold consists of five helices that form a tight packing; the α3 helix forms the hydrophobic core surrounded and the remaining four helices surround it (Jeffrey et al., 1995). The most significant packing interactions involve the conserved alanines at positions 235 and 264 of cyclin A ($A^{328}$ and $D^{357}$ of the p60 cytoplasmic domain) (FIG. 16). Also, small side chain residues of cyclin A including $G^{257}$, $A^{259}$, and $A^{260}$ ($G^{350}$, $S^{352}$, and $D^{353}$ of the p60 cytoplasmic domain) are found at crossing points in the α3 helix (FIG. 16). Although these residues are not well conserved among all cyclins, the compact side chains, which are also found in the p60 cytoplasmic domain, allow for tight packing of the helices.

The N-terminal helix and helices α3, α4, and α5 from cyclin A form the interface between cdk2-cyclin A (Jeffrey et al., 1995). The residues 344–397 of the p60 cytoplasmic domain (ie, p60Δ12) that are necessary for binding p60TRAK correspond to helices α3, α4, and α5 of cyclin A (FIG. 16). Most notably, many of the hydrophobic residues in these three helices are conserved in the cytoplasmic domain of p60 (FIG. 16). Another important interaction involves conserved residues $K^{266}$ and $E^{295}$ of cyclin A ($R^{358}$ and $E^{390}$ of the p60 cytoplasmic domain) that form an extended hydrogen-bonding network with cdk2 (Jeffrey et al., 1995). Additionally, a hydroxyl group of $Y^{185}$ of cyclin A ($Y^{270}$ of the p60 cytoplasmic domain, not shown in FIG. 16) provides a hydrogen bond to $E^{57}$ of cdk2 (Jeffrey et al., 1995). Thus, based on the evidence provided herein and the significant sequence homology found between cyclins and the p60 cytoplasmic domain, the present invention shows that the cytoplasmic domain of the TNF receptor functions like a cyclin to activate p60TRAK.

EXAMPLE 53
What is the Role of Cdk2 in TNF Signaling?

The present invention demonstrated that the binding of cdk2 to the p60 TNF receptor is stimulated by TNF. This interaction could play a role in two known signaling mechanisms of TNF: apoptosis and NF-kB activation. The resemblance of a mitotic catastrophe to apoptosis in eukaryotic cells is indicative of a role for cyclin-dependent kinases in apoptosis (Meikrantz and Schlegel, 1995; Shi et al., 1994). The role for CDKs in TNF signaling has recently been demonstrated (Meikrantz et al., 1994). HeLa cells are typically resistant to TNF; however, when these cells are arrested in S-phase, TNF increased cyclin A-associated kinase activity by threefold, resulting in TNF-induced apoptosis (Meikrantz et al., 1994), indicating cyclin A-associated histone kinase activity is induced by TNF.

It is known that TNF activated NF-kB by phosphorylating two critical serine residues on IkBα (Brown et al., 1995; Traenckner et al., 1995) and targeting it for ubiquitination and degradation by the 26S proteasome (Chen et al., 1995). However, the mechanism of IkBα phosphorylation and ubiquitination is not understood. It is possible that p60TRAK may directly phosphorylate IkBα or regulate a specific IkBα kinase. Alternatively, p60TRAK could regulate one or more of the enzymes participating in ubiquitination of IkBα. The ubiquitin degradation pathway of cyclin B is an example of such regulation in which the ubiquitin protein ligase is activated by the cdc2 protein kinase (Hershko et al., 1994). Pervanadate not only inhibits p60TRAK activity, but also inhibits the degradation of IkBα. Interestingly, the recent identification of a protein related to a proteasomal subunit that binds to the p60 cytoplasmic domain may provide a link between the 26S proteasome and the p60 TNF receptor (Boldin et al., 1995b). It is intriguing that pervanadate inhibits TNF-induced activation of NF-kB, while okadaic acid activates NF-kB (Singh and Aggarwal, 1995). Therefore, it is possible that the same kinase responsible for NF-kB induction undergoes inactivation by pervanadate but activation by okadaic acid. This correlates with the observations herein that these inhibitors modulate p60TRAK activity.

A novel protein termed TRADD was identified by its interaction with the cytoplasmic domain of the p60 TNF receptor in the yeast two-hybrid system (Hsu et al., 1995). TRADD possesses approximately 35% homology to the death domain of the p60 TNF receptor and was shown to bind exclusively to this region (Cleveland and Ihle, 1995; Hsu et al., 1995). Overexpression of TRADD caused both apoptosis and NF-kB activation, two responses mediated by TNF. Since expression of only the death domain (Boldin et al., 1995a) or an intact p60 receptor containing only the death domain (Hsu et al., 1995) leads to NF-kB activation, it is plausible that p60TRAK, which also binds to the death domain, could lead to activation of NF-kB. Further demonstration that p60TRAK activates NF-kB remains to be determined.

This is the first report implicating an association of a CDK with a membrane-bound receptor. Potential downstream targets of p60TRAK could include molecules such as TRADD, TRAP-1, and IkBα as well as the two unidentified proteins, pp58 and pp55. Thus, the precise role of the p60 cytoplasmic domain-cdk2 complex in signaling the multiple responses of TNF remains to be elucidated.

THE FOLLOWING REFERENCES WERE CITED HEREIN

Alkalay, I., et al., Mol. Cell. Biol. 15, 1294–1301, (1995).
Baeuerle, P. A., et al., Annu. Rev. Immunol. 12, 141–179, (1994).
Beg, A. A., et al., Mol. Cell. Biol. 13, 3301–3310, (1993).
Beutler, B., et al., Science 264, 667–668, (1994).
Boldin, M. P., et al., J. Biol. Chem. 270, 387–391, (1995a).
Boldin, M. P., et al., FEBS Lett. 367, 39–44, (1995b).
Brizuela, L., EMBO J. 6, 3507–3514, (1987).
Brown, K., et al., Science 267, 1485–1491, (1995).
Brown, K., et al., Proc. Natl. Acad. Sci. USA 90, 2532–2536, (1993).
Chen, Z., et al., Genes Dev. 9, 1586–1597, (1995).
Cheng, H. C., et al., J. Biol. Chem. 267, 9248–9256, (1992).
Cleveland, J. L., et al., Cell 81, 479–482, (1995).
Cordle, S. R., et al., J. Biol. Chem. 268, 11803–11810, (1993).
Darnay, B. G., et al., J. Biol. Chem. 269, 20299–20304, (1994a).
Darnay, B. G., et al., J. Biol. Chem. 269, 19687–19690, (1994b).
Darnay, B. G., et al., J. Biol. Chem. 270, 14867–14870, (1995).
Davies, D. R., et al., Annu. Rev. Biochem. 59, 439–473, (1990).
DiDonato, J. A., et al., Mol. Cell. Biol. 15, 1302–1311, (1995).
Dowdy, S. F., et al., Cell 73, 499–511, (1993).
Dyson, N., et al., Science 243, 934–937, (1989).
Ewen, M. E., et al., Cell 73, 487–497, (1993).
Featherstone, C., et al., Nature 349, 808–811, (1991).

Fields, S., et al., Nature 372, 245–246, (1989).
Finco, T. S., et al., Proc. Natl. Acad. Sci. USA 91, 11884–11888, (1994).
Gautier, J., et al., Cell 67, 197–211, (1991).
Goris, J., et al., In Advances in Protein Phosphatases (Merlevede, W., and Di Salvo, J., Eds.) 5, 579–592, Leuven Univ. Press, Leuven, Belgium, (1989).
Hadwiger, J. A., et al., P.N.A.S. USA 86, 6255–6259, (1989).
Haese, G. J. D., et al., Mol. Biol. Cell 6, 371–385, (1995).
Henkel, T., et al., Nature 365, 182–185, (1993).
Hershko, A., et al., J. Biol. Chem. 269, 4940–4946, (1994).
Hoffmann, I., et al., EMBO J. 12, 53–63, (1993).
Hoffmann, I., et al., EMBO J. 13, 4302–4310, (1994).
Hsu, H., et al., Cell 81, 495–504, (1995).
Itoh, N., et al., J. Biol. Chem. 268, 10932–10937, (1993).
Izumi, T., et al., Mol. Cell. Biol. 4, 1337–1350, (1993).
Jeffrey, P. D., et al., Nature 376, 313–320, (1995).
Kato, J. Y., et al., Genes Dev. 7, 331–342, (1993).
Lee, M. S., et al., J. Biol. Chem. 269, 30530–30537, (1994).
Lin, Y. C., et al., Proc. Natl. Acad. Sci. USA 92, 552–556, (1995).
Loetscher, H., et al., J. Biol. Chem. 265, 20131–20138, (1990).
Matsushime, H., et al., Mol. Cell. Biol. 14, 2066–2076, (1994).
McGowan, C. H., et al., EMBO J. 14, 2166–2175, (1995).
Meikrantz, W., et al., P.N.A.S. USA 91, 3754–3758, (1994).
Meikrantz, W., et al., J. Cell. Biochem. 58, 160–174, (1995).
Menon, S. D., et al., J. Biol. Chem. 270, 18881–18887, (1995).
Millar, J. B. A., et al., EMBO J. 10, 4301–4309, (1991).
Miyamoto, S., et al., P.N.A.S. USA 91, 12740–12744, (1994).
Morgan, D. O., Nature 374, 131–134, (1995).
Nigg, E. A., BioEssays 17, 471–480, (1995).
Parge, H. E., et al., Science 262, 387–395, (1993).
Parker, L. L., et al., Proc. Natl. Acad. Sci. USA 89, 2917–2921, (1992a).
Parker, L. L., et al., Science 257, 1955–1957, (1992b).
Pocsik, E., et al., J. Cell. Biochem. (in press), (1995).
Rice, N. R., et al., EMBO J. 12, 4685–4695, (1993).
Richardson, H. E., et al., Genes Dev. 4, 1332–1344, (1990).
Shi, L., et al., Science 263, 11431145, (1994).
Siebenlist, U., et al., Annu. Rev. Cell. Biol. 10, 405–455, (1994).
Singh, S., et al., J. Biol. Chem. 270, 10631–10639, (1995).
Song, R. Y., et al., J. Biol. Chem. 269, 22492–22495, (1994).
Song, R. Y., et al., J. Biol. Chem. 270, 3574–3581, (1995).
Sun, S. C., et al., Science 259, 1912–1915, (1993).
Sun, S. C., et al., Proc. Natl. Acad. Sci. USA 91, 1346–1350, (1994).
Tartaglia, L. A., et al., Cell 74, 845–853, (1993).
Thanos, D., et al., Cell 80, 529–532, (1995).
Traenckner, E. B. M., et al., EMBO J. 13, 5433–5441, (1994).
Traenckner, E. B. M., et al., EMBO J. 14, 2876–2883, (1995).
VanArsdale, T. L., et al., J. Immunol. 153, 3043–3050, (1994).
Watanabe, N., et al., EMBO J. 14, 1878–1891, (1995).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. 1 0 Changes therein and other uses will occur to those skilled in the art which are encompassed within the spirit of the invention as defined by the scope of the claims.

What is claimed is:

1. An enriched and isolated protein kinase that binds to the acidic rich-carboxy terminus of the cytoplasmic domain of the p60 form of the tumor necrosis factor receptor, said kinase phosphorylates the p60 form of the tumor necrosis factor receptor at serine and threonine residues, said kinase exhibits optimal phosphorylation in the presence of Mg2+, said kinase is inducible by tumor necrosis factor.

2. The protein kinase of claim 1, wherein said kinase phosphorylates casein, myelin basic protein and histone H1.

3. The protein kinase of claim 1, wherein said kinase binds to a region within amino acids 324–426 of said acidic rich-carboxy terminus of the cytoplasmic domain of the p60 form of the tumor necrosis factor receptor.

4. The protein kinase of claim 3, wherein said kinase binds to a region within amino acids 397–426 of said acidic rich-carboxy terminus of the cytoplasmic domain of the p60 form of the tumor necrosis factor receptor.

5. The protein kinase of claim 1, wherein said kinase is inactivated by treatment with pervanadate.

6. The protein kinase of claim 1, wherein said kinase is activated by treatment with okadaic acid.

7. The protein kinase of claim 1, wherein said kinase is inhibited by $p49^{WEE1}$ tyrosine kinase.

8. The protein kinase of claim 1, wherein said kinase is inhibited by $p^{13SUC1}$-agarose.

* * * * *

UNITED STATES PATENT AND TRADEMARK OFFICE
CERTIFICATE OF CORRECTION

PATENT NO.   : 5,856,161
DATED        : January 5, 1999
INVENTOR(S)  : Bharat B. Aggarwal et al.

It is certified that error appears in the above-identified patent and that said Letters Patent is hereby corrected as shown below:

Column 2,
Line 60, "Henkel, .1994" should read -- Henkel, 1994 --.
Line 66, please remove the beginning of a new paragraph that starts with Sun et al.

Column 4,
Line 52, "GST-p60CDΔ1 associated" should read -- GST-p60CDΔ1-associated --.
Line 54, "(0.5x106)" should read -- (0.5x10$^6$) --.

Column 8,
Line 1, "Rb$^{1110}$", should read -- Rb$^{110}$ --.
Line 28, "p60Δ2" should read -- p60Δ12 --.

Column 10,
Line 32, please remove the beginning of a new paragraph that starts with This tumor.

Column 12,
Line 62, "pGEX-2THAB-p60CDΔ1." should read -- pGEX-2THΔB-p60CDΔ1. --.
Line 64, "2THAB" should read -- 2THΔB -- in both places respectively.

Column 13,
Line 3, at the end of the line please insert -- (SEQ. ID NO. 2) --.
Line 5, at the end of the line please insert -- (SEQ. ID NO. 2) --.
Line 7, "pCMVXVBpL4p80" should read -- pCMVXVBp-L4p80 --.
Line 39, "(SEQ. ID NO. 7)" should read -- (SEQ. ID NO. 8) --
Line 64, please delete the number "1 0" at the end of the line.

Column 15,
Line 13, "U937" should read -- U-937 --.
Line 59, "GST-p60CDα1." should read -- GST-p60CDΔ1 --.
Line 60, "p60CDΔ1 associated" should read -- p60CDΔ1-associated --.

Column 17,
Line 10, "i n" should read -- in --.

Column 19,
Line 39, "proten" should read -- protein --.
Line 66, "p60TRAK" should read -- p60-TRAK --.

Column 20,
Line 12, "(397426)" should read -- (397-426) --.
Line 62, "40C." should read -- 4°C. --

UNITED STATES PATENT AND TRADEMARK OFFICE
CERTIFICATE OF CORRECTION

PATENT NO. : 5,856,161
DATED : January 5, 1999
INVENTOR(S) : Bharat B. Aggarwal et al.

It is certified that error appears in the above-identified patent and that said Letters Patent is hereby corrected as shown below:

Column 23,
Lines 26 and 27, "(GIB CO)" should read -- (GIBCO) --.
Line 57, please insert a letter -- C -- after the CA and before the TTT.

Column 27,
Line 15, "[35S]" should read -- $^{35}$S --.

Column 28,
Line 10, "GST-p60Δ5" should read -- GST-p60Δ15 --.
Line 35, please remove the beginning of a new paragraph that starts with These.

Column 30,
Line 55, "GSTp60Δ12" should read -- GST-p60Δ12 --.

Column 32,
Line 64, please remove the beginning of a new paragraph that starts with Kato et al.

Column 36,
Line 36, please delete the numbers "10".

Signed and Sealed this

Sixteenth Day of April, 2002

*Attest:*

*Attesting Officer*

JAMES E. ROGAN
*Director of the United States Patent and Trademark Office*